US009247745B2

(12) United States Patent
Soergel et al.

(10) Patent No.: US 9,247,745 B2
(45) Date of Patent: Feb. 2, 2016

(54) SUBSTITUTED PYRIDAZINES FOR CONTROLLING INVERTEBRATE PESTS

(75) Inventors: Sebastian Soergel, Ludwigshafen (DE); Christian Defieber, Mannheim (DE); Ronan Le Vezouet, Mannheim (DE); Deborah L. Culbertson, Fuquay Varina, NC (US); Douglas D. Anspaugh, Apex, NC (US)

(73) Assignee: BASF SE, Ludwigshafen (DE)

( * ) Notice: Subject to any disclaimer, the term of this patent is extended or adjusted under 35 U.S.C. 154(b) by 256 days.

(21) Appl. No.: 13/811,089

(22) PCT Filed: Jul. 18, 2011

(86) PCT No.: PCT/EP2011/062198
§ 371 (c)(1),
(2), (4) Date: Jan. 18, 2013

(87) PCT Pub. No.: WO2012/010534
PCT Pub. Date: Jan. 26, 2012

(65) Prior Publication Data
US 2013/0116264 A1    May 9, 2013

Related U.S. Application Data

(60) Provisional application No. 61/366,542, filed on Jul. 22, 2010.

(51) Int. Cl.
| | | |
|---|---|---|
| C07D 237/20 | (2006.01) |
| A01N 43/58 | (2006.01) |
| A01N 43/76 | (2006.01) |
| A01N 43/78 | (2006.01) |
| A01N 43/80 | (2006.01) |
| C07D 401/12 | (2006.01) |
| C07D 401/14 | (2006.01) |
| C07D 403/12 | (2006.01) |
| C07D 403/14 | (2006.01) |
| C07D 407/14 | (2006.01) |
| C07D 413/12 | (2006.01) |
| C07D 417/12 | (2006.01) |
| C07D 417/14 | (2006.01) |
| C07D 405/14 | (2006.01) |

(52) U.S. Cl.
CPC .............. *A01N 43/58* (2013.01); *A01N 43/76* (2013.01); *A01N 43/78* (2013.01); *A01N 43/80* (2013.01); *C07D 401/12* (2013.01); *C07D 401/14* (2013.01); *C07D 403/12* (2013.01); *C07D 403/14* (2013.01); *C07D 405/14* (2013.01); *C07D 407/14* (2013.01); *C07D 413/12* (2013.01); *C07D 417/12* (2013.01); *C07D 417/14* (2013.01)

(58) Field of Classification Search
CPC ..................................................... C07D 237/20
USPC ........................................................... 544/238
See application file for complete search history.

(56) References Cited

U.S. PATENT DOCUMENTS

| | | | |
|---|---|---|---|
| 4,820,821 A | 4/1989 | Kropp et al. | |
| 8,231,888 B2 * | 7/2012 | Lahm et al. | 424/405 |

FOREIGN PATENT DOCUMENTS

| | | |
|---|---|---|
| DE | 3436550 | 4/1985 |
| EP | 0 078 989 | 5/1983 |
| WO | WO 2010/034737 | 4/2010 |
| WO | WO 2010/034738 | 4/2010 |

OTHER PUBLICATIONS

International Preliminary Report on Patentability dated Jan. 22, 2013, prepared in International Application No. PCT/EP2011/062198.
International Search Report dated Nov. 8, 2011, prepared in International Application No. PCT/EP2011/062198.

* cited by examiner

*Primary Examiner* — Douglas M Willis
(74) *Attorney, Agent, or Firm* — Brinks Gilson & Lione

(57) ABSTRACT

The present invention relates to hetaryl (thio)carboxamide compounds of formula I, to the tautomers and N-oxides thereof and to the salts thereof:

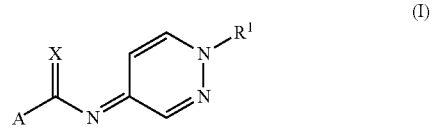

wherein
X, $R^1$ and A are as defined in the description.
The present invention further relates to a method for controlling invertebrate pests, to a method for protecting plant propagation material and/or the plants which grow therefrom, to plant propagation material, comprising at least one hetaryl (thio)carboxamide compound according to the present invention, to a method for treating or protecting an animal from infestation or infection by parasites and to an agricultural composition containing at least one compound according to the present invention.

26 Claims, No Drawings

SUBSTITUTED PYRIDAZINES FOR CONTROLLING INVERTEBRATE PESTS

This application is a National Stage application of International Application No. PCT/EP2011/062198, filed Jul. 18, 2011, which claims the benefit of U.S. Provisional Application No. 61/366,542, filed Jul. 22, 2010, the entire contents of which are hereby incorporated herein by reference.

The present invention relates to novel hetaryl (thio)carboxamide compounds, to their diastereomers, N-oxides, salts or the enantiomers or agricultural or veterinarily acceptable salts thereof which are useful for combating or controlling invertebrate pests, in particular arthropod pests and nematodes. The invention further relates to methods for controlling invertebrate pests by using these compounds. The invention further relates to a method for protecting plant propagation material and/or the plants which grow therefrom by using these compounds. The present invention further relates to plant propagation material and to an agricultural and/or veterinary compositions comprising said compounds.

Invertebrate pests and in particular arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

EP 78989 and DE 3436550 describe N-acyl amides of 1-phenylpyridazinoimines. The compounds are mentioned to be useful as a medicament for treating diseases such as hypertonia, Parkinson and depression.

WO 2010034737 and WO 2010034738 describe pyrazole compounds and their use in combating invertebrate pest is mentioned.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by compounds of the formula I, as defined below, including any possible stereoisomers of formula I, by their salts, by their tautomers and by their N-oxides and by the salts of said tautomers and N-oxides, in particular their agriculturally or veterinarily acceptable salts.

Therefore, in a first aspect the present invention relates to hetaryl (thio)carboxamide compounds of formula I,

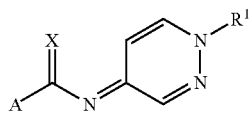

(I)

wherein
X is S or O;
$R^1$ is CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, $C_1$-$C_5$-alkylen-CN, $C_1$-$C_5$-alkylen-$OR^a$, $C(Y)R^b$, $C_1$-$C_5$-alkylen-$C(Y)R^b$, $C(Y)OR^c$, $C_1$-$C_5$-alkylen-C(Y)$OR^c$, $S(O)_m R^d$, $C_1$-$C_5$-alkylen-$NR^eR^f$, $C(Y)NR^eR^f$, $C_1$-$C_5$-alkylen-C(Y)$NR^gR^h$, $S(O)_m NR^eR^f$, $C(Y)NR^iN$-$R^eR^f$, $C_1$-$C_5$-alkylen-$S(O)_m R^d$, $C_1$-$C_5$-alkylen-S(O)$_m$N-$R^eR^d$, $C_1$-$C_5$-alkylen-C(Y)$NR^iNR^eR^f$, phenyl, heterocyclyl, hetaryl, phenyl-$C_1$-$C_5$-alkyl, $C_3$-$C_{10}$-cycloalkyl, $C_3$-$C_{10}$-cycloalkyl-$C_1$-$C_5$-alkyl, phenoxy-$C_1$-$C_5$-alkyl heterocyclyl-$C_1$-$C_5$-alkyl, hetaryl-$C_1$-$C_5$-alkyl wherein the ring of the nine last mentioned radicals may be unsubstituted or may carry 1, 2, 3, 4 or 5 identical or different substituents selected from the radicals $R^y$;

A is 5- or 6-membered hetaryl having one heteroatom moiety which is selected from the group consisting of O, S, N or N—$R^N$ as ring member and 0, 1 or 2 further heteroatom moieties N as ring members and also having 2, 3, 4 or 5 carbon atoms as ring members where the carbon atom ring members may be unsubstituted or 1, 2, 3 or 4 of the carbon atom ring members carry a radical $R^A$ as a substituent, where $R^A$ is selected from the group consisting of hydrogen, halogen, CN, $NO_2$, $C_1$-$C_{10}$-alkyl, $C_2$-$C_{10}$-alkenyl and $C_2$-$C_{10}$-alkynyl, wherein the last three mentioned radicals may be unsubstituted, may be partially or fully halogenated or may carry 1, 2 or 3 identical or different substituents $R^x$,
and also from the group consisting of $OR^a$, $C(Y)R^b$, $C(Y)OR^c$, $S(O)_m R^d$, $NR^eR^f$, heterocyclyl, phenyl, hetaryl, $C_3$-$C_{10}$-cycloalkyl and $C_5$-$C_{10}$-cycloalkenyl, wherein the last five mentioned radicals may be unsubstituted or may carry 1, 2, 3, 4 or 5 identical or different substituents $R^y$; and $R^N$ is selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, and also from the group consisting of $OR^a$, $C(Y)R^b$, $C(Y)OR^c$, $S(O)_m R^d$, $NR^eR^f$, $C(Y)NR^gR^h$, $S(O)_m NR^eR^f$, $C(Y)NR^iNR^eR^f$, $C_1$-$C_5$-alkylen-$OR^a$, $C_1$-$C_5$-alkylen-CN, $C_1$-$C_5$-alkylen-C(Y)$R^b$, $C_1$-$C_5$-alkylen-C(Y)$OR^c$, $C_1$-$C_5$-alkylen-$NR^eR^f$, $C_1$-$C_5$-alkylen-C(Y)$NR^gR^h$, $C_1$-$C_5$-alkylen-S$(O)_m R^d$, $C_1$-$C_5$-alkylen-S(O)$_m NR^eR^f$, $C_1$-$C_5$-alkylen-$NR^iNR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents $R^y$;

m is 0, 1 or 2

Y is O or S;

$R^a$, $R^b$, $R^c$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^e$, $R^f$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$, $R^h$ are independently of each other selected from hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^i$ is selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^y$ is selected from halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_3$-$C_6$-cycloalkyl, 5- to 7-membered heterocyclyl, hetaryl, phenyl, $C_3$-$C_6$-cycloalkoxy, 3- to 6-membered heterocyclyloxy, hetaryloxy and phenoxy, wherein the last 8 mentioned radicals may be unsubstituted or may carry 1, 2, 3, 4 or 5 radicals selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

and the salts thereof, the N-oxides thereof, the tautomers thereof and the salts of said N-oxides or tautomers.

The compounds of the present invention are particularly useful for controlling invertebrate pests, in particular for controlling arthropods and nematodes, especially for controlling insects, in particular for controlling insects of the order homoptera. Therefore, the invention also relates to the use of a compound of the formula I, a tautomer or an N-oxide thereof or a salt thereof, in particular an agriculturally or veterinarily acceptable salt thereof, for controlling invertebrate pests, in particular for controlling arthropods and nematodes, especially for controlling insects, in particular for controlling insects of the order homoptera.

A further aspect of the present invention relates to a method for controlling invertebrate pests which method comprises treating the pests, their food supply, their habitat or their breeding ground or a cultivated plant, plant propagation materials such as seed, soil, area, material or environment in which the pests are growing or may grow, or the materials, plants, seeds, soils, surfaces or spaces to be protected from pest attack or infestation with a pesticidally effective amount of a compound of formula I according to the present invention or a salt thereof or an N-oxide thereof or a salt of said N-oxide.

A further aspect of the present invention relates to a method for protecting plant propagation material, in particular seed and/or the plants which grow therefrom, which method comprises treating the plant propagation material with a pesticidally effective amount of a compound of the formula I according to the present invention or an agriculturally acceptable salt, a tautomer or an N-oxide thereof or an agriculturally acceptable salt of said N-oxide or of said tautomer.

A further aspect of the present invention relates to plant propagation material, comprising at least one compound of formula I according to the present invention and/or an agriculturally acceptable salt or an N-oxide thereof or an agriculturally acceptable salt of said N-oxide or of said tautomer.

A further aspect of the present invention relates to an agricultural composition containing at least one compound of formula I according to the present invention and/or an agriculturally acceptable salt thereof or an N-oxide or tautomer thereof and/or an agriculturally acceptable salt of said N-oxide or said tautomer and at least one liquid or solid carrier.

Depending on the substitution pattern, the compounds of the formula I may have one or more centers of chirality, in which case they are present as mixtures of enantiomers or diastereomers. The invention provides both the pure enantiomers or pure diastereomers of the formula I and their mixtures and the use according to the invention of the pure enantiomers or diastereomers of the compound I or its mixtures. Suitable compounds of the formula I also include all possible geometrical stereoisomers (cis/trans isomers) and mixtures thereof.

Depending on the substitution pattern, the compounds of the formula I may be present in the form of their tautomers.

Hence the invention also relates to the tautomers of the formula I and the salts of said tautomers.

The compounds of formula I as well as their N-oxides and tautomers may be amorphous or may exist in one or more different crystalline states (polymorphs) which may have different macroscopic properties such as stability or show different biological properties such as activities. The present invention includes both amorphous and crystalline compounds of formula I, their tautomers or N-oxides, mixtures of different crystalline states of the respective compound of formula I, their tautomers or N-oxides, as well as amorphous or crystalline salts thereof.

Salts of the compounds of the formula I, their tautomers or N-oxides, are preferably agriculturally and veterinarily acceptable salts. They can be formed in a customary method, e.g. by reacting the compound with an acid if the compound of formula I has a basic functionality or by reacting the compound with a suitable base if the compound of formula I has an acidic functionality.

Suitable agriculturally acceptable salts are especially the salts of those cations or the acid addition salts of those acids whose cations and anions, respectively, do not have any adverse effect on the pesticidal action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formula I with an acid of the corresponding anion, preferably of hydrochloric acid, hydrobromic acid, sulfuric acid, phosphoric acid or nitric acid.

The term "N-oxide" includes any compound of formula I which has at least one tertiary nitrogen atom that is oxidized to an N-oxide moiety.

The term "invertebrate pest" as used herein encompasses animal populations, such as arthropopde pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" as used herein includes all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "plants" comprises any types of plants including "non-cultivated plants" and in particular "cultivated plants".

The term "non-cultivated plants" refers to any wild type species or related species or related genera of a cultivated plant.

The term "cultivated plants" as used herein includes plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 1-propylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein and in the haloalkyl moieties of haloalkoxy, haloalkylthio, haloalkylcarbonyl, haloalkylsulfonyl and haloalkylsulfinyl, denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "haloalkoxy" as used herein denotes in each case a straight-chain or branched alkoxy group having from 1 to 10 carbon atoms, frequently from 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and the like.

The term "cycloalkyl" as used herein and in the cycloalkyl moieties of cycloalkoxy and cycloalkylmethyl denotes in each case a mono- or bicyclic cycloaliphatic radical having usually from 3 to 10 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "$C_n$-$C_m$-cycloalkyl-$C_o$-$C_p$-alkyl" or as used herein and in the like refer to a cycloalkyl group as defined above having n to m carbon atoms, which is bound to the remainder of the molecule via an alkyl group as defined above having o to p carbon atoms. Examples are cyclopropylmethyl, cyclopropylethyl, cyclopropylpropyl, cyclobutylmethyl, cyclobutylethyl, cyclobutylpropyl, cyclopentylmethyl, cyloppentylethyl, cyclopentylpropyl, cyclohexylmethyl, cyclohexylethyl, cyclohexylpropyl, and the like.

The term "halocycloalkyl" as used herein and in the halocycloalkyl moieties of halocycloalkylmethyl denotes in each case a mono- or bicyclic cycloaliphatic radical having usually from 3 to 10 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetra-chlorocyclopropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "alkenyl" as used herein denotes in each case a singly unsaturated hydrocarbon radical having usually 2 to 10, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 10, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkoxyalkyl" as used herein refers to alkyl usually comprising 1 to 4 carbon atoms, wherein 1 carbon atom carries an alkoxy radical usually comprising 1 to 10, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methyl-propoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "alkylcarbonyl" (alkyl-C(=O)—), as used herein refers to a straight-chain or branched saturated alkyl group as define above comprising 1 to 10 carbon atoms (=$C_1$-$C_{10}$-alkylcarbonyl), preferably 1 to 4 carbon atoms (=$C_1$-$C_4$-alkylcarbonyl) attached through the carbon atom of the carbonnyl group at any position in the alkyl group.

The term "haloalkylcarbonyl" as used herein refers to an alkylcarbonyl group as defined above wherein the hydrogen atoms are partially or fully substituted by fluorine, chlorine, bromine and/or iodine.

The term "alkylthio" (also alkylsulfanyl or alkyl-S—)" as used herein refers to a straight-chain or branched saturated alkyl group comprising 1 to 10 carbon atoms (=$C_1$-$C_{10}$-alkylthio), preferably 1 to 4 carbon atoms (=$C_1$-$C_4$-alkylthio) as defined above, which is attached via a sulfur atom at any position in the alkyl group.

The term "haloalkylthio" as used herein refers to an alkylthio group as defined above wherein the hydrogen atoms are partially or fully substituted by fluorine, chlorine, bromine and/or iodine.

The term "alkylsulfinyl" (also alkylsulfoxyl or alkyl-S(=O)—), as used herein refers to a straight-chain or branched saturated alkyl group as define above comprising 1 to 10 carbon atoms (=$C_1$-$C_{10}$-alkylsulfinyl), preferably 1 to 4 carbon atoms (=$C_1$-$C_4$-alkylsulfinyl) attached through the sulfur atom of the sulfinyl group at any position in the alkyl group.

The term "haloalkylsulfinyl" as used herein refers to an alkylsulfinyl group as defined above wherein the hydrogen atoms are partially or fully substituted by fluorine, chlorine, bromine and/or iodine.

The term "alkylsulfonyl" (also alkyl-S(=O)$_2$—) as used herein refers to a straight-chain or branched saturated alkyl group comprising 1 to 10 carbon atoms (=$C_1$-$C_{10}$-alkylsulfonyl), preferably 1 to 4 carbon atoms (=$C_1$-$C_4$-alkylsulfonyl), as defined above, which is attached via the sulfur atom of the sulfonyl group at any position in the alkyl group.

The term "haloalkylsulfonyl" as used herein refers to an alkylsulfonyl group as defined above wherein the hydrogen atoms are partially or fully substituted by fluorine, chlorine, bromine and/or iodine.

The term "heterocyclyl" includes in general 3-, 4-, 5-, 6-, 7- or 8-membered, in particular 5-, 6-, 7- or 8-membered monocyclic heterocyclic non-aromatic radicals and 8 to 10 membered bicyclic heterocyclic non-aromatic radicals, the mono- and bicyclic non-aromatic radicals may be saturated or unsaturated. The mono- and bicyclic heterocyclic non-aromatic radicals usually comprise 1, 2, 3 or 4 heteroatoms, in particular 1 or 2 heteroatoms selected from N, O and S as ring members, where S-atoms as ring members may be present as S, SO or $SO_2$. Examples of saturated or unsaturated 3-, 4-, 5-, 6-, 7- or 8-membered heterocyclic radicals comprise saturated or unsaturated, non-aromatic heterocyclic rings, such as oxiranyl, oxetanyl, thietanyl, thietanyl-5-oxid (S-oxothietanyl), thietanyl-5-dioxid (S-dioxothiethanyl), pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, S-oxothiolanyl, S-dioxothiolanyl, dihydrothienyl, S-oxodihydrothienyl, S-dioxodihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, S-oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "hetaryl" includes in general 5- or 6-membered unsaturated monocyclic heterocyclic radicals and 8 to 10 membered unsaturated bicyclic heterocyclic radicals which are aromatic, i.e. they comply with Hückel's rule (4n+2 rule). Hetaryl usually comprise 1, 2, 3 or 4 heteroatoms selected from N, O and S as ring members.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl.

The term "hetaryl" also includes bicyclic 8- to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "phenylalkyl" and "phenoxyalkyl" refers to phenyl or phenoxy, respectively, which are bound via an alkyl group, in particular a methyl group (=hetarylmethyl), to the remainder of the molecule, examples including benzyl, 1-phenylethyl, 2-phenylethyl, 2-phenoxyethyl and the like.

The terms "heterocyclylalkyl" and "hetarylalkyl" refers to heterocyclyl or hetaryl, respectively, as defined above which are bound via an alkylene group, in particular a methylene group (=heterocyclylmethyl or hetarylmethyl, respectively) or an 1,1-ethandiyl or 1,2-ethandiyl group (=1-heterocyclylethyl, 2-heterocyclylethyl, 1-hetarylethyl or 2-hetarylethyl, respectively), to the remainder of the molecule.

The remarks made below as to preferred embodiments of the variables (substituents) of the compounds of formula I are valid on their own as well as preferably in combination with each other.

The remarks made below concerning preferred embodiments of the variables further are valid concerning the compounds of formula I as well as concerning the uses and methods according to the invention and the composition according to the present invention.

A first preferred embodiment of the invention relates to the hetaryl (thio)carboxamide compounds of the formula I wherein X is O, to their N-oxides, tautomers and to the salts thereof and to the methods and uses of such compounds. These compounds are hereinafter also referred to as compounds of formula I1.

Another embodiment of the invention relates to the hetaryl (thio)carboxamide compounds of the formula I wherein X is S, to their N-oxides, tautomers and to the salts thereof and to the methods and uses of such compounds.

A particular embodiment of the invention relates to the pyrazole compounds of the formula I, to their N-oxides, tautomers and to the salts thereof, wherein $R^1$ has the following meanings:

$R^1$ is CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_3$-$C_{10}$-cycloalkylmethyl, $C_3$-$C_{10}$-halocycloalkylmethyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_4$-alkylen-CN, $C_1$-$C_4$-alkylen-OR$^a$, C(Y)R$^b$, $C_1$-$C_4$-alkylen-C(Y)R$^b$, C(Y)OR$^c$, $C_1$-$C_4$-alkylen-C(Y)OR$^c$, S(O)$_2$R$^d$, $C_1$-$C_4$-alkylen-NR$^e$R$^f$, C(Y)NR$^g$R$^h$, $C_1$-$C_4$-alkylen-C(Y)NR$^g$R$^h$, S(O)$_m$NR$^e$R$^f$, C(Y)NR$^i$N-R$^e$R$^f$, phenyl, hetaryl, 5- or 6-membered heterocyclyl, phenyl-$C_1$-$C_4$-alkyl and 5- or 6-membered heterocyclyll-$C_1$-$C_4$-alkyl or 5- or 6-membered hetaryl-$C_1$-$C_4$-alkyl wherein the ring of the six last mentioned radicals may be unsubstituted or may carry 1, 2, 3, 4 or 5, in particular 1, 2 or 3, identical or different substituents R$^y$ and wherein m is 0, 1 or 2;

wherein the radicals R$^a$, R$^b$, R$^c$, R$^d$, R$^e$, R$^f$, R$^g$, R$^h$, R$^i$, and R$^y$ are as defined above and wherein R$^a$, R$^b$, R$^c$, R$^d$, R$^e$, R$^f$, R$^g$, R$^h$, R$^i$ and R$^y$, where occurring, preferably have one of the meanings given as preferred meanings.

Among the compounds of formula I, preference is further given to each embodiment of the invention relating to $R^1$ as such or considered in combination with A and/or X.

Examples of preferred radicals $R^1$ include:
  $C_1$-$C_{10}$-alkyl, in particular $C_1$-$C_4$-alkyl, such as methyl, ethyl, n-propyl, isopropyl, n-butyl, tert.-butyl or 2-methylpropyl;

$C_1$-$C_{10}$-haloalkyl, in particular $C_1$-$C_4$-haloalkyl, such as 2-fluoroethyl, 2-chloroethyl, 2-bromethyl, 2,2-difluoroethyl, 2,2-dichloroethyl, 2,2-dibromoethyl or 2,2,2-trifluoroethyl;

$C_3$-$C_{10}$-alkenyl, in particular $C_3$-$C_4$-alkenyl such as 2-propenyl, cis or trans 2-buten-1-yl;

$C_3$-$C_4$-haloalkenyl such as 3,3-dichloro-2-propenyl or 3,3-dibromo-2-propenyl; $C_3$-$C_{10}$-alkynyl, in particular $C_3$-$C_4$-alkynyl such as propargyl, 1-methylpropargly or 2-butyn-1-yl;

$C_1$-$C_4$-alkylene-CN such as cyanomethyl or cyanoethyl; $C_1$-$C_4$-alkylen-OR$^a$ such as methoxymethyl, ethoxymethyl 2-methoxyethyl or 2-ethoxyethyl;

$C_1$-$C_4$-alkylen-NR$^e$R$^f$ such as 2-(dimethylamino)ethyl;

$C_1$-$C_4$-alkylen-C(Y)NR$^g$R$^h$ such as N,N-dimethylcarbamoylmethyl or N,N-dimethylthiocarbamoylmethyl $C_3$-$C_6$-cycloalkyl, such as cyclopropyl, cyclobutyl or cyclopentyl;

$C_3$-$C_6$-cycloalkyl-$C_1$-$C_4$-alkyl, in particular $C_3$-$C_6$-cycloalkylmethyl, 1-$C_3$-$C_6$-cycloalkylethyl or 2-$C_3$-$C_6$-cycloalkylethyl such as cyclopropylmethyl, cyclobutylmethyl or cyclopentylmethyl;

phenyl, which may be unsubstituted or may carry 1, 2, 3, 4 or 5, in particular 1, 2 or 3 radicals R$^y$ as defined herein;

phenyl-$C_1$-$C_4$-alkyl, in particular benzyl, 1-phenylethyl or 2-phenylethyl, wherein the phenyl radicals may be unsubstituted or may carry 1, 2, 3, 4 or 5, in particular 1, 2 or 3 radicals R$^y$ as defined herein, e.g. benzyl;

heterocyclyl-$C_1$-$C_4$-alkyl, in particular heterocyclylmethyl, 1-heterocyclylethyl or 2-heterocyclylethyl, wherein the heterocyclyl radicals may be unsubstituted or may carry 1, 2 or 3 radicals R$^y$ as defined above, e.g. oxetan-2-ylmethyl, oxetan-3-ylmethyl, thietan-3-ylmethyl, 3,3-dioxathietan-3-ylmethyl, oxolan-2-ylmethyl, oxolan-3-ylmethyl, oxazolin-2-ylmethyl, thiazolin-2-ylmethyl, 1H-imidazolin-2-ylmethyl, 1-methyl-1H-imidizolin-2-ylmethyl or 5,5-dimethyltetrahydrofuran-2-ylmethyl; and hetaryl, which may be unsubstituted or may carry 1, 2, 3, 4 or 5, in particular 1, 2 or 3 radicals R$^y$ as defined herein, e.g. 2-furyl, 3-furyl, 5-methylfuran-2-yl, 2-thienyl, 3-thienyl, isothiazol-3-yl, isothiazol-4-yl, isothiazol-5-yl, isoxazol-3-yl, isoxazol-4-yl, isoxazol-5-yl, oxazol-2-yl, oxazol-4-yl, oxazol-5-yl, thiazol-2-yl, thiazol-4-yl, thiazol-5-yl, 1H-pyrazol-3-yl, 1H-pyrazol-4-yl, 2H-pyrazol-3-yl, 1-methyl-1H-pyrazol-3-yl, 1-methyl-1H-pyrazol-4-yl, 1-phenyl-1H-pyrazol-4-yl, 2-methyl-2H-pyrazol-3-yl, 1H-imidazol-2-yl, 1H-imidazol-4-yl, 1H-imidazol-5-yl, 1-methyl-1H-imidazol-2-yl, 1-methyl-1H-imidazol-4-yl, 1-methyl-1H-imidazol-5-yl, 2-pyridyl or 3-pyridyl;

hetaryl-$C_1$-$C_4$-alkyl, in particular hetarylmethyl, 1-hetarylethyl or 2-hetarylethyl, wherein the hetarclyl radicals may be unsubstituted or may carry 1, 2 or 3 radicals R$^y$ as defined above, e.g. 2-furylmethyl, 3-furylmethyl, 5-methylfuran-2-ylmethyl, 2-thienylmethyl, 3-thienylmethyl, isothiazol-3-ylmethyl, isothiazol-4-ylmethyl, isothiazol-5-ylmethyl, isoxazol-3-ylmethyl, isoxazol-4-ylmethyl, isoxazol-5-ylmethyl, oxazol-2-ylmethyl, oxazol-4-ylmethyl, oxazol-5-ylmethyl, thiazol-2-ylmethyl, thiazol-4-ylmethyl, thiazol-5-ylmethyl, 1H-pyrazol-3-ylmethyl, 1H-pyrazol-4-ylmethyl, 2H-pyrazol-3-ylmethyl, 1-methyl-1H-pyrazol-3-ylmethyl, 1-methyl-1H-pyrazol-4-ylmethyl, 1-phenyl-1H-pyrazol-4-ylmethyl, 2-methyl-2H-pyrazol-3-ylmethyl, 1H-imidazol-2-ylmethyl, 1H-imidazol-4-ylmethyl, 1H-imidazol-5-ylmethyl, 1-methyl-1H-imidazol-2-ylmethyl, 1-methyl-1H-imidazol-4-ylmethyl, 1-methyl-1H-imidazol-5-ylmethyl, 2-pyridylmethyl or 3-pyridylmethyl.

A particular embodiment of the invention relates to compounds of formula I wherein R$^1$ is selected from $C_1$-$C_{10}$-alkyl, $C_1$-$C_{10}$-haloalkyl, $C_3$-$C_{10}$-alkenyl, $C_3$-$C_{10}$-alkynyl, $C_1$-$C_4$-alkylene-CN, $C_1$-$C_4$-alkylene-OR$^a$, phenyl-$C_1$-$C_4$-alkyl, in particular benzyl, $C_3$-$C_{10}$-cycloalkyl-$C_1$-$C_4$-alkyl, in particular cycloalkylmethyl, 5- or 6-membered saturated heterocyclyl-$C_1$-$C_4$-alkyl, in particular heterocyclylmethyl and 5- or 6-membered hetaryl-$C_1$-$C_4$-alkyl, in particular hetarylmethyl, where the cycloalkyl ring and the heterocyclyl ring in $C_3$-$C_{10}$-cycloalkyl-$C_1$-$C_4$-alkyl and heterocyclyl-$C_1$-$C_4$-alkyl, respectively, is unsubstituted or carry 1, 2, 3, 4 or 5, in particular 1, 2 or 3, identical or different substituents R$^y$, where the phenyl ring and the hetaryl ring in phenyl-$C_1$-$C_4$-alkyl and hetaryl-$C_1$-$C_4$-alkyl, respectively, is unsubstituted or carry 1, 2, 3, 4 or 5, in particular 1, 2 or 3, identical or different substituents R$^y$, where R$^a$ and R$^y$ are as defined herein and wherein R$^a$ and R$^y$, where occurring, preferably have one of the meanings given as preferred meanings and where R$^a$ is in particular selected from hydrogen, $C_1$-$C_4$-alkyl and $C_1$-$C_4$-haloalkyl and where R$^y$ is in particular selected from halogen, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Among this embodiment and the embodiments described below, examples of radicals R$^1$ are the following radicals, which themselves relate to particular embodiments of the compounds of formula I: methyl, ethyl, propyl, iso-propyl, tert-butyl, butyl, sec-butyl, iso-butyl, 1-methoxyethyl, 2-methoxyethyl, 1-ethoxyethyl, 2-ethoxyethyl, cyclopropylmethyl, cyanomethyl, 1-cyanoethyl, 2-cyanoethyl, cyclopropyl, 2,2,2-trifluoroethyl, pyridin-2-ylmethyl, pyridin-3-ylmethyl, pyridin-4-ylmethyl, furan-2-ylmethyl, furan-3-ylmethyl, thiophen-2-ylmethyl, thiophen-3-ylmethyl, tetrahydrofuran-2-ylmethyl, tetrahydrofuran-3-ylmethyl, pyrrol-2-ylmethyl, pyrrol-3-ylmethyl, 1-methylpyrrol-2-ylmethyl, 1-methylpyrrol-3-ylmethyl, benzyl, allyl, cis- or trans-2-buten-1-yl, propargyl and but-2-inyl.

An embodiment of the invention relates to compounds of formula I, to their N-oxides and their salts, wherein the above examples of substituents R$^1$ are in combination with other R$^1$.

A further embodiment of the invention relates to compounds of formula I, to their N-oxides and their salts, wherein the above examples of substituents R$^1$ are not in combination with other R$^1$.

A further embodiment of the invention relates to the compounds of the formula I, to their N-oxides and their salts, wherein R$^1$ is selected from the group consisting of CN, $C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl, $C_1$-$C_4$-alkylene-CN and $C_1$-$C_4$-alkylene-OR$^a$, in particular from the group consisting of CN, $C_1$-$C_4$-alkyl, $C_1$-$C_4$-haloalkyl, $C_3$-$C_4$-alkenyl, $C_3$-$C_4$-haloalkenyl, $C_3$-$C_4$-alkynyl, $C_1$-$C_4$-alkylene-CN and $C_1$-$C_4$-alkylene-OR$^a$, where R$^a$ is as defined herein and wherein R$^a$, where occurring, preferably has one of the meanings given as preferred meanings and where R$^a$ is in particular selected from hydrogen, $C_1$-$C_4$-alkyl and $C_1$-$C_4$-haloalkyl.

Another embodiment of the invention relates to the compounds of the formula I, to their N-oxides and their salts, wherein R$^1$ is selected from the group consisting of $C_1$-$C_4$-alkylene-CN, $C_1$-$C_4$-alkylene-OR$^a$, $C_1$-$C_4$-alkylene-C(Y)R$^b$, $C_1$-$C_4$-alkylen-NR$^e$R$^f$, $C_1$-$C_4$-alkylen-C(Y)NR$^g$R$^h$, phenyl-$C_1$-$C_4$-alkyl, in particular benzyl, heterocyclyl-$C_1$-$C_4$-alkyl, in particular heterocyclylmethyl, and hetaryl-$C_1$-$C_4$-alkyl, in particular hetarylmethyl, wherein the phenyl, heterocyclyl or hetaryl ring in last six mentioned radicals may be unsubstituted or may carry 1, 2, 3, 4 or 5 radicals $R^y$, which are as defined herein and which are preferably selected respectively from $NO_2$, $C_1$-$C_4$-alkoxy, $C_1$-$C_4$-haloalkoxy, $C_1$-$C_4$-alkylsulfonyl and $C_1$-$C_4$-haloalkylsulfonyl or from halogen, $NO_2$, $C_1$-$C_4$-alkyl, $C_1$-$C_4$-haloalkyl, $C_1$-$C_4$-alkoxy, $C_1$-$C_4$-haloalkoxy.

A further particular embodiment of the invention relates to compounds of the formula I, to their N-oxides and their salts, wherein $R^1$ is selected from the group consisting of phenyl and hetaryl, in particular from phenyl, wherein phenyl and hetaryl are unsubstituted or carry 1, 2, 3, 4 or 5 radicals $R^y$, which are as defined herein and which are preferably selected respectively from $NO_2$, $C_1$-$C_4$-alkoxy, $C_1$-$C_4$-haloalkoxy, $C_1$-$C_4$-alkylsulfonyl and $C_1$-$C_4$-haloalkylsulfonyl or from halogen, $NO_2$, $C_1$-$C_4$-alkyl, $C_1$-$C_4$-haloalkyl, $C_1$-$C_4$-alkoxy, $C_1$-$C_4$-haloalkoxy.

A particular preferred embodiment of the invention relates to the compounds of the formula I, to their N-oxides and their salts, wherein $R^1$ is selected from the group consisting of $C_1$-$C_4$-alkyl, $C_1$-$C_4$-haloalkyl and $C_1$-$C_4$-alkoxy-$C_1$-$C_4$-alkyl. Among this embodiment, particular preference is given to compounds, wherein $R^1$ is $C_1$-$C_3$-alkyl. Further, among this embodiment, likewise preference is given to compounds, wherein $R^1$ is $C_1$-$C_3$-haloalkyl or $C_1$-$C_2$-alkoxy-$C_1$-$C_2$-alkyl.

In another particular embodiment, the invention relates to compounds of formula I, to their N-oxides and their salts, wherein, $R^1$ is selected from the group consisting of $C_1$-$C_4$-alkylen-$NR^eR^f$, phenyl-$C_1$-$C_4$-alkyl, in particular benzyl, 1-phenylethyl or 2-phenylethyl, heterocyclyl-$C_1$-$C_4$-alkyl, in particular heterocyclylmethyl, 1-heterocyclylethyl or 2-heterocyclylethyl, and hetaryl-$C_1$-$C_4$-alkyl, in particular hetarylmethyl, 1-hetarylethyl or 2-hetarylethyl, wherein the last twelve mentioned radicals may be unsubstituted or may carry 1, 2 or 3 radicals $R^y$, which are as defined above and which are preferably selected from halogen, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

The radical $R^A$, if present, is preferably selected from the group consisting of halogen, CN, $NO_2$, $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^A$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl. In particular, the radical $R^A$, if present, is selected from halogen, CN, $NO_2$, $C_1$-$C_4$-alkyl, $C_1$-$C_4$-haloalkyl, $C_3$-$C_6$-cycloalkyl $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably, the radical $R^A$, if present, is selected from halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl. Even more preferably, $R^A$, if present, is selected from halogen, $NO_2$, $C_1$-$C_4$-alkyl, $C_1$-$C_4$-haloalkyl, $C_3$-$C_6$-cycloalkyl and $C_3$-$C_6$-halocycloalkyl. More particularly $R^A$, if present, is halogen, $C_1$-$C_2$-alkyl or $C_1$-$C_2$-haloalkyl.

Particular preferred embodiments of the invention relate to compounds of formula I, to their N-oxides and their salts, wherein A is 5-membered hetaryl having one of the formulae A1, A2, A3, A4, A5, A6 or A7

(A1)

(A2)

(A3)

(A4)

(A5)

(A6)

(A7)

wherein # denotes the point of attachment to the remainder of formula I,

Z is O, S or N—$R^N$, where $R^N$ is as defined herein, n is 0, 1, 2 or 3, $R^A$ is as defined herein, and $R^{A'}$ is hydrogen or has one of the meanings given for $R^A$.

In the formulae A1, A2 and A3 the variable n is preferably 0 or 1, in particular 1.

In the formulae A1, A2 and A3, where the variable n is 2 or 3, $R^A$ may be identical or different.

In the formulae A1, A2 and A3, the radical $R^A$, if present, is preferably selected from the group consisting of halogen, CN, $NO_2$, $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^A$ is further selected from $C_3$-$C_6$-cycloalkyl, $C_5$-$C_6$- hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl. In particular, the radical $R^A$, if present, is selected from halogen, CN, $NO_2$, $C_1$-$C_4$-alkyl, $C_1$-$C_4$-haloalkyl, $C_3$-$C_6$-cycloalkyl $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably, the radical $R^A$, if present, is selected from halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl. Even more preferably, $R^A$, if present, is selected from halogen, $NO_2$, $C_1$-$C_4$-alkyl, $C_1$-$C_4$-haloalkyl, $C_3$-$C_6$-cycloalkyl and $C_3$-$C_6$-halocycloalkyl. More particularly $R^A$, if present, is $C_1$-$C_2$-alkyl or $C_1$-$C_2$-haloalkyl.

In the formulae A4, A5, A6 and A7, the radical $R^{A'}$ may be hydrogen. In the formulae A4, A5, A6 and A7, the radical $R^{A'}$, if different from hydrogen, is preferably selected from the group consisting of halogen, CN, $NO_2$, $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^{A'}$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl. In particular, the radical $R^{A'}$, if different from hydrogen, is selected from halogen, CN, $NO_2$, $C_1$-$C_4$-alkyl, $C_1$-$C_4$-haloalkyl, $C_3$-$C_6$-cycloalkyl $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably, the radical $R^{A'}$, if different from hydrogen, is selected from halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl. Even more preferably, $R^{A'}$, if different from hydrogen, is selected from halogen, $NO_2$, $C_1$-$C_4$-alkyl, $C_1$-$C_4$-haloalkyl, $C_3$-$C_6$-cycloalkyl and $C_3$-$C_6$-halocycloalkyl. More particularly $R^{A'}$, if different from hydrogen, is $C_1$-$C_2$-alkyl or $C_1$-$C_2$-haloalkyl.

Particular embodiments of the radical A are radicals of the formulae A1, A2, A3, A4, A5, A6 and A7, where Z is N—$R^N$, where N—$R^N$ is as defined above and where $R^N$ is preferably selected from the group consisting of $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^iNR^eR^f$, $C_1$-$C_5$-alkylene-$OR^a$, $C_1$-$C_5$-alkylene-CN, $C_1$-$C_5$-alkylene-$C(Y)R^b$, $C_1$-$C_5$-alkylene-$C(Y)OR^c$, $C_1$-$C_5$-alkylene-$NR^eR^f$, $C_1$-$C_5$-alkylene-$C(Y)NR^gR^h$, $C_1$-$C_5$-alkylene-$S(O)_mR^d$, $C_1$-$C_5$-alkylene-$S(O)_mNR^eR^f$, $C_1$-$C_5$-alkylene-$NR^iNR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3 or 4 or 5 identical or different substituents $R^y$.

In particular $R^N$, if present, is selected from the group consisting of $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, $C_1$-$C_4$-alkoxy-$C_2$-$C_4$-alkyl, $C_1$-$C_4$-alkylene-CN, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, where the rings in the 8 last mentioned radicals may be unsubstituted or may carry 1, 2 or 3 identical or different substituents $R^y$.

In particular $R^N$, if present, is selected from the group consisting of $C_1$-$C_6$-alkyl, $C_1$-$C_6$-haloalkyl, $C_3$-$C_6$-cycloalkyl-$C_1$-$C_4$-alkyl, where the cycloalkyl moiety is unsubstituted or carries 1 or 2 radicals selected from halogen, CN and $C_1$-$C_2$-haloalkyl, heterocyclyl-$C_1$-$C_4$-alkyl, $C_1$-$C_4$-alkoxy-$C_1$-$C_4$-alkyl and $C_1$-$C_4$-alkylene-CN.

In particular $R^N$, if present, is selected from the group consisting of $C_1$-$C_4$-alkyl, $C_1$-$C_4$-haloalkyl, $C_1$-$C_2$-alkoxy-$C_2$-$C_4$-alkyl, $C_1$-$C_4$-alkylene-CN, $C_3$-$C_6$-cycloalkyl and $C_3$-$C_6$-cycloalkyl-$C_1$-$C_4$-alkyl, where the cycloalkyl moiety is in the last two mentioned radicals is unsubstituted or carries 1 or 2 radicals selected from halogen, CN and $C_1$-$C_2$-haloalkyll. Especially, $R^N$ if present is $C_1$-$C_4$-alkyl or $C_1$-$C_4$-haloalkyl.

A very preferred embodiment of the invention relates to compounds of formula I, to the salts and N-oxides thereof and to the methods and uses of such compounds, wherein A is a radical A2 and the remaining radicals $R^1$ and X are as here defined.

Within the embodiment relating to compounds of formula I wherein A is A2, a particularly preferred embodiment relates to compounds wherein Z is $NR^N$.

Within the embodiment relating to compounds wherein A is A2, further embodiment relates to compounds wherein Z is O.

Within the embodiment relating to compounds wherein A is A2, further embodiment relates to compounds wherein Z is S.

Among the compounds of formula I, wherein A is A2, preferred embodiment of the invention relates to compounds of the formula I, wherein X is O and $R^1$ have in particular one of the preferred meaning. Within this preferred embodiment, preference is particularly given to compounds of formula I wherein n is 1.

Among the compounds of formula I, wherein A is A2, a further embodiment relates to compounds of the formula I, wherein X is O, $R^1$ have one of the preferred meanings and wherein n is 2.

Amongst the compounds of formula I, wherein A is A2, preference is given to those compounds, wherein $R^4$, if present, is selected from the group consisting of halogen, CN, $NO_2$, $C_1$-$C_4$-alkyl and $C_2$-$C_{10}$-alkenyl, wherein the two last mentioned radicals may be unsubstituted, may be partially or fully halogenated or may carry 1, 2 or 3 identical or different substituents selected from $C_1$-$C_4$-alkoxy, $C_1$-$C_4$-haloalkoxy, $C_3$-$C_6$-cycloalkyl, hetaryl, phenyl and phenoxy, wherein the last three mentioned radicals may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl, or wherein $R^4$ is further selected from $C_3$-$C_6$-cycloalkyl, $C_5$-$C_6$-hetaryl and phenyl, wherein the three last mentioned radicals may be unsubstituted or may carry 1, 2, 3, 4 or 5 identical or different substituents selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

Amongst the compounds of formula I, wherein A is A2 particular preference is given to those compounds, wherein $R^A$ is selected from the group consisting of halogen, CN, $NO_2$, $C_1$-$C_4$-alkyl, $C_1$-$C_4$-haloalkyl, $C_3$-$C_6$-cycloalkyl $C_3$-$C_6$-halocycloalkyl and phenyl, wherein phenyl may be unsubstituted or may carry 1, 2, 3, 4 or 5 radicals selected from halogen, $C_1$-$C_4$-alkyl, $C_1$-$C_4$-haloalkyl, $C_1$-$C_4$-alkoxy and $C_1$-$C_4$-haloalkoxy. More preferably $R^A$ is selected from halogen, CN, $NO_2$, $C_1$-$C_4$-alkyl, $C_1$-$C_4$-haloalkyl, $C_3$-$C_6$-cycloalkyl and $C_3$-$C_6$-halocycloalkyl. In particular, $R^A$ is selected from hydrogen, halogen, $NO_2$, $C_1$-$C_4$-alkyl, $C_1$-$C_4$-haloalkyl, $C_3$-$C_6$-cycloalkyl and $C_3$-$C_6$-halocycloalkyl. More particularly $R^A$ is $C_1$-$C_2$-alkyl or $C_1$-$C_2$-haloalkyl.

Among the compounds of formula I, wherein A is A2, preference is further given to those compounds, wherein Z is N—$R^N$ and wherein $R^N$ selected from the group consisting of $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, or wherein $R^N$ is further selected from $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^iNR^eR^f$, $C_1$-$C_5$-alkylene-$OR^a$, $C_1$-$C_5$-alkylene-CN, $C_1$-$C_5$-alkylene-$C(Y)R^b$, $C_1$-$C_5$-alkylene-$C(Y)OR^c$, $C_1$-$C_5$-alkylene-$NR^eR^f$, $C_1$-$C_5$-alkylene-$C(Y)NR^gR^h$, $C_1$-$C_5$-alkylene-$S(O)_mR^a$, $C_1$-$C_5$-alkylene-$S(O)_mNR^eR^f$, $C_1$-$C_5$-alkylene-$NR^iNR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents $R^y$.

In the compounds of formula I, wherein A is A2 and Z is N—$R^N$, $R^N$ is more preferably selected from the group consisting of $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, $C_1$-$C_4$-alkoxy-$C_2$-$C_4$-alkyl, $C_1$-$C_4$-alkylene-CN, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, where the rings in the 8 last mentioned radicals may be unsubstituted or may carry 1, 2 or 3 identical or different substituents $R^y$.

In the compounds wherein A is A2 and Z is N—$R^N$, $R^N$ is more preferably selected from $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the cycloalkyl moiety is in the last two mentioned radicals is unsubstituted or carries 1 or 2 radicals selected from halogen, CN and $C_1$-$C_2$-haloalkyl, heterocyclyl-$C_1$-$C_4$-alkyl, $C_1$-$C_4$-alkoxy-$C_1$-$C_4$-alkyl and $C_1$-$C_4$-alkylene-CN.

In particular $R^N$, if present, is selected from the group consisting of $C_1$-$C_4$-alkyl, $C_1$-$C_4$-haloalkyl, $C_1$-$C_2$-alkoxy-$C_2$-$C_4$-alkyl, $C_1$-$C_4$-alkylene-CN, $C_3$-$C_6$-cycloalkyl and $C_3$-$C_6$-cycloalkyl-$C_1$-$C_4$-alkyl, where the cycloalkyl moiety is in the last two mentioned radicals is unsubstituted or carries 1 or 2 radicals selected from halogen, CN and $C_1$-$C_2$-haloalkyll. Especially, $R^N$ if present is $C_1$-$C_4$-alkyl or $C_1$-$C_4$-haloalkyl.

Examples of suitable radicals $R^N$ are defined in the following table $R^N$:

TABLE $R^N$

| No. | $R^N$ |
|---|---|
| R.N 1 | H |
| R.N 2 | $CH_3$ |
| R.N 3 | $CH_2CH_3$ |
| R.N 4 | $CH_2CH_2CH_3$ |
| R.N 5 | $CH(CH_3)_2$ |
| R.N 6 | $CH_2CF_3$ |
| R.N 7 | $C(CH_3)_3$ |
| R.N 8 | $C_6H_5$ |
| R.N 9 | 4-Cl—$C_6H_4$ |
| R.N 10 | 4-F—$C_6H_4$ |
| R.N 11 | 2,4-$Cl_2$—$C_6H_3$ |
| R.N 12 | 4-($CH_3O$)—$C_6H_4$ |
| R.N 13 | 2-pyridyl |
| R.N 14 | 5-Cl-2-pyridyl |
| R.N 15 | $CH_2$—$C_6H_5$ |
| R.N 16 | 4-($OCF_3$)—$C_6H_4$ |
| R.N 17 | 4-($SCF_3$)—$C_6H_4$ |
| R.N 18 | 4-($OCHF_2$)—$C_6H_4$ |
| R.N 19 | 4-($CF(CF_3)_2$)—$C_6H_4$ |
| R.N 20 | 4-($SO_2CH_3$)—$C_6H_4$ |
| R.N 21 | 2,6-Cl-4-$CF_3$—$C_6H_2$ |
| R.N 22 | 3-Cl-5-$CF_3$-pyridin-2-yl |
| R.N 23 | 3-pyridyl |
| R.N 24 | 4-pyridyl |
| R.N 25 | 2-thiazolyl |
| R.N 26 | 4,5-$(CH_3)_2$-thiazol-2-yl |
| R.N 27 | 4-thiazolyl |
| R.N 28 | 5-thiazolyl |
| R.N 29 | 4-$CF_3$-thiazol-2-yl |
| R.N 30 | 4-$CH_3$-thiazol-2-yl |
| R.N 31 | 4-$CH_3$-thiazol-2-yl |
| R.N 32 | 5-triazolyl |
| R.N 33 | 3-$CH_3$-triazol-5-yl |
| R.N 34 | $CH_2$(4-Cl—$C_6H_4$) |
| R.N 35 | 4-$NO_2$-1-pyrazolyl-methyl |
| R.N 36 | 2-imidazolyl |
| R.N 37 | 4-imidazolyl |
| R.N 38 | 5-imidazolyl |
| R.N 39 | 2-oxazolyl |
| R.N 40 | 4-oxazolyl |
| R.N 41 | 5-oxazolyl |
| R.N 42 | 3-isoxazolyl |
| R.N 43 | 4-isoxazolyl |
| R.N 44 | 5-isoxazolyl |
| R.N 45 | 3-$CH_3$-isoxazol-5-yl |
| R.N 46 | 5-$CH_3$-isoxazol-3-yl |
| R.N 47 | 3-pyrazolyl |
| R.N 48 | [1,3,4]thiadiazol-2-yl |
| R.N 49 | 5-tetrazolyl |
| R.N 50 | 4-$NO_2$—$C_6H_4$ |
| R.N 51 | 4-$CF_3$—$C_6H_4$ |
| R.N 52 | 2,4-$F_2$—$C_6H_3$ |
| R.N 53 | 3,5-$Cl_2$—$C_6H_3$ |
| R.N 54 | 3,4-$Cl_2$—$C_6H_3$ |
| R.N 55 | 4-$C(CH_3)_3$—$C_6H_4$ |
| R.N 56 | 3-Cl-$C_6H_4$ |
| R.N 57 | 3-F—$C_6H_4$ |
| R.N 58 | 2-F—$C_6H_4$ |
| R.N 59 | 2-$CF_3$—$C_6H_4$ |
| R.N 60 | 2-$CH_3O$—$C_6H_4$ |
| R.N 61 | 3-$CH_3O$—$C_6H_4$ |
| R.N 62 | 3-Cl-4-F—$C_6H_3$ |
| R.N 63 | 3-$NO_2$—$C_6H_4$ |
| R.N 64 | 2-$CH_3$—$C_6H_4$ |
| R.N 65 | 3-$CH_3$—$C_6H_4$ |
| R.N 66 | 4-$CH_3$—$C_6H_4$ |
| R.N 67 | 2-$C_6H_5$—$C_6H_4$ |
| R.N 68 | 3-$C_6H_5$—$C_6H_4$ |
| R.N 69 | 2-F-4-Cl—$C_6H_3$ |
| R.N 70 | 2,4,6-$Cl_3$—$C_6H_2$ |
| R.N 71 | 2,3,4-$Cl_3$—$C_6H_2$ |
| R.N 72 | 2,6-$F_2$—$C_6H_3$ |
| R.N 73 | $CH_2F$ |
| R.N 74 | $CHF_2$ |
| R.N 75 | $CF_3$ |
| R.N 76 | $CH_2CHF_2$ |
| R.N 77 | $CH_2Cl$ |
| R.N 78 | $CHCl_2$ |

TABLE R$^N$-continued

| No. | R$^N$ |
|---|---|
| R.N 79 | CCl$_3$ |
| R.N 80 | CH$_2$CHCl$_2$ |
| R.N 81 | CH$_2$CCl$_3$ |
| R.N 82 | CH$_2$CH(CH$_3$)$_2$ |
| R.N 83 | CH$_2$CH$_2$OCH$_3$ |
| R.N 84 | CH$_2$CH$_2$CN |
| R.N 85 | CH(CH$_3$)CH$_2$CN |
| R.N 86 | CH$_2$CH(CH$_3$)CN |
| R.N 87 | cyclopropyl |
| R.N 88 | 1-F-cyclopropyl |
| R.N 89 | 1-Cl-cyclopropyl |
| R.N 90 | cyclopropylmethyl |
| R.N 91 | 1-F-cyclopropylmethyl |
| R.N 92 | 1-Cl-cyclopropylmethyl |
| R.N 93 | 1-CF$_3$-cyclopropylmethyl |
| R.N 94 | 1-CN-cyclopropylmethyl |
| R.N 95 | 2,2-Cl$_2$-cyclopropylmethyl |
| R.N 96 | 2-NO$_2$—C$_6$H$_4$ |
| R.N 97 | 6-Cl-2-pyridyl |
| R.N 98 | 5-NO$_2$-2-pyridyl |
| R.N 99 | 3-NO$_2$-2-pyridyl |
| R.N 100 | 6-CH$_3$-5-NO$_2$-2-pyridyl |
| R.N 101 | pyrazin-2-yl |
| R.N 102 | pyrimidin-2-yl |
| R.N 103 | thiophen-3-yl |
| R.N 104 | 4-CH$_3$-5-CH(CH$_3$)$_2$-4H-[1,2,4]-triazol-3-yl |
| R.N 105 | 4-CH$_3$-5-cyclopropyl-4H-[1,2,4]-triazol-3-yl |
| R.N 106 | 4-CH$_3$-5-CF$_3$-4H-[1,2,4]-triazol-3-yl |
| R.N 107 | 4,5-(CH$_3$)$_2$-4H-[1,2,4]-triazol-3-yl |
| R.N 108 | 4-CH$_3$-5-C$_2$H$_5$-4H-[1,2,4]-triazol-3-yl |
| R.N 109 | 4-CH(CH$_3$)$_2$-4H-[1,2,4]-triazol-3-yl |
| R.N 110 | 4-cyclopropyl-4H-[1,2,4]-triazol-3-yl |
| R.N 111 | 4-CH$_3$-4H-[1,2,4]-triazol-3-yl |
| R.N 112 | 4-C$_2$H$_5$-4H-[1,2,4]-triazol-3-yl |
| R.N 113 | 4-C$_6$H$_5$-4H-[1,2,4]-triazol-3-yl |
| R.N 114 | 5-CH$_3$-1,3,4-thiadiazol-2-yl |
| R.N 115 | CH=CH$_2$ |
| R.N 116 | CH$_2$CH=CH$_2$ |
| R.N 117 | 5-C$_6$H$_5$-1,3,4-thiadiazol-2-yl |
| R.N 118 | 5-CF$_3$-1,3,4-thiadiazol-2-yl |
| R.N 119 | 5-C$_6$H$_5$-1,3,4-oxadiazol-2-yl |
| R.N 120 | 5-CF$_3$-1,3,4-oxadiazol-2-yl |
| R.N 121 | 5-CH$_3$-1,3,4-oxadiazol-2-yl |
| R.N 122 | 1-CH$_3$-1,2,3-triazol-4-yl |
| R.N 123 | 1-C$_6$H$_5$-1,2,3-triazol-4-yl |

Embodiments of the present invention relate to compounds of formula I wherein A is selected from the following suitable examples of radicals A2.

Each group of suitable radical A2 of the following example constitutes an embodiment of the invention.

Examples of suitable radicals A2 are the radicals of formulae A2.a, A2.b, A2.c, A2.d, A2.e, A2.f, A2.g, A2.h, A2.i, A2.k, A2.l, A2.m, A2.n, A2.o, A2.p, A2.q, A2.r, A2.s, A2.t, A2.u, A2.v, A2.w, A2.x, A2.y, A2.z, A2.aa, A2.bb, A2.cc, A2.dd, A2.ee, A2.ff, A2.gg, A2.hh, A2.ii, A2.kk, A2.mm, A2.nn, A2.oo, A2.pp, A2.qq, A2.rr, A2.ss, A2.tt, A2.uu and A2.vv, with preference given to radicals A2.a, A2.b, A2.c, A2.d, A2.e, A2.f, A2.n, A2.o, A2.q, A2.r, A2.s, A2.t, A2.u, A2.v, A2.w, A2.x, A2.y, A2.z, A2.aa, A2.bb, A2.cc, A2.dd, A2.ee, A2.ff, A2.gg, A2.hh, A2.kk, A2.ss, A2.tt, A2.uu and A2.vv and with particular preference given to radicals of formulae A2.o, A2.p, A2.r and A2.tt, wherein Z is O, or S or NR$^N$ with R$^N$ being as defined hereabove in the embodiment relating to R$^N$, preferably in one line of table R$^N$, in particular as defined in lines R.N 1 to R.N 8, R.N 13, R.N 15, R.N 23, R.N 24, R.N 73 to R.N 78 and R.N 82 to R.N 95.

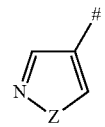

A2.a

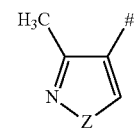

A2.b

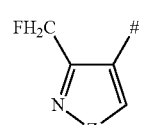

A2.c

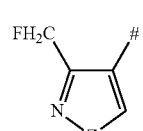

A2.d

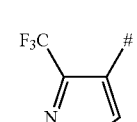

A2.e

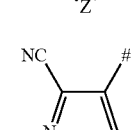

A2.f

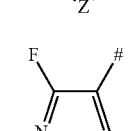

A2.g

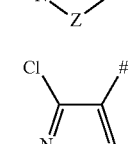

A2.h

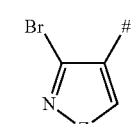

A2.i

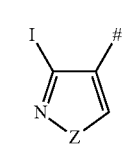

A2.k

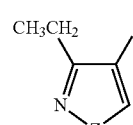

A2.l

| | |
|---|---|
| A2.m 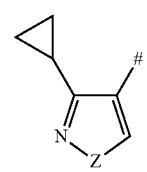 | A2.x 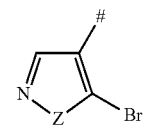 |
| A2.n 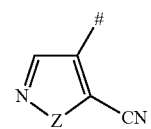 | A2.y 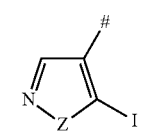 |
| A2.o 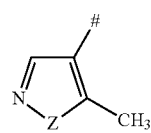 | A2.z 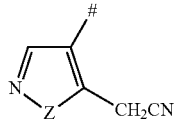 |
| A2.p 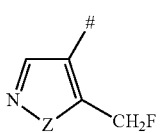 | A2.aa 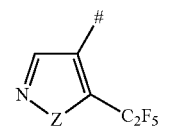 |
| A2.q 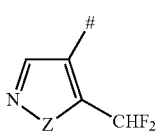 | A2.bb 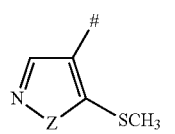 |
| A2.r 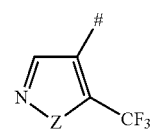 | A2.cc 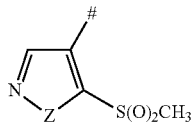 |
| A2.s 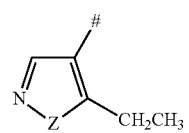 | A2.dd  |
| A2.t 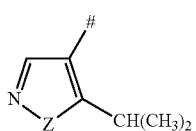 | A2.ee  |
| A2.u 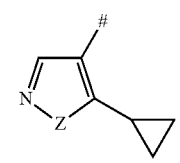 | A2.ff 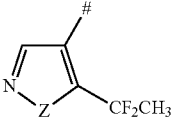 |
| A2.v 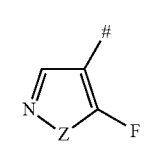 | A2.gg 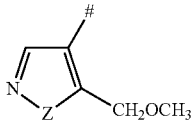 |
| A2.w 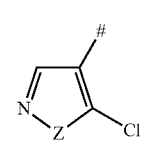 | A2.hh 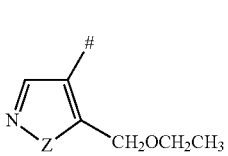 |

A2.ii 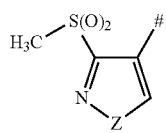

A2.kk 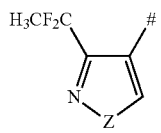

A2.mm 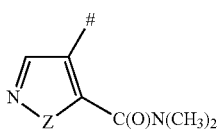

A2.nn 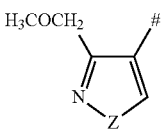

A2.oo 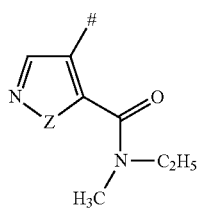

A2.pp 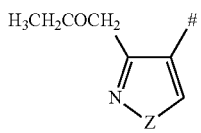

A2.qq 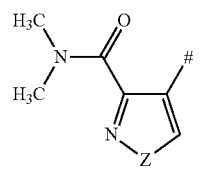

A2.rr 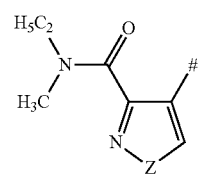

A2.ss 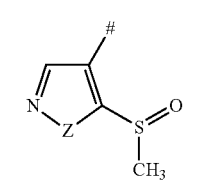

A2.tt 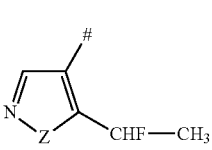

A2.uu 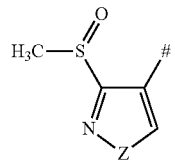

A2.vv 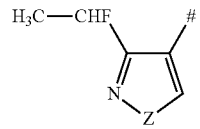

In analogy to the above cited examples of radicals of formula A2.a to A2.z, further suitable radicals A2 are the radicals of formulae A2O.a, A2O.b, A2O.c, A2O.d, A2O.e, A2O.f, A2O.g, A2O.h, A2O.i, A2O.k, A2O.l, A2O.m, A2O.n, A2O.o, A2O.p, A2O.q, A2O.r, A2O.s, A2O.t, A2O.u, A2O.v, A2O.w, A2O.x, A2O.y, A2O.z, A2O.aa, A2O.bb, A2O.cc, A2O.dd, A2O.ee, A2O.ff, A2O.gg, A2O.hh, A2O.ii, A2O.kk, A2O.mm, A2O.nn, A2O.oo, A2O.pp, A2O.qq, A2O.rr, A2O.ss, A2O.tt, A2O.uu and A2O.vv, wherein Z is O.

In analogy to the above cited examples of radicals of formula A2.a to A2.z, further suitable radicals A2 are the radicals of formulae A2S.a, A2S.b, A2S.c, A2S.d, A2S.e, A2S.f, A2S.g, A2S.h, A2S.i, A2S.k, A2S.l, A2S.m, A2S.n, A2S.o, A2S.p, A2S.q, A2S.r, A2S.s, A2S.t, A2S.u, A2S.v, A2S.w, A2S.x, A2S.y, A2S.z, A2S.aa, A2S.bb, A2O.cc, A2S.dd, A2S.ee, A2S.ff, A2S.gg, A2S.hh, A2S.ii, A2S.kk, A2S.mm, A2S.nn, A2S.oo, A2S.pp, A2S.qq, A2S.rr, A2S.ss, A2S.tt, A2S.uu and A2S.vv, wherein Z is S.

Examples of particularly preferred radicals A2 are the radicals of the type A2.Nx.a, A2Nx.a, A2Nx.b, A2Nx.c, A2Nx.d, A2Nx.e, A2Nx.f, A2Nx.g, A2Nx.h, A2Nx.i, A2Nx.k, A2NX.l, A2Nx.m, A2NX.n, A2Nx.o, A2Nx.p, A2Nx.q, A2NX.r, A2NX.s, A2Nx.t, A2NX.u, A2Nx.v, A2NX.w, A2Nx.x, A2Nx.y, A2Nx.z, A2NX.aa, A2Nx.bb, A2Nx.cc, A2Nx.dd, A2Nx.ee, A2Nx.ff, A2Nx.gg, A2Nx.hh, A2Nx.ii, A2Nx.kk, A2Nx.mm, A2Nx.nn, A2Nx.oo, A2Nx.pp, A2Nx.qq, A2Nx.rr, A2Nx.ss, A2Nx.tt, A2Nx.uu and A2Nx.vv, wherein Z is N—$R^N$ and wherein $R^N$ corresponds to one of the meanings given in lines 1 to 123 of table $R^N$.

Particularly preferred radicals A2 are the radicals of the type A2.Nx

A2.Nx 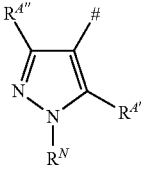

where # denotes the point of attachment to the remainder of the compound of formula I, $R^N$ is as defined herein, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

Examples of particularly preferred radicals A2 are the radicals of the type A2.Nx numbered A2.N1 to A2.N1014 wherein # denotes the point of attachment to the remainder of the compound of formula I, $R^N$, $R^{A'}$ and $R^{A''}$ are represented by each line of the following Table A.

TABLE A

| No. | $R^N$ | $R^{A''}$ | $R^{A'}$ |
|---|---|---|---|
| | Radicals A2.N . . . | | |
| 1 | H | H | H |
| 2 | H | H | $CH_3$ |
| 3 | H | H | $C_2H_5$ |
| 4 | H | H | $C_3H_7$ |
| 5 | H | H | $CHF_2$ |
| 6 | H | H | $CF_3$ |
| 7 | H | H | F |
| 8 | H | H | Cl |
| 9 | H | H | Br |
| 10 | H | H | I |
| 11 | H | H | $cC_3H_5$ |
| 12 | H | H | CN |
| 13 | H | H | $CH_2CN$ |
| 14 | H | F | H |
| 15 | H | F | $CH_3$ |
| 16 | H | F | $C_2H_5$ |
| 17 | H | F | $C_3H_7$ |
| 18 | H | F | $CHF_2$ |
| 19 | H | F | $CF_3$ |
| 20 | H | F | F |
| 21 | H | F | Cl |
| 22 | H | F | Br |
| 23 | H | F | I |
| 24 | H | F | $cC_3H_5$ |
| 25 | H | F | CN |
| 26 | H | F | $CH_2CN$ |
| 27 | H | Cl | H |
| 28 | H | Cl | $CH_3$ |
| 29 | H | Cl | $C_2H_5$ |
| 30 | H | Cl | $C_3H_7$ |
| 31 | H | Cl | $CHF_2$ |
| 32 | H | Cl | $CF_3$ |
| 33 | H | Cl | F |
| 34 | H | Cl | Cl |
| 35 | H | Cl | Br |
| 36 | H | Cl | I |
| 37 | H | Cl | $cC_3H_5$ |
| 38 | H | Cl | CN |
| 39 | H | Cl | $CH_2CN$ |
| 40 | $CH_3$ | H | H |
| 41 | $CH_3$ | H | $CH_3$ |
| 42 | $CH_3$ | H | $C_2H_5$ |
| 43 | $CH_3$ | H | $C_3H_7$ |
| 44 | $CH_3$ | H | $CHF_2$ |
| 45 | $CH_3$ | H | $CF_3$ |
| 46 | $CH_3$ | H | F |
| 47 | $CH_3$ | H | Cl |
| 48 | $CH_3$ | H | Br |
| 49 | $CH_3$ | H | I |
| 50 | $CH_3$ | H | $cC_3H_5$ |
| 51 | $CH_3$ | H | CN |
| 52 | $CH_3$ | H | $CH_2CN$ |
| 53 | $CH_3$ | F | H |
| 54 | $CH_3$ | F | $CH_3$ |
| 55 | $CH_3$ | F | $C_2H_5$ |
| 56 | $CH_3$ | F | $C_3H_7$ |
| 57 | $CH_3$ | F | $CHF_2$ |
| 58 | $CH_3$ | F | $CF_3$ |
| 59 | $CH_3$ | F | F |
| 60 | $CH_3$ | F | Cl |
| 61 | $CH_3$ | F | Br |
| 62 | $CH_3$ | F | I |
| 63 | $CH_3$ | F | $cC_3H_5$ |
| 64 | $CH_3$ | F | CN |
| 65 | $CH_3$ | F | $CH_2CN$ |
| 66 | $CH_3$ | Cl | H |
| 67 | $CH_3$ | Cl | $CH_3$ |
| 68 | $CH_3$ | Cl | $C_2H_5$ |
| 69 | $CH_3$ | Cl | $C_3H_7$ |
| 70 | $CH_3$ | Cl | $CHF_2$ |
| 71 | $CH_3$ | Cl | $CF_3$ |
| 72 | $CH_3$ | Cl | F |
| 73 | $CH_3$ | Cl | Cl |
| 74 | $CH_3$ | Cl | Br |
| 75 | $CH_3$ | Cl | I |
| 76 | $CH_3$ | Cl | $cC_3H_5$ |
| 77 | $CH_3$ | Cl | CN |
| 78 | $CH_3$ | Cl | $CH_2CN$ |
| 79 | $CH_2CH_3$ | H | H |
| 80 | $CH_2CH_3$ | H | $CH_3$ |
| 81 | $CH_2CH_3$ | H | $C_2H_5$ |
| 82 | $CH_2CH_3$ | H | $C_3H_7$ |
| 83 | $CH_2CH_3$ | H | $CHF_2$ |
| 84 | $CH_2CH_3$ | H | $CF_3$ |
| 85 | $CH_2CH_3$ | H | F |
| 86 | $CH_2CH_3$ | H | Cl |
| 87 | $CH_2CH_3$ | H | Br |
| 88 | $CH_2CH_3$ | H | I |
| 89 | $CH_2CH_3$ | H | $cC_3H_5$ |
| 90 | $CH_2CH_3$ | H | CN |
| 91 | $CH_2CH_3$ | H | $CH_2CN$ |
| 92 | $CH_2CH_3$ | F | H |
| 93 | $CH_2CH_3$ | F | $CH_3$ |
| 94 | $CH_2CH_3$ | F | $C_2H_5$ |
| 95 | $CH_2CH_3$ | F | $C_3H_7$ |
| 96 | $CH_2CH_3$ | F | $CHF_2$ |
| 97 | $CH_2CH_3$ | F | $CF_3$ |
| 98 | $CH_2CH_3$ | F | F |
| 99 | $CH_2CH_3$ | F | Cl |
| 100 | $CH_2CH_3$ | F | Br |
| 101 | $CH_2CH_3$ | F | I |
| 102 | $CH_2CH_3$ | F | $cC_3H_5$ |
| 103 | $CH_2CH_3$ | F | CN |
| 104 | $CH_2CH_3$ | F | $CH_2CN$ |
| 105 | $CH_2CH_3$ | Cl | H |
| 106 | $CH_2CH_3$ | Cl | $CH_3$ |
| 107 | $CH_2CH_3$ | Cl | $C_2H_5$ |
| 108 | $CH_2CH_3$ | Cl | $C_3H_7$ |
| 109 | $CH_2CH_3$ | Cl | $CHF_2$ |
| 110 | $CH_2CH_3$ | Cl | $CF_3$ |
| 111 | $CH_2CH_3$ | Cl | F |
| 112 | $CH_2CH_3$ | Cl | Cl |
| 113 | $CH_2CH_3$ | Cl | Br |
| 114 | $CH_2CH_3$ | Cl | I |
| 115 | $CH_2CH_3$ | Cl | $cC_3H_5$ |
| 116 | $CH_2CH_3$ | Cl | CN |
| 117 | $CH_2CH_3$ | Cl | $CH_2CN$ |
| 118 | $CH_2CH_2CH_3$ | H | H |
| 119 | $CH_2CH_2CH_3$ | H | $CH_3$ |
| 120 | $CH_2CH_2CH_3$ | H | $C_2H_5$ |
| 121 | $CH_2CH_2CH_3$ | H | $C_3H_7$ |
| 122 | $CH_2CH_2CH_3$ | H | $CHF_2$ |
| 123 | $CH_2CH_2CH_3$ | H | $CF_3$ |
| 124 | $CH_2CH_2CH_3$ | H | F |
| 125 | $CH_2CH_2CH_3$ | H | Cl |
| 126 | $CH_2CH_2CH_3$ | H | Br |
| 127 | $CH_2CH_2CH_3$ | H | I |
| 128 | $CH_2CH_2CH_3$ | H | $cC_3H_5$ |
| 129 | $CH_2CH_2CH_3$ | H | CN |
| 130 | $CH_2CH_2CH_3$ | H | $CH_2CN$ |
| 131 | $CH_2CH_2CH_3$ | F | H |
| 132 | $CH_2CH_2CH_3$ | F | $CH_3$ |
| 133 | $CH_2CH_2CH_3$ | F | $C_2H_5$ |
| 134 | $CH_2CH_2CH_3$ | F | $C_3H_7$ |
| 135 | $CH_2CH_2CH_3$ | F | $CHF_2$ |
| 136 | $CH_2CH_2CH_3$ | F | $CF_3$ |
| 137 | $CH_2CH_2CH_3$ | F | F |
| 138 | $CH_2CH_2CH_3$ | F | Cl |
| 139 | $CH_2CH_2CH_3$ | F | Br |
| 140 | $CH_2CH_2CH_3$ | F | I |
| 141 | $CH_2CH_2CH_3$ | F | $cC_3H_5$ |
| 142 | $CH_2CH_2CH_3$ | F | CN |
| 143 | $CH_2CH_2CH_3$ | F | $CH_2CN$ |
| 144 | $CH_2CH_2CH_3$ | Cl | H |
| 145 | $CH_2CH_2CH_3$ | Cl | $CH_3$ |
| 146 | $CH_2CH_2CH_3$ | Cl | $C_2H_5$ |
| 147 | $CH_2CH_2CH_3$ | Cl | $C_3H_7$ |
| 148 | $CH_2CH_2CH_3$ | Cl | $CHF_2$ |

TABLE A-continued

Radicals A2.N . . .

| No. | $R^N$ | $R^{A''}$ | $R^{A'}$ |
|---|---|---|---|
| 149 | $CH_2CH_2CH_3$ | Cl | $CF_3$ |
| 150 | $CH_2CH_2CH_3$ | Cl | F |
| 151 | $CH_2CH_2CH_3$ | Cl | Cl |
| 152 | $CH_2CH_2CH_3$ | Cl | Br |
| 153 | $CH_2CH_2CH_3$ | Cl | I |
| 154 | $CH_2CH_2CH_3$ | Cl | $cC_3H_5$ |
| 155 | $CH_2CH_2CH_3$ | Cl | CN |
| 156 | $CH_2CH_2CH_3$ | Cl | $CH_2CN$ |
| 157 | $CH(CH_3)_2$ | H | H |
| 158 | $CH(CH_3)_2$ | H | $CH_3$ |
| 159 | $CH(CH_3)_2$ | H | $C_2H_5$ |
| 160 | $CH(CH_3)_2$ | H | $C_3H_7$ |
| 161 | $CH(CH_3)_2$ | H | $CHF_2$ |
| 162 | $CH(CH_3)_2$ | H | $CF_3$ |
| 163 | $CH(CH_3)_2$ | H | F |
| 164 | $CH(CH_3)_2$ | H | Cl |
| 165 | $CH(CH_3)_2$ | H | Br |
| 166 | $CH(CH_3)_2$ | H | I |
| 167 | $CH(CH_3)_2$ | H | $cC_3H_5$ |
| 168 | $CH(CH_3)_2$ | H | CN |
| 169 | $CH(CH_3)_2$ | H | $CH_2CN$ |
| 170 | $CH(CH_3)_2$ | F | H |
| 171 | $CH(CH_3)_2$ | F | $CH_3$ |
| 172 | $CH(CH_3)_2$ | F | $C_2H_5$ |
| 173 | $CH(CH_3)_2$ | F | $C_3H_7$ |
| 174 | $CH(CH_3)_2$ | F | $CHF_2$ |
| 175 | $CH(CH_3)_2$ | F | $CF_3$ |
| 176 | $CH(CH_3)_2$ | F | F |
| 177 | $CH(CH_3)_2$ | F | Cl |
| 178 | $CH(CH_3)_2$ | F | Br |
| 179 | $CH(CH_3)_2$ | F | I |
| 180 | $CH(CH_3)_2$ | F | $cC_3H_5$ |
| 181 | $CH(CH_3)_2$ | F | CN |
| 182 | $CH(CH_3)_2$ | F | $CH_2CN$ |
| 183 | $CH(CH_3)_2$ | Cl | H |
| 184 | $CH(CH_3)_2$ | Cl | $CH_3$ |
| 185 | $CH(CH_3)_2$ | Cl | $C_2H_5$ |
| 186 | $CH(CH_3)_2$ | Cl | $C_3H_7$ |
| 187 | $CH(CH_3)_2$ | Cl | $CHF_2$ |
| 188 | $CH(CH_3)_2$ | Cl | $CF_3$ |
| 189 | $CH(CH_3)_2$ | Cl | F |
| 190 | $CH(CH_3)_2$ | Cl | Cl |
| 191 | $CH(CH_3)_2$ | Cl | Br |
| 192 | $CH(CH_3)_2$ | Cl | I |
| 193 | $CH(CH_3)_2$ | Cl | $cC_3H_5$ |
| 194 | $CH(CH_3)_2$ | Cl | CN |
| 195 | $CH(CH_3)_2$ | Cl | $CH_2CN$ |
| 196 | $CH_2CF_3$ | H | H |
| 197 | $CH_2CF_3$ | H | $CH_3$ |
| 198 | $CH_2CF_3$ | H | $C_2H_5$ |
| 199 | $CH_2CF_3$ | H | $C_3H_7$ |
| 200 | $CH_2CF_3$ | H | $CHF_2$ |
| 201 | $CH_2CF_3$ | H | $CF_3$ |
| 202 | $CH_2CF_3$ | H | F |
| 203 | $CH_2CF_3$ | H | Cl |
| 204 | $CH_2CF_3$ | H | Br |
| 205 | $CH_2CF_3$ | H | I |
| 206 | $CH_2CF_3$ | H | $cC_3H_5$ |
| 207 | $CH_2CF_3$ | H | CN |
| 208 | $CH_2CF_3$ | H | $CH_2CN$ |
| 209 | $CH_2CF_3$ | F | H |
| 210 | $CH_2CF_3$ | F | $CH_3$ |
| 211 | $CH_2CF_3$ | F | $C_2H_5$ |
| 212 | $CH_2CF_3$ | F | $C_3H_7$ |
| 213 | $CH_2CF_3$ | F | $CHF_2$ |
| 214 | $CH_2CF_3$ | F | $CF_3$ |
| 215 | $CH_2CF_3$ | F | F |
| 216 | $CH_2CF_3$ | F | Cl |
| 217 | $CH_2CF_3$ | F | Br |
| 218 | $CH_2CF_3$ | F | I |
| 219 | $CH_2CF_3$ | F | $cC_3H_5$ |
| 220 | $CH_2CF_3$ | F | CN |
| 221 | $CH_2CF_3$ | F | $CH_2CN$ |
| 222 | $CH_2CF_3$ | Cl | H |
| 223 | $CH_2CF_3$ | Cl | $CH_3$ |
| 224 | $CH_2CF_3$ | Cl | $C_2H_5$ |
| 225 | $CH_2CF_3$ | Cl | $C_3H_7$ |
| 226 | $CH_2CF_3$ | Cl | $CHF_2$ |
| 227 | $CH_2CF_3$ | Cl | $CF_3$ |
| 228 | $CH_2CF_3$ | Cl | F |
| 229 | $CH_2CF_3$ | Cl | Cl |
| 230 | $CH_2CF_3$ | Cl | Br |
| 231 | $CH_2CF_3$ | Cl | I |
| 232 | $CH_2CF_3$ | Cl | $cC_3H_5$ |
| 233 | $CH_2CF_3$ | Cl | CN |
| 234 | $CH_2CF_3$ | Cl | $CH_2CN$ |
| 235 | $C(CH_3)_3$ | H | H |
| 236 | $C(CH_3)_3$ | H | $CH_3$ |
| 237 | $C(CH_3)_3$ | H | $C_2H_5$ |
| 238 | $C(CH_3)_3$ | H | $C_3H_7$ |
| 239 | $C(CH_3)_3$ | H | $CHF_2$ |
| 240 | $C(CH_3)_3$ | H | $CF_3$ |
| 241 | $C(CH_3)_3$ | H | F |
| 242 | $C(CH_3)_3$ | H | Cl |
| 243 | $C(CH_3)_3$ | H | Br |
| 244 | $C(CH_3)_3$ | H | I |
| 245 | $C(CH_3)_3$ | H | $cC_3H_5$ |
| 246 | $C(CH_3)_3$ | H | CN |
| 247 | $C(CH_3)_3$ | H | $CH_2CN$ |
| 248 | $C(CH_3)_3$ | F | H |
| 249 | $C(CH_3)_3$ | F | $CH_3$ |
| 250 | $C(CH_3)_3$ | F | $C_2H_5$ |
| 251 | $C(CH_3)_3$ | F | $C_3H_7$ |
| 252 | $C(CH_3)_3$ | F | $CHF_2$ |
| 253 | $C(CH_3)_3$ | F | $CF_3$ |
| 254 | $C(CH_3)_3$ | F | F |
| 255 | $C(CH_3)_3$ | F | Cl |
| 256 | $C(CH_3)_3$ | F | Br |
| 257 | $C(CH_3)_3$ | F | I |
| 258 | $C(CH_3)_3$ | F | $cC_3H_5$ |
| 259 | $C(CH_3)_3$ | F | CN |
| 260 | $C(CH_3)_3$ | F | $CH_2CN$ |
| 261 | $C(CH_3)_3$ | Cl | H |
| 262 | $C(CH_3)_3$ | Cl | $CH_3$ |
| 263 | $C(CH_3)_3$ | Cl | $C_2H_5$ |
| 264 | $C(CH_3)_3$ | Cl | $C_3H_7$ |
| 265 | $C(CH_3)_3$ | Cl | $CHF_2$ |
| 266 | $C(CH_3)_3$ | Cl | $CF_3$ |
| 267 | $C(CH_3)_3$ | Cl | F |
| 268 | $C(CH_3)_3$ | Cl | Cl |
| 269 | $C(CH_3)_3$ | Cl | Br |
| 270 | $C(CH_3)_3$ | Cl | I |
| 271 | $C(CH_3)_3$ | Cl | $cC_3H_5$ |
| 272 | $C(CH_3)_3$ | Cl | CN |
| 273 | $C(CH_3)_3$ | Cl | $CH_2CN$ |
| 274 | $CH_2F$ | H | H |
| 275 | $CH_2F$ | H | $CH_3$ |
| 276 | $CH_2F$ | H | $C_2H_5$ |
| 277 | $CH_2F$ | H | $C_3H_7$ |
| 278 | $CH_2F$ | H | $CHF_2$ |
| 279 | $CH_2F$ | H | $CF_3$ |
| 280 | $CH_2F$ | H | F |
| 281 | $CH_2F$ | H | Cl |
| 282 | $CH_2F$ | H | Br |
| 283 | $CH_2F$ | H | I |
| 284 | $CH_2F$ | H | $cC_3H_5$ |
| 285 | $CH_2F$ | H | CN |
| 286 | $CH_2F$ | H | $CH_2CN$ |
| 287 | $CH_2F$ | F | H |
| 288 | $CH_2F$ | F | $CH_3$ |
| 289 | $CH_2F$ | F | $C_2H_5$ |
| 290 | $CH_2F$ | F | $C_3H_7$ |
| 291 | $CH_2F$ | F | $CHF_2$ |
| 292 | $CH_2F$ | F | $CF_3$ |
| 293 | $CH_2F$ | F | F |
| 294 | $CH_2F$ | F | Cl |
| 295 | $CH_2F$ | F | Br |
| 296 | $CH_2F$ | F | I |
| 297 | $CH_2F$ | F | $cC_3H_5$ |
| 298 | $CH_2F$ | F | CN |
| 299 | $CH_2F$ | F | $CH_2CN$ |
| 300 | $CH_2F$ | Cl | H |

TABLE A-continued

Radicals A2.N . . .

| No. | $R^N$ | $R^{A''}$ | $R^{A'}$ |
|---|---|---|---|
| 301 | CH$_2$F | Cl | CH$_3$ |
| 302 | CH$_2$F | Cl | C$_2$H$_5$ |
| 303 | CH$_2$F | Cl | C$_3$H$_7$ |
| 304 | CH$_2$F | Cl | CHF$_2$ |
| 305 | CH$_2$F | Cl | CF$_3$ |
| 306 | CH$_2$F | Cl | F |
| 307 | CH$_2$F | Cl | Cl |
| 308 | CH$_2$F | Cl | Br |
| 309 | CH$_2$F | Cl | I |
| 310 | CH$_2$F | Cl | cC$_3$H$_5$ |
| 311 | CH$_2$F | Cl | CN |
| 312 | CH$_2$F | Cl | CH$_2$CN |
| 313 | CHF$_2$ | H | H |
| 314 | CHF$_2$ | H | CH$_3$ |
| 315 | CHF$_2$ | H | C$_2$H$_5$ |
| 316 | CHF$_2$ | H | C$_3$H$_7$ |
| 317 | CHF$_2$ | H | CHF$_2$ |
| 318 | CHF$_2$ | H | CF$_3$ |
| 319 | CHF$_2$ | H | F |
| 320 | CHF$_2$ | H | Cl |
| 321 | CHF$_2$ | H | Br |
| 322 | CHF$_2$ | H | I |
| 323 | CHF$_2$ | H | cC$_3$H$_5$ |
| 324 | CHF$_2$ | H | CN |
| 325 | CHF$_2$ | H | CH$_2$CN |
| 326 | CHF$_2$ | F | H |
| 327 | CHF$_2$ | F | CH$_3$ |
| 328 | CHF$_2$ | F | C$_2$H$_5$ |
| 329 | CHF$_2$ | F | C$_3$H$_7$ |
| 330 | CHF$_2$ | F | CHF$_2$ |
| 331 | CHF$_2$ | F | CF$_3$ |
| 332 | CHF$_2$ | F | F |
| 333 | CHF$_2$ | F | Cl |
| 334 | CHF$_2$ | F | Br |
| 335 | CHF$_2$ | F | I |
| 336 | CHF$_2$ | F | cC$_3$H$_5$ |
| 337 | CHF$_2$ | F | CN |
| 338 | CHF$_2$ | F | CH$_2$CN |
| 339 | CHF$_2$ | Cl | H |
| 340 | CHF$_2$ | Cl | CH$_3$ |
| 341 | CHF$_2$ | Cl | C$_2$H$_5$ |
| 342 | CHF$_2$ | Cl | C$_3$H$_7$ |
| 343 | CHF$_2$ | Cl | CHF$_2$ |
| 344 | CHF$_2$ | Cl | CF$_3$ |
| 345 | CHF$_2$ | Cl | F |
| 346 | CHF$_2$ | Cl | Cl |
| 347 | CHF$_2$ | Cl | Br |
| 348 | CHF$_2$ | Cl | I |
| 349 | CHF$_2$ | Cl | cC$_3$H$_5$ |
| 350 | CHF$_2$ | Cl | CN |
| 351 | CHF$_2$ | Cl | CH$_2$CN |
| 352 | CF$_3$ | H | H |
| 353 | CF$_3$ | H | CH$_3$ |
| 354 | CF$_3$ | H | C$_2$H$_5$ |
| 355 | CF$_3$ | H | C$_3$H$_7$ |
| 356 | CF$_3$ | H | CHF$_2$ |
| 357 | CF$_3$ | H | CF$_3$ |
| 358 | CF$_3$ | H | F |
| 359 | CF$_3$ | H | Cl |
| 360 | CF$_3$ | H | Br |
| 361 | CF$_3$ | H | I |
| 362 | CF$_3$ | H | cC$_3$H$_5$ |
| 363 | CF$_3$ | H | CN |
| 364 | CF$_3$ | H | CH$_2$CN |
| 365 | CF$_3$ | F | H |
| 366 | CF$_3$ | F | CH$_3$ |
| 367 | CF$_3$ | F | C$_2$H$_5$ |
| 368 | CF$_3$ | F | C$_3$H$_7$ |
| 369 | CF$_3$ | F | CHF$_2$ |
| 370 | CF$_3$ | F | CF$_3$ |
| 371 | CF$_3$ | F | F |
| 372 | CF$_3$ | F | Cl |
| 373 | CF$_3$ | F | Br |
| 374 | CF$_3$ | F | I |
| 375 | CF$_3$ | F | cC$_3$H$_5$ |
| 376 | CF$_3$ | F | CN |
| 377 | CF$_3$ | F | CH$_2$CN |
| 378 | CF$_3$ | Cl | H |
| 379 | CF$_3$ | Cl | CH$_3$ |
| 380 | CF$_3$ | Cl | C$_2$H$_5$ |
| 381 | CF$_3$ | Cl | C$_3$H$_7$ |
| 382 | CF$_3$ | Cl | CHF$_2$ |
| 383 | CF$_3$ | Cl | CF$_3$ |
| 384 | CF$_3$ | Cl | F |
| 385 | CF$_3$ | Cl | Cl |
| 386 | CF$_3$ | Cl | Br |
| 387 | CF$_3$ | Cl | I |
| 388 | CF$_3$ | Cl | cC$_3$H$_5$ |
| 389 | CF$_3$ | Cl | CN |
| 390 | CF$_3$ | Cl | CH$_2$CN |
| 391 | CH$_2$CHF$_2$ | H | H |
| 392 | CH$_2$CHF$_2$ | H | CH$_3$ |
| 393 | CH$_2$CHF$_2$ | H | C$_2$H$_5$ |
| 394 | CH$_2$CHF$_2$ | H | C$_3$H$_7$ |
| 395 | CH$_2$CHF$_2$ | H | CHF$_2$ |
| 396 | CH$_2$CHF$_2$ | H | CF$_3$ |
| 397 | CH$_2$CHF$_2$ | H | F |
| 398 | CH$_2$CHF$_2$ | H | Cl |
| 399 | CH$_2$CHF$_2$ | H | Br |
| 400 | CH$_2$CHF$_2$ | H | I |
| 401 | CH$_2$CHF$_2$ | H | cC$_3$H$_5$ |
| 402 | CH$_2$CHF$_2$ | H | CN |
| 403 | CH$_2$CHF$_2$ | H | CH$_2$CN |
| 404 | CH$_2$CHF$_2$ | F | H |
| 405 | CH$_2$CHF$_2$ | F | CH$_3$ |
| 406 | CH$_2$CHF$_2$ | F | C$_2$H$_5$ |
| 407 | CH$_2$CHF$_2$ | F | C$_3$H$_7$ |
| 408 | CH$_2$CHF$_2$ | F | CHF$_2$ |
| 409 | CH$_2$CHF$_2$ | F | CF$_3$ |
| 410 | CH$_2$CHF$_2$ | F | F |
| 411 | CH$_2$CHF$_2$ | F | Cl |
| 412 | CH$_2$CHF$_2$ | F | Br |
| 413 | CH$_2$CHF$_2$ | F | I |
| 414 | CH$_2$CHF$_2$ | F | cC$_3$H$_5$ |
| 415 | CH$_2$CHF$_2$ | F | CN |
| 416 | CH$_2$CHF$_2$ | F | CH$_2$CN |
| 417 | CH$_2$CHF$_2$ | Cl | H |
| 418 | CH$_2$CHF$_2$ | Cl | CH$_3$ |
| 419 | CH$_2$CHF$_2$ | Cl | C$_2$H$_5$ |
| 420 | CH$_2$CHF$_2$ | Cl | C$_3$H$_7$ |
| 421 | CH$_2$CHF$_2$ | Cl | CHF$_2$ |
| 422 | CH$_2$CHF$_2$ | Cl | CF$_3$ |
| 423 | CH$_2$CHF$_2$ | Cl | F |
| 424 | CH$_2$CHF$_2$ | Cl | Cl |
| 425 | CH$_2$CHF$_2$ | Cl | Br |
| 426 | CH$_2$CHF$_2$ | Cl | I |
| 427 | CH$_2$CHF$_2$ | Cl | cC$_3$H$_5$ |
| 428 | CH$_2$CHF$_2$ | Cl | CN |
| 429 | CH$_2$CHF$_2$ | Cl | CH$_2$CN |
| 430 | CH$_2$Cl | H | H |
| 431 | CH$_2$Cl | H | CH$_3$ |
| 432 | CH$_2$Cl | H | C$_2$H$_5$ |
| 433 | CH$_2$Cl | H | C$_3$H$_7$ |
| 434 | CH$_2$Cl | H | CHF$_2$ |
| 435 | CH$_2$Cl | H | CF$_3$ |
| 436 | CH$_2$Cl | H | F |
| 437 | CH$_2$Cl | H | Cl |
| 438 | CH$_2$Cl | H | Br |
| 439 | CH$_2$Cl | H | I |
| 440 | CH$_2$Cl | H | cC$_3$H$_5$ |
| 441 | CH$_2$Cl | H | CN |
| 442 | CH$_2$Cl | H | CH$_2$CN |
| 443 | CH$_2$Cl | F | H |
| 444 | CH$_2$Cl | F | CH$_3$ |
| 445 | CH$_2$Cl | F | C$_2$H$_5$ |
| 446 | CH$_2$Cl | F | C$_3$H$_7$ |
| 447 | CH$_2$Cl | F | CHF$_2$ |
| 448 | CH$_2$Cl | F | CF$_3$ |
| 449 | CH$_2$Cl | F | F |
| 450 | CH$_2$Cl | F | Cl |
| 451 | CH$_2$Cl | F | Br |
| 452 | CH$_2$Cl | F | I |

TABLE A-continued

Radicals A2.N...

| No. | R$^N$ | R$^{A''}$ | R$^{A'}$ |
|---|---|---|---|
| 453 | CH$_2$Cl | F | cC$_3$H$_5$ |
| 454 | CH$_2$Cl | F | CN |
| 455 | CH$_2$Cl | F | CH$_2$CN |
| 456 | CH$_2$Cl | Cl | H |
| 457 | CH$_2$Cl | Cl | CH$_3$ |
| 458 | CH$_2$Cl | Cl | C$_2$H$_5$ |
| 459 | CH$_2$Cl | Cl | C$_3$H$_7$ |
| 460 | CH$_2$Cl | Cl | CHF$_2$ |
| 461 | CH$_2$Cl | Cl | CF$_3$ |
| 462 | CH$_2$Cl | Cl | F |
| 463 | CH$_2$Cl | Cl | Cl |
| 464 | CH$_2$Cl | Cl | Br |
| 465 | CH$_2$Cl | Cl | I |
| 466 | CH$_2$Cl | Cl | cC$_3$H$_5$ |
| 467 | CH$_2$Cl | Cl | CN |
| 468 | CH$_2$Cl | Cl | CH$_2$CN |
| 469 | CH$_2$CH(CH$_3$)$_2$ | H | H |
| 470 | CH$_2$CH(CH$_3$)$_2$ | H | CH$_3$ |
| 471 | CH$_2$CH(CH$_3$)$_2$ | H | C$_2$H$_5$ |
| 472 | CH$_2$CH(CH$_3$)$_2$ | H | C$_3$H$_7$ |
| 473 | CH$_2$CH(CH$_3$)$_2$ | H | CHF$_2$ |
| 474 | CH$_2$CH(CH$_3$)$_2$ | H | CF$_3$ |
| 475 | CH$_2$CH(CH$_3$)$_2$ | H | F |
| 476 | CH$_2$CH(CH$_3$)$_2$ | H | Cl |
| 477 | CH$_2$CH(CH$_3$)$_2$ | H | Br |
| 478 | CH$_2$CH(CH$_3$)$_2$ | H | I |
| 479 | CH$_2$CH(CH$_3$)$_2$ | H | cC$_3$H$_5$ |
| 480 | CH$_2$CH(CH$_3$)$_2$ | H | CN |
| 481 | CH$_2$CH(CH$_3$)$_2$ | H | CH$_2$CN |
| 482 | CH$_2$CH(CH$_3$)$_2$ | F | H |
| 483 | CH$_2$CH(CH$_3$)$_2$ | F | CH$_3$ |
| 484 | CH$_2$CH(CH$_3$)$_2$ | F | C$_2$H$_5$ |
| 485 | CH$_2$CH(CH$_3$)$_2$ | F | C$_3$H$_7$ |
| 486 | CH$_2$CH(CH$_3$)$_2$ | F | CHF$_2$ |
| 487 | CH$_2$CH(CH$_3$)$_2$ | F | CF$_3$ |
| 488 | CH$_2$CH(CH$_3$)$_2$ | F | F |
| 489 | CH$_2$CH(CH$_3$)$_2$ | F | Cl |
| 490 | CH$_2$CH(CH$_3$)$_2$ | F | Br |
| 491 | CH$_2$CH(CH$_3$)$_2$ | F | I |
| 492 | CH$_2$CH(CH$_3$)$_2$ | F | cC$_3$H$_5$ |
| 493 | CH$_2$CH(CH$_3$)$_2$ | F | CN |
| 494 | CH$_2$CH(CH$_3$)$_2$ | F | CH$_2$CN |
| 495 | CH$_2$CH(CH$_3$)$_2$ | Cl | H |
| 496 | CH$_2$CH(CH$_3$)$_2$ | Cl | CH$_3$ |
| 497 | CH$_2$CH(CH$_3$)$_2$ | Cl | C$_2$H$_5$ |
| 498 | CH$_2$CH(CH$_3$)$_2$ | Cl | C$_3$H$_7$ |
| 499 | CH$_2$CH(CH$_3$)$_2$ | Cl | CHF$_2$ |
| 500 | CH$_2$CH(CH$_3$)$_2$ | Cl | CF$_3$ |
| 501 | CH$_2$CH(CH$_3$)$_2$ | Cl | F |
| 502 | CH$_2$CH(CH$_3$)$_2$ | Cl | Cl |
| 503 | CH$_2$CH(CH$_3$)$_2$ | Cl | Br |
| 504 | CH$_2$CH(CH$_3$)$_2$ | Cl | I |
| 505 | CH$_2$CH(CH$_3$)$_2$ | Cl | cC$_3$H$_5$ |
| 506 | CH$_2$CH(CH$_3$)$_2$ | Cl | CN |
| 507 | CH$_2$CH(CH$_3$)$_2$ | Cl | CH$_2$CN |
| 508 | CH$_2$CH$_2$OCH$_3$ | H | H |
| 509 | CH$_2$CH$_2$OCH$_3$ | H | CH$_3$ |
| 510 | CH$_2$CH$_2$OCH$_3$ | H | C$_2$H$_5$ |
| 511 | CH$_2$CH$_2$OCH$_3$ | H | C$_3$H$_7$ |
| 512 | CH$_2$CH$_2$OCH$_3$ | H | CHF$_2$ |
| 513 | CH$_2$CH$_2$OCH$_3$ | H | CF$_3$ |
| 514 | CH$_2$CH$_2$OCH$_3$ | H | F |
| 515 | CH$_2$CH$_2$OCH$_3$ | H | Cl |
| 516 | CH$_2$CH$_2$OCH$_3$ | H | Br |
| 517 | CH$_2$CH$_2$OCH$_3$ | H | I |
| 518 | CH$_2$CH$_2$OCH$_3$ | H | cC$_3$H$_5$ |
| 519 | CH$_2$CH$_2$OCH$_3$ | H | CN |
| 520 | CH$_2$CH$_2$OCH$_3$ | H | CH$_2$CN |
| 521 | CH$_2$CH$_2$OCH$_3$ | F | H |
| 522 | CH$_2$CH$_2$OCH$_3$ | F | CH$_3$ |
| 523 | CH$_2$CH$_2$OCH$_3$ | F | C$_2$H$_5$ |
| 524 | CH$_2$CH$_2$OCH$_3$ | F | C$_3$H$_7$ |
| 525 | CH$_2$CH$_2$OCH$_3$ | F | CHF$_2$ |
| 526 | CH$_2$CH$_2$OCH$_3$ | F | CF$_3$ |
| 527 | CH$_2$CH$_2$OCH$_3$ | F | F |
| 528 | CH$_2$CH$_2$OCH$_3$ | F | Cl |
| 529 | CH$_2$CH$_2$OCH$_3$ | F | Br |
| 530 | CH$_2$CH$_2$OCH$_3$ | F | I |
| 531 | CH$_2$CH$_2$OCH$_3$ | F | cC$_3$H$_5$ |
| 532 | CH$_2$CH$_2$OCH$_3$ | F | CN |
| 533 | CH$_2$CH$_2$OCH$_3$ | F | CH$_2$CN |
| 534 | CH$_2$CH$_2$OCH$_3$ | Cl | H |
| 535 | CH$_2$CH$_2$OCH$_3$ | Cl | CH$_3$ |
| 536 | CH$_2$CH$_2$OCH$_3$ | Cl | C$_2$H$_5$ |
| 537 | CH$_2$CH$_2$OCH$_3$ | Cl | C$_3$H$_7$ |
| 538 | CH$_2$CH$_2$OCH$_3$ | Cl | CHF$_2$ |
| 539 | CH$_2$CH$_2$OCH$_3$ | Cl | CF$_3$ |
| 540 | CH$_2$CH$_2$OCH$_3$ | Cl | F |
| 541 | CH$_2$CH$_2$OCH$_3$ | Cl | Cl |
| 542 | CH$_2$CH$_2$OCH$_3$ | Cl | Br |
| 543 | CH$_2$CH$_2$OCH$_3$ | Cl | I |
| 544 | CH$_2$CH$_2$OCH$_3$ | Cl | cC$_3$H$_5$ |
| 545 | CH$_2$CH$_2$OCH$_3$ | Cl | CN |
| 546 | CH$_2$CH$_2$OCH$_3$ | Cl | CH$_2$CN |
| 547 | CH$_2$CH$_2$CN | H | H |
| 548 | CH$_2$CH$_2$CN | H | CH$_3$ |
| 549 | CH$_2$CH$_2$CN | H | C$_2$H$_5$ |
| 550 | CH$_2$CH$_2$CN | H | C$_3$H$_7$ |
| 551 | CH$_2$CH$_2$CN | H | CHF$_2$ |
| 552 | CH$_2$CH$_2$CN | H | CF$_3$ |
| 553 | CH$_2$CH$_2$CN | H | F |
| 554 | CH$_2$CH$_2$CN | H | Cl |
| 555 | CH$_2$CH$_2$CN | H | Br |
| 556 | CH$_2$CH$_2$CN | H | I |
| 557 | CH$_2$CH$_2$CN | H | cC$_3$H$_5$ |
| 558 | CH$_2$CH$_2$CN | H | CN |
| 559 | CH$_2$CH$_2$CN | H | CH$_2$CN |
| 560 | CH$_2$CH$_2$CN | F | H |
| 561 | CH$_2$CH$_2$CN | F | CH$_3$ |
| 562 | CH$_2$CH$_2$CN | F | C$_2$H$_5$ |
| 563 | CH$_2$CH$_2$CN | F | C$_3$H$_7$ |
| 564 | CH$_2$CH$_2$CN | F | CHF$_2$ |
| 565 | CH$_2$CH$_2$CN | F | CF$_3$ |
| 566 | CH$_2$CH$_2$CN | F | F |
| 567 | CH$_2$CH$_2$CN | F | Cl |
| 568 | CH$_2$CH$_2$CN | F | Br |
| 569 | CH$_2$CH$_2$CN | F | I |
| 570 | CH$_2$CH$_2$CN | F | cC$_3$H$_5$ |
| 571 | CH$_2$CH$_2$CN | F | CN |
| 572 | CH$_2$CH$_2$CN | F | CH$_2$CN |
| 573 | CH$_2$CH$_2$CN | Cl | H |
| 574 | CH$_2$CH$_2$CN | Cl | CH$_3$ |
| 575 | CH$_2$CH$_2$CN | Cl | C$_2$H$_5$ |
| 576 | CH$_2$CH$_2$CN | Cl | C$_3$H$_7$ |
| 577 | CH$_2$CH$_2$CN | Cl | CHF$_2$ |
| 578 | CH$_2$CH$_2$CN | Cl | CF$_3$ |
| 579 | CH$_2$CH$_2$CN | Cl | F |
| 580 | CH$_2$CH$_2$CN | Cl | Cl |
| 581 | CH$_2$CH$_2$CN | Cl | Br |
| 582 | CH$_2$CH$_2$CN | Cl | I |
| 583 | CH$_2$CH$_2$CN | Cl | cC$_3$H$_5$ |
| 584 | CH$_2$CH$_2$CN | Cl | CN |
| 585 | CH$_2$CH$_2$CN | Cl | CH$_2$CN |
| 586 | CH$_2$CH(CH$_3$)CN | H | H |
| 587 | CH$_2$CH(CH$_3$)CN | H | CH$_3$ |
| 588 | CH$_2$CH(CH$_3$)CN | H | C$_2$H$_5$ |
| 589 | CH$_2$CH(CH$_3$)CN | H | C$_3$H$_7$ |
| 590 | CH$_2$CH(CH$_3$)CN | H | CHF$_2$ |
| 591 | CH$_2$CH(CH$_3$)CN | H | CF$_3$ |
| 592 | CH$_2$CH(CH$_3$)CN | H | F |
| 593 | CH$_2$CH(CH$_3$)CN | H | Cl |
| 594 | CH$_2$CH(CH$_3$)CN | H | Br |
| 595 | CH$_2$CH(CH$_3$)CN | H | I |
| 596 | CH$_2$CH(CH$_3$)CN | H | cC$_3$H$_5$ |
| 597 | CH$_2$CH(CH$_3$)CN | H | CN |
| 598 | CH$_2$CH(CH$_3$)CN | H | CH$_2$CN |
| 599 | CH$_2$CH(CH$_3$)CN | F | H |
| 600 | CH$_2$CH(CH$_3$)CN | F | CH$_3$ |
| 601 | CH$_2$CH(CH$_3$)CN | F | C$_2$H$_5$ |
| 602 | CH$_2$CH(CH$_3$)CN | F | C$_3$H$_7$ |
| 603 | CH$_2$CH(CH$_3$)CN | F | CHF$_2$ |
| 604 | CH$_2$CH(CH$_3$)CN | F | CF$_3$ |

TABLE A-continued

Radicals A2.N ...

| No. | $R^N$ | $R^{A''}$ | $R^{A'}$ |
|---|---|---|---|
| 605 | $CH_2CH(CH_3)CN$ | F | F |
| 606 | $CH_2CH(CH_3)CN$ | F | Cl |
| 607 | $CH_2CH(CH_3)CN$ | F | Br |
| 608 | $CH_2CH(CH_3)CN$ | F | I |
| 609 | $CH_2CH(CH_3)CN$ | F | $cC_3H_5$ |
| 610 | $CH_2CH(CH_3)CN$ | F | CN |
| 611 | $CH_2CH(CH_3)CN$ | F | $CH_2CN$ |
| 612 | $CH_2CH(CH_3)CN$ | Cl | H |
| 613 | $CH_2CH(CH_3)CN$ | Cl | $CH_3$ |
| 614 | $CH_2CH(CH_3)CN$ | Cl | $C_2H_5$ |
| 615 | $CH_2CH(CH_3)CN$ | Cl | $C_3H_7$ |
| 616 | $CH_2CH(CH_3)CN$ | Cl | $CHF_2$ |
| 617 | $CH_2CH(CH_3)CN$ | Cl | $CF_3$ |
| 618 | $CH_2CH(CH_3)CN$ | Cl | F |
| 619 | $CH_2CH(CH_3)CN$ | Cl | Cl |
| 620 | $CH_2CH(CH_3)CN$ | Cl | Br |
| 621 | $CH_2CH(CH_3)CN$ | Cl | I |
| 622 | $CH_2CH(CH_3)CN$ | Cl | $cC_3H_5$ |
| 623 | $CH_2CH(CH_3)CN$ | Cl | CN |
| 624 | $CH_2CH(CH_3)CN$ | Cl | $CH_2CN$ |
| 625 | $CH(CH_3)CH_2CN$ | H | H |
| 626 | $CH(CH_3)CH_2CN$ | H | $CH_3$ |
| 627 | $CH(CH_3)CH_2CN$ | H | $C_2H_5$ |
| 628 | $CH(CH_3)CH_2CN$ | H | $C_3H_7$ |
| 629 | $CH(CH_3)CH_2CN$ | H | $CHF_2$ |
| 630 | $CH(CH_3)CH_2CN$ | H | $CF_3$ |
| 631 | $CH(CH_3)CH_2CN$ | H | F |
| 632 | $CH(CH_3)CH_2CN$ | H | Cl |
| 633 | $CH(CH_3)CH_2CN$ | H | Br |
| 634 | $CH(CH_3)CH_2CN$ | H | I |
| 635 | $CH(CH_3)CH_2CN$ | H | $cC_3H_5$ |
| 636 | $CH(CH_3)CH_2CN$ | H | CN |
| 637 | $CH(CH_3)CH_2CN$ | H | $CH_2CN$ |
| 638 | $CH(CH_3)CH_2CN$ | F | H |
| 639 | $CH(CH_3)CH_2CN$ | F | $CH_3$ |
| 640 | $CH(CH_3)CH_2CN$ | F | $C_2H_5$ |
| 641 | $CH(CH_3)CH_2CN$ | F | $C_3H_7$ |
| 642 | $CH(CH_3)CH_2CN$ | F | $CHF_2$ |
| 643 | $CH(CH_3)CH_2CN$ | F | $CF_3$ |
| 644 | $CH(CH_3)CH_2CN$ | F | F |
| 645 | $CH(CH_3)CH_2CN$ | F | Cl |
| 646 | $CH(CH_3)CH_2CN$ | F | Br |
| 647 | $CH(CH_3)CH_2CN$ | F | I |
| 648 | $CH(CH_3)CH_2CN$ | F | $cC_3H_5$ |
| 649 | $CH(CH_3)CH_2CN$ | F | CN |
| 650 | $CH(CH_3)CH_2CN$ | F | $CH_2CN$ |
| 651 | $CH(CH_3)CH_2CN$ | Cl | H |
| 652 | $CH(CH_3)CH_2CN$ | Cl | $CH_3$ |
| 653 | $CH(CH_3)CH_2CN$ | Cl | $C_2H_5$ |
| 654 | $CH(CH_3)CH_2CN$ | Cl | $C_3H_7$ |
| 655 | $CH(CH_3)CH_2CN$ | Cl | $CHF_2$ |
| 656 | $CH(CH_3)CH_2CN$ | Cl | $CF_3$ |
| 657 | $CH(CH_3)CH_2CN$ | Cl | F |
| 658 | $CH(CH_3)CH_2CN$ | Cl | Cl |
| 659 | $CH(CH_3)CH_2CN$ | Cl | Br |
| 660 | $CH(CH_3)CH_2CN$ | Cl | I |
| 661 | $CH(CH_3)CH_2CN$ | Cl | $cC_3H_5$ |
| 662 | $CH(CH_3)CH_2CN$ | Cl | CN |
| 663 | $CH(CH_3)CH_2CN$ | Cl | $CH_2CN$ |
| 664 | $cC_3H_5$ | H | H |
| 665 | $cC_3H_5$ | H | $CH_3$ |
| 666 | $cC_3H_5$ | H | $C_2H_5$ |
| 667 | $cC_3H_5$ | H | $C_3H_7$ |
| 668 | $cC_3H_5$ | H | $CHF_2$ |
| 669 | $cC_3H_5$ | H | $CF_3$ |
| 670 | $cC_3H_5$ | H | F |
| 671 | $cC_3H_5$ | H | Cl |
| 672 | $cC_3H_5$ | H | Br |
| 673 | $cC_3H_5$ | H | I |
| 674 | $cC_3H_5$ | H | $cC_3H_5$ |
| 675 | $cC_3H_5$ | H | CN |
| 676 | $cC_3H_5$ | H | $CH_2CN$ |
| 677 | $cC_3H_5$ | F | H |
| 678 | $cC_3H_5$ | F | $CH_3$ |
| 679 | $cC_3H_5$ | F | $C_2H_5$ |
| 680 | $cC_3H_5$ | F | $C_3H_7$ |
| 681 | $cC_3H_5$ | F | $CHF_2$ |
| 682 | $cC_3H_5$ | F | $CF_3$ |
| 683 | $cC_3H_5$ | F | F |
| 684 | $cC_3H_5$ | F | Cl |
| 685 | $cC_3H_5$ | F | Br |
| 686 | $cC_3H_5$ | F | I |
| 687 | $cC_3H_5$ | F | $cC_3H_5$ |
| 688 | $cC_3H_5$ | F | CN |
| 689 | $cC_3H_5$ | F | $CH_2CN$ |
| 690 | $cC_3H_5$ | Cl | H |
| 691 | $cC_3H_5$ | Cl | $CH_3$ |
| 692 | $cC_3H_5$ | Cl | $C_2H_5$ |
| 693 | $cC_3H_5$ | Cl | $C_3H_7$ |
| 694 | $cC_3H_5$ | Cl | $CHF_2$ |
| 695 | $cC_3H_5$ | Cl | $CF_3$ |
| 696 | $cC_3H_5$ | Cl | F |
| 697 | $cC_3H_5$ | Cl | Cl |
| 698 | $cC_3H_5$ | Cl | Br |
| 699 | $cC_3H_5$ | Cl | I |
| 700 | $cC_3H_5$ | Cl | $cC_3H_5$ |
| 701 | $cC_3H_5$ | Cl | CN |
| 702 | $cC_3H_5$ | Cl | $CH_2CN$ |
| 703 | $1\text{-}F\text{—}cC_3H_4$ | H | H |
| 704 | $1\text{-}F\text{—}cC_3H_4$ | H | $CH_3$ |
| 705 | $1\text{-}F\text{—}cC_3H_4$ | H | $C_2H_5$ |
| 706 | $1\text{-}F\text{—}cC_3H_4$ | H | $C_3H_7$ |
| 707 | $1\text{-}F\text{—}cC_3H_4$ | H | $CHF_2$ |
| 708 | $1\text{-}F\text{—}cC_3H_4$ | H | $CF_3$ |
| 709 | $1\text{-}F\text{—}cC_3H_4$ | H | F |
| 710 | $1\text{-}F\text{—}cC_3H_4$ | H | Cl |
| 711 | $1\text{-}F\text{—}cC_3H_4$ | H | Br |
| 712 | $1\text{-}F\text{—}cC_3H_4$ | H | I |
| 713 | $1\text{-}F\text{—}cC_3H_4$ | H | $cC_3H_5$ |
| 714 | $1\text{-}F\text{—}cC_3H_4$ | H | CN |
| 715 | $1\text{-}F\text{—}cC_3H_4$ | H | $CH_2CN$ |
| 716 | $1\text{-}F\text{—}cC_3H_4$ | F | H |
| 717 | $1\text{-}F\text{—}cC_3H_4$ | F | $CH_3$ |
| 718 | $1\text{-}F\text{—}cC_3H_4$ | F | $C_2H_5$ |
| 719 | $1\text{-}F\text{—}cC_3H_4$ | F | $C_3H_7$ |
| 720 | $1\text{-}F\text{—}cC_3H_4$ | F | $CHF_2$ |
| 721 | $1\text{-}F\text{—}cC_3H_4$ | F | $CF_3$ |
| 722 | $1\text{-}F\text{—}cC_3H_4$ | F | F |
| 723 | $1\text{-}F\text{—}cC_3H_4$ | F | Cl |
| 724 | $1\text{-}F\text{—}cC_3H_4$ | F | Br |
| 725 | $1\text{-}F\text{—}cC_3H_4$ | F | I |
| 726 | $1\text{-}F\text{—}cC_3H_4$ | F | $cC_3H_5$ |
| 727 | $1\text{-}F\text{—}cC_3H_4$ | F | CN |
| 728 | $1\text{-}F\text{—}cC_3H_4$ | F | $CH_2CN$ |
| 729 | $1\text{-}F\text{—}cC_3H_4$ | Cl | H |
| 730 | $1\text{-}F\text{—}cC_3H_4$ | Cl | $CH_3$ |
| 731 | $1\text{-}F\text{—}cC_3H_4$ | Cl | $C_2H_5$ |
| 732 | $1\text{-}F\text{—}cC_3H_4$ | Cl | $C_3H_7$ |
| 733 | $1\text{-}F\text{—}cC_3H_4$ | Cl | $CHF_2$ |
| 734 | $1\text{-}F\text{—}cC_3H_4$ | Cl | $CF_3$ |
| 735 | $1\text{-}F\text{—}cC_3H_4$ | Cl | F |
| 736 | $1\text{-}F\text{—}cC_3H_4$ | Cl | Cl |
| 737 | $1\text{-}F\text{—}cC_3H_4$ | Cl | Br |
| 738 | $1\text{-}F\text{—}cC_3H_4$ | Cl | I |
| 739 | $1\text{-}F\text{—}cC_3H_4$ | Cl | $cC_3H_5$ |
| 740 | $1\text{-}F\text{—}cC_3H_4$ | Cl | CN |
| 741 | $1\text{-}F\text{—}cC_3H_4$ | Cl | $CH_2CN$ |
| 742 | $1\text{-}Cl\text{—}cC_3H_4$ | H | H |
| 743 | $1\text{-}Cl\text{—}cC_3H_4$ | H | $CH_3$ |
| 744 | $1\text{-}Cl\text{—}cC_3H_4$ | H | $C_2H_5$ |
| 745 | $1\text{-}Cl\text{—}cC_3H_4$ | H | $C_3H_7$ |
| 746 | $1\text{-}Cl\text{—}cC_3H_4$ | H | $CHF_2$ |
| 747 | $1\text{-}Cl\text{—}cC_3H_4$ | H | $CF_3$ |
| 748 | $1\text{-}Cl\text{—}cC_3H_4$ | H | F |
| 749 | $1\text{-}Cl\text{—}cC_3H_4$ | H | Cl |
| 750 | $1\text{-}Cl\text{—}cC_3H_4$ | H | Br |
| 751 | $1\text{-}Cl\text{—}cC_3H_4$ | H | I |
| 752 | $1\text{-}Cl\text{—}cC_3H_4$ | H | $cC_3H_5$ |
| 753 | $1\text{-}Cl\text{—}cC_3H_4$ | H | CN |
| 754 | $1\text{-}Cl\text{—}cC_3H_4$ | H | $CH_2CN$ |
| 755 | $1\text{-}Cl\text{—}cC_3H_4$ | F | H |
| 756 | $1\text{-}Cl\text{—}cC_3H_4$ | F | $CH_3$ |

TABLE A-continued

Radicals A2.N ...

| No. | $R^N$ | $R^{A''}$ | $R^{A'}$ |
|---|---|---|---|
| 757 | 1-Cl—cC$_3$H$_4$ | F | C$_2$H$_5$ |
| 758 | 1-Cl—cC$_3$H$_4$ | F | C$_3$H$_7$ |
| 759 | 1-Cl—cC$_3$H$_4$ | F | CHF$_2$ |
| 760 | 1-Cl—cC$_3$H$_4$ | F | CF$_3$ |
| 761 | 1-Cl—cC$_3$H$_4$ | F | F |
| 762 | 1-Cl—cC$_3$H$_4$ | F | Cl |
| 763 | 1-Cl—cC$_3$H$_4$ | F | Br |
| 764 | 1-Cl—cC$_3$H$_4$ | F | I |
| 765 | 1-Cl—cC$_3$H$_4$ | F | cC$_3$H$_5$ |
| 766 | 1-Cl—cC$_3$H$_4$ | F | CN |
| 767 | 1-Cl—cC$_3$H$_4$ | F | CH$_2$CN |
| 768 | 1-Cl—cC$_3$H$_4$ | Cl | H |
| 769 | 1-Cl—cC$_3$H$_4$ | Cl | CH$_3$ |
| 770 | 1-Cl—cC$_3$H$_4$ | Cl | C$_2$H$_5$ |
| 771 | 1-Cl—cC$_3$H$_4$ | Cl | C$_3$H$_7$ |
| 772 | 1-Cl—cC$_3$H$_4$ | Cl | CHF$_2$ |
| 773 | 1-Cl—cC$_3$H$_4$ | Cl | CF$_3$ |
| 774 | 1-Cl—cC$_3$H$_4$ | Cl | F |
| 775 | 1-Cl—cC$_3$H$_4$ | Cl | Cl |
| 776 | 1-Cl—cC$_3$H$_4$ | Cl | Br |
| 777 | 1-Cl—cC$_3$H$_4$ | Cl | I |
| 778 | 1-Cl—cC$_3$H$_4$ | Cl | cC$_3$H$_5$ |
| 779 | 1-Cl—cC$_3$H$_4$ | Cl | CN |
| 780 | 1-Cl—cC$_3$H$_4$ | Cl | CH$_2$CN |
| 781 | CH$_2$cC$_3$H$_5$ | H | H |
| 782 | CH$_2$cC$_3$H$_5$ | H | CH$_3$ |
| 783 | CH$_2$cC$_3$H$_5$ | H | C$_2$H$_5$ |
| 784 | CH$_2$cC$_3$H$_5$ | H | C$_3$H$_7$ |
| 785 | CH$_2$cC$_3$H$_5$ | H | CHF$_2$ |
| 786 | CH$_2$cC$_3$H$_5$ | H | CF$_3$ |
| 787 | CH$_2$cC$_3$H$_5$ | H | F |
| 788 | CH$_2$cC$_3$H$_5$ | H | Cl |
| 789 | CH$_2$cC$_3$H$_5$ | H | Br |
| 790 | CH$_2$cC$_3$H$_5$ | H | I |
| 791 | CH$_2$cC$_3$H$_5$ | H | cC$_3$H$_5$ |
| 792 | CH$_2$cC$_3$H$_5$ | H | CN |
| 793 | CH$_2$cC$_3$H$_5$ | H | CH$_2$CN |
| 794 | CH$_2$cC$_3$H$_5$ | F | H |
| 795 | CH$_2$cC$_3$H$_5$ | F | CH$_3$ |
| 796 | CH$_2$cC$_3$H$_5$ | F | C$_2$H$_5$ |
| 797 | CH$_2$cC$_3$H$_5$ | F | C$_3$H$_7$ |
| 798 | CH$_2$cC$_3$H$_5$ | F | CHF$_2$ |
| 799 | CH$_2$cC$_3$H$_5$ | F | CF$_3$ |
| 800 | CH$_2$cC$_3$H$_5$ | F | F |
| 801 | CH$_2$cC$_3$H$_5$ | F | Cl |
| 802 | CH$_2$cC$_3$H$_5$ | F | Br |
| 803 | CH$_2$cC$_3$H$_5$ | F | I |
| 804 | CH$_2$cC$_3$H$_5$ | F | cC$_3$H$_5$ |
| 805 | CH$_2$cC$_3$H$_5$ | F | CN |
| 806 | CH$_2$cC$_3$H$_5$ | F | CH$_2$CN |
| 807 | CH$_2$cC$_3$H$_5$ | Cl | H |
| 808 | CH$_2$cC$_3$H$_5$ | Cl | CH$_3$ |
| 809 | CH$_2$cC$_3$H$_5$ | Cl | C$_2$H$_5$ |
| 810 | CH$_2$cC$_3$H$_5$ | Cl | C$_3$H$_7$ |
| 811 | CH$_2$cC$_3$H$_5$ | Cl | CHF$_2$ |
| 812 | CH$_2$cC$_3$H$_5$ | Cl | CF$_3$ |
| 813 | CH$_2$cC$_3$H$_5$ | Cl | F |
| 814 | CH$_2$cC$_3$H$_5$ | Cl | Cl |
| 815 | CH$_2$cC$_3$H$_5$ | Cl | Br |
| 816 | CH$_2$cC$_3$H$_5$ | Cl | I |
| 817 | CH$_2$cC$_3$H$_5$ | Cl | cC$_3$H$_5$ |
| 818 | CH$_2$cC$_3$H$_5$ | Cl | CN |
| 819 | CH$_2$cC$_3$H$_5$ | Cl | CH$_2$CN |
| 820 | CH$_2$(1-F—cC$_3$H$_4$) | H | H |
| 821 | CH$_2$(1-F—cC$_3$H$_4$) | H | CH$_3$ |
| 822 | CH$_2$(1-F—cC$_3$H$_4$) | H | C$_2$H$_5$ |
| 823 | CH$_2$(1-F—cC$_3$H$_4$) | H | C$_3$H$_7$ |
| 824 | CH$_2$(1-F—cC$_3$H$_4$) | H | CHF$_2$ |
| 825 | CH$_2$(1-F—cC$_3$H$_4$) | H | CF$_3$ |
| 826 | CH$_2$(1-F—cC$_3$H$_4$) | H | F |
| 827 | CH$_2$(1-F—cC$_3$H$_4$) | H | Cl |
| 828 | CH$_2$(1-F—cC$_3$H$_4$) | H | Br |
| 829 | CH$_2$(1-F—cC$_3$H$_4$) | H | I |
| 830 | CH$_2$(1-F—cC$_3$H$_4$) | H | cC$_3$H$_5$ |
| 831 | CH$_2$(1-F—cC$_3$H$_4$) | H | CN |
| 832 | CH$_2$(1-F—cC$_3$H$_4$) | H | CH$_2$CN |
| 833 | CH$_2$(1-F—cC$_3$H$_4$) | F | H |
| 834 | CH$_2$(1-F—cC$_3$H$_4$) | F | CH$_3$ |
| 835 | CH$_2$(1-F—cC$_3$H$_4$) | F | C$_2$H$_5$ |
| 836 | CH$_2$(1-F—cC$_3$H$_4$) | F | C$_3$H$_7$ |
| 837 | CH$_2$(1-F—cC$_3$H$_4$) | F | CHF$_2$ |
| 838 | CH$_2$(1-F—cC$_3$H$_4$) | F | CF$_3$ |
| 839 | CH$_2$(1-F—cC$_3$H$_4$) | F | F |
| 840 | CH$_2$(1-F—cC$_3$H$_4$) | F | Cl |
| 841 | CH$_2$(1-F—cC$_3$H$_4$) | F | Br |
| 842 | CH$_2$(1-F—cC$_3$H$_4$) | F | I |
| 843 | CH$_2$(1-F—cC$_3$H$_4$) | F | cC$_3$H$_5$ |
| 844 | CH$_2$(1-F—cC$_3$H$_4$) | F | CN |
| 845 | CH$_2$(1-F—cC$_3$H$_4$) | F | CH$_2$CN |
| 846 | CH$_2$(1-F—cC$_3$H$_4$) | Cl | H |
| 847 | CH$_2$(1-F—cC$_3$H$_4$) | Cl | CH$_3$ |
| 848 | CH$_2$(1-F—cC$_3$H$_4$) | Cl | C$_2$H$_5$ |
| 849 | CH$_2$(1-F—cC$_3$H$_4$) | Cl | C$_3$H$_7$ |
| 850 | CH$_2$(1-F—cC$_3$H$_4$) | Cl | CHF$_2$ |
| 851 | CH$_2$(1-F—cC$_3$H$_4$) | Cl | CF$_3$ |
| 852 | CH$_2$(1-F—cC$_3$H$_4$) | Cl | F |
| 853 | CH$_2$(1-F—cC$_3$H$_4$) | Cl | Cl |
| 854 | CH$_2$(1-F—cC$_3$H$_4$) | Cl | Br |
| 855 | CH$_2$(1-F—cC$_3$H$_4$) | Cl | I |
| 856 | CH$_2$(1-F—cC$_3$H$_4$) | Cl | cC$_3$H$_5$ |
| 857 | CH$_2$(1-F—cC$_3$H$_4$) | Cl | CN |
| 858 | CH$_2$(1-F—cC$_3$H$_4$) | Cl | CH$_2$CN |
| 859 | CH$_2$(1-Cl—cC$_3$H$_4$) | H | H |
| 860 | CH$_2$(1-Cl—cC$_3$H$_4$) | H | CH$_3$ |
| 861 | CH$_2$(1-Cl—cC$_3$H$_4$) | H | C$_2$H$_5$ |
| 862 | CH$_2$(1-Cl—cC$_3$H$_4$) | H | C$_3$H$_7$ |
| 863 | CH$_2$(1-Cl—cC$_3$H$_4$) | H | CHF$_2$ |
| 864 | CH$_2$(1-Cl—cC$_3$H$_4$) | H | CF$_3$ |
| 865 | CH$_2$(1-Cl—cC$_3$H$_4$) | H | F |
| 866 | CH$_2$(1-Cl—cC$_3$H$_4$) | H | Cl |
| 867 | CH$_2$(1-Cl—cC$_3$H$_4$) | H | Br |
| 868 | CH$_2$(1-Cl—cC$_3$H$_4$) | H | I |
| 869 | CH$_2$(1-Cl—cC$_3$H$_4$) | H | cC$_3$H$_5$ |
| 870 | CH$_2$(1-Cl—cC$_3$H$_4$) | H | CN |
| 871 | CH$_2$(1-Cl—cC$_3$H$_4$) | H | CH$_2$CN |
| 872 | CH$_2$(1-Cl—cC$_3$H$_4$) | F | H |
| 873 | CH$_2$(1-Cl—cC$_3$H$_4$) | F | CH$_3$ |
| 874 | CH$_2$(1-Cl—cC$_3$H$_4$) | F | C$_2$H$_5$ |
| 875 | CH$_2$(1-Cl—cC$_3$H$_4$) | F | C$_3$H$_7$ |
| 876 | CH$_2$(1-Cl—cC$_3$H$_4$) | F | CHF$_2$ |
| 877 | CH$_2$(1-Cl—cC$_3$H$_4$) | F | CF$_3$ |
| 878 | CH$_2$(1-Cl—cC$_3$H$_4$) | F | F |
| 879 | CH$_2$(1-Cl—cC$_3$H$_4$) | F | Cl |
| 880 | CH$_2$(1-Cl—cC$_3$H$_4$) | F | Br |
| 881 | CH$_2$(1-Cl—cC$_3$H$_4$) | F | I |
| 882 | CH$_2$(1-Cl—cC$_3$H$_4$) | F | cC$_3$H$_5$ |
| 883 | CH$_2$(1-Cl—cC$_3$H$_4$) | F | CN |
| 884 | CH$_2$(1-Cl—cC$_3$H$_4$) | F | CH$_2$CN |
| 885 | CH$_2$(1-Cl—cC$_3$H$_4$) | Cl | H |
| 886 | CH$_2$(1-Cl—cC$_3$H$_4$) | Cl | CH$_3$ |
| 887 | CH$_2$(1-Cl—cC$_3$H$_4$) | Cl | C$_2$H$_5$ |
| 888 | CH$_2$(1-Cl—cC$_3$H$_4$) | Cl | C$_3$H$_7$ |
| 889 | CH$_2$(1-Cl—cC$_3$H$_4$) | Cl | CHF$_2$ |
| 890 | CH$_2$(1-Cl—cC$_3$H$_4$) | Cl | CF$_3$ |
| 891 | CH$_2$(1-Cl—cC$_3$H$_4$) | Cl | F |
| 892 | CH$_2$(1-Cl—cC$_3$H$_4$) | Cl | Cl |
| 893 | CH$_2$(1-Cl—cC$_3$H$_4$) | Cl | Br |
| 894 | CH$_2$(1-Cl—cC$_3$H$_4$) | Cl | I |
| 895 | CH$_2$(1-Cl—cC$_3$H$_4$) | Cl | cC$_3$H$_5$ |
| 896 | CH$_2$(1-Cl—cC$_3$H$_4$) | Cl | CN |
| 897 | CH$_2$(1-Cl—cC$_3$H$_4$) | Cl | CH$_2$CN |
| 898 | CH$_2$(1-CF$_3$—cC$_3$H$_4$) | H | H |
| 899 | CH$_2$(1-CF$_3$—cC$_3$H$_4$) | H | CH$_3$ |
| 900 | CH$_2$(1-CF$_3$—cC$_3$H$_4$) | H | C$_2$H$_5$ |
| 901 | CH$_2$(1-CF$_3$—cC$_3$H$_4$) | H | C$_3$H$_7$ |
| 902 | CH$_2$(1-CF$_3$—cC$_3$H$_4$) | H | CHF$_2$ |
| 903 | CH$_2$(1-CF$_3$—cC$_3$H$_4$) | H | CF$_3$ |
| 904 | CH$_2$(1-CF$_3$—cC$_3$H$_4$) | H | F |
| 905 | CH$_2$(1-CF$_3$—cC$_3$H$_4$) | H | Cl |
| 906 | CH$_2$(1-CF$_3$—cC$_3$H$_4$) | H | Br |
| 907 | CH$_2$(1-CF$_3$—cC$_3$H$_4$) | H | I |
| 908 | CH$_2$(1-CF$_3$—cC$_3$H$_4$) | H | cC$_3$H$_5$ |

TABLE A-continued

Radicals A2.N ...

| No. | $R^N$ | $R^{A''}$ | $R^{A'}$ |
|---|---|---|---|
| 909 | $CH_2(1-CF_3-cC_3H_4)$ | H | CN |
| 910 | $CH_2(1-CF_3-cC_3H_4)$ | H | $CH_2CN$ |
| 911 | $CH_2(1-CF_3-cC_3H_4)$ | F | H |
| 912 | $CH_2(1-CF_3-cC_3H_4)$ | F | $CH_3$ |
| 913 | $CH_2(1-CF_3-cC_3H_4)$ | F | $C_2H_5$ |
| 914 | $CH_2(1-CF_3-cC_3H_4)$ | F | $C_3H_7$ |
| 915 | $CH_2(1-CF_3-cC_3H_4)$ | F | $CHF_2$ |
| 916 | $CH_2(1-CF_3-cC_3H_4)$ | F | $CF_3$ |
| 917 | $CH_2(1-CF_3-cC_3H_4)$ | F | F |
| 918 | $CH_2(1-CF_3-cC_3H_4)$ | F | Cl |
| 919 | $CH_2(1-CF_3-cC_3H_4)$ | F | Br |
| 920 | $CH_2(1-CF_3-cC_3H_4)$ | F | I |
| 921 | $CH_2(1-CF_3-cC_3H_4)$ | F | $cC_3H_5$ |
| 922 | $CH_2(1-CF_3-cC_3H_4)$ | F | CN |
| 923 | $CH_2(1-CF_3-cC_3H_4)$ | F | $CH_2CN$ |
| 924 | $CH_2(1-CF_3-cC_3H_4)$ | Cl | H |
| 925 | $CH_2(1-CF_3-cC_3H_4)$ | Cl | $CH_3$ |
| 926 | $CH_2(1-CF_3-cC_3H_4)$ | Cl | $C_2H_5$ |
| 927 | $CH_2(1-CF_3-cC_3H_4)$ | Cl | $C_3H_7$ |
| 928 | $CH_2(1-CF_3-cC_3H_4)$ | Cl | $CHF_2$ |
| 929 | $CH_2(1-CF_3-cC_3H_4)$ | Cl | $CF_3$ |
| 930 | $CH_2(1-CF_3-cC_3H_4)$ | Cl | F |
| 931 | $CH_2(1-CF_3-cC_3H_4)$ | Cl | Cl |
| 932 | $CH_2(1-CF_3-cC_3H_4)$ | Cl | Br |
| 933 | $CH_2(1-CF_3-cC_3H_4)$ | Cl | I |
| 934 | $CH_2(1-CF_3-cC_3H_4)$ | Cl | $cC_3H_5$ |
| 935 | $CH_2(1-CF_3-cC_3H_4)$ | Cl | CN |
| 936 | $CH_2(1-CF_3-cC_3H_4)$ | Cl | $CH_2CN$ |
| 937 | $CH_2(1-CN-cC_3H_4)$ | H | H |
| 938 | $CH_2(1-CN-cC_3H_4)$ | H | $CH_3$ |
| 939 | $CH_2(1-CN-cC_3H_4)$ | H | $C_2H_5$ |
| 940 | $CH_2(1-CN-cC_3H_4)$ | H | $C_3H_7$ |
| 941 | $CH_2(1-CN-cC_3H_4)$ | H | $CHF_2$ |
| 942 | $CH_2(1-CN-cC_3H_4)$ | H | $CF_3$ |
| 943 | $CH_2(1-CN-cC_3H_4)$ | H | F |
| 944 | $CH_2(1-CN-cC_3H_4)$ | H | Cl |
| 945 | $CH_2(1-CN-cC_3H_4)$ | H | Br |
| 946 | $CH_2(1-CN-cC_3H_4)$ | H | I |
| 947 | $CH_2(1-CN-cC_3H_4)$ | H | $cC_3H_5$ |
| 948 | $CH_2(1-CN-cC_3H_4)$ | H | CN |
| 949 | $CH_2(1-CN-cC_3H_4)$ | H | $CH_2CN$ |
| 950 | $CH_2(1-CN-cC_3H_4)$ | F | H |
| 951 | $CH_2(1-CN-cC_3H_4)$ | F | $CH_3$ |
| 952 | $CH_2(1-CN-cC_3H_4)$ | F | $C_2H_5$ |
| 953 | $CH_2(1-CN-cC_3H_4)$ | F | $C_3H_7$ |
| 954 | $CH_2(1-CN-cC_3H_4)$ | F | $CHF_2$ |
| 955 | $CH_2(1-CN-cC_3H_4)$ | F | $CF_3$ |
| 956 | $CH_2(1-CN-cC_3H_4)$ | F | F |
| 957 | $CH_2(1-CN-cC_3H_4)$ | F | Cl |
| 958 | $CH_2(1-CN-cC_3H_4)$ | F | Br |
| 959 | $CH_2(1-CN-cC_3H_4)$ | F | I |
| 960 | $CH_2(1-CN-cC_3H_4)$ | F | $cC_3H_5$ |
| 961 | $CH_2(1-CN-cC_3H_4)$ | F | CN |
| 962 | $CH_2(1-CN-cC_3H_4)$ | F | $CH_2CN$ |
| 963 | $CH_2(1-CN-cC_3H_4)$ | Cl | H |
| 964 | $CH_2(1-CN-cC_3H_4)$ | Cl | $CH_3$ |
| 965 | $CH_2(1-CN-cC_3H_4)$ | Cl | $C_2H_5$ |
| 966 | $CH_2(1-CN-cC_3H_4)$ | Cl | $C_3H_7$ |
| 967 | $CH_2(1-CN-cC_3H_4)$ | Cl | $CHF_2$ |
| 968 | $CH_2(1-CN-cC_3H_4)$ | Cl | $CF_3$ |
| 969 | $CH_2(1-CN-cC_3H_4)$ | Cl | F |
| 970 | $CH_2(1-CN-cC_3H_4)$ | Cl | Cl |
| 971 | $CH_2(1-CN-cC_3H_4)$ | Cl | Br |
| 972 | $CH_2(1-CN-cC_3H_4)$ | Cl | I |
| 973 | $CH_2(1-CN-cC_3H_4)$ | Cl | $cC_3H_5$ |
| 974 | $CH_2(1-CN-cC_3H_4)$ | Cl | CN |
| 975 | $CH_2(1-CN-cC_3H_4)$ | Cl | $CH_2CN$ |
| 976 | $CH_2(2,2-Cl_2-cC_3H_3)$ | H | H |
| 977 | $CH_2(2,2-Cl_2-cC_3H_3)$ | H | $CH_3$ |
| 978 | $CH_2(2,2-Cl_2-cC_3H_3)$ | H | $C_2H_5$ |
| 979 | $CH_2(2,2-Cl_2-cC_3H_3)$ | H | $C_3H_7$ |
| 980 | $CH_2(2,2-Cl_2-cC_3H_3)$ | H | $CHF_2$ |
| 981 | $CH_2(2,2-Cl_2-cC_3H_3)$ | H | $CF_3$ |
| 982 | $CH_2(2,2-Cl_2-cC_3H_3)$ | H | F |
| 983 | $CH_2(2,2-Cl_2-cC_3H_3)$ | H | Cl |
| 984 | $CH_2(2,2-Cl_2-cC_3H_3)$ | H | Br |
| 985 | $CH_2(2,2-Cl_2-cC_3H_3)$ | H | I |
| 986 | $CH_2(2,2-Cl_2-cC_3H_3)$ | H | $cC_3H_5$ |
| 987 | $CH_2(2,2-Cl_2-cC_3H_3)$ | H | CN |
| 988 | $CH_2(2,2-Cl_2-cC_3H_3)$ | H | $CH_2CN$ |
| 989 | $CH_2(2,2-Cl_2-cC_3H_3)$ | F | H |
| 990 | $CH_2(2,2-Cl_2-cC_3H_3)$ | F | $CH_3$ |
| 991 | $CH_2(2,2-Cl_2-cC_3H_3)$ | F | $C_2H_5$ |
| 992 | $CH_2(2,2-Cl_2-cC_3H_3)$ | F | $C_3H_7$ |
| 993 | $CH_2(2,2-Cl_2-cC_3H_3)$ | F | $CHF_2$ |
| 994 | $CH_2(2,2-Cl_2-cC_3H_3)$ | F | $CF_3$ |
| 995 | $CH_2(2,2-Cl_2-cC_3H_3)$ | F | F |
| 996 | $CH_2(2,2-Cl_2-cC_3H_3)$ | F | Cl |
| 997 | $CH_2(2,2-Cl_2-cC_3H_3)$ | F | Br |
| 998 | $CH_2(2,2-Cl_2-cC_3H_3)$ | F | I |
| 999 | $CH_2(2,2-Cl_2-cC_3H_3)$ | F | $cC_3H_5$ |
| 1000 | $CH_2(2,2-Cl_2-cC_3H_3)$ | F | CN |
| 1001 | $CH_2(2,2-Cl_2-cC_3H_3)$ | F | $CH_2CN$ |
| 1002 | $CH_2(2,2-Cl_2-cC_3H_3)$ | Cl | H |
| 1003 | $CH_2(2,2-Cl_2-cC_3H_3)$ | Cl | $CH_3$ |
| 1004 | $CH_2(2,2-Cl_2-cC_3H_3)$ | Cl | $C_2H_5$ |
| 1005 | $CH_2(2,2-Cl_2-cC_3H_3)$ | Cl | $C_3H_7$ |
| 1006 | $CH_2(2,2-Cl_2-cC_3H_3)$ | Cl | $CHF_2$ |
| 1007 | $CH_2(2,2-Cl_2-cC_3H_3)$ | Cl | $CF_3$ |
| 1008 | $CH_2(2,2-Cl_2-cC_3H_3)$ | Cl | F |
| 1009 | $CH_2(2,2-Cl_2-cC_3H_3)$ | Cl | Cl |
| 1010 | $CH_2(2,2-Cl_2-cC_3H_3)$ | Cl | Br |
| 1011 | $CH_2(2,2-Cl_2-cC_3H_3)$ | Cl | I |
| 1012 | $CH_2(2,2-Cl_2-cC_3H_3)$ | Cl | $cC_3H_5$ |
| 1013 | $CH_2(2,2-Cl_2-cC_3H_3)$ | Cl | CN |
| 1014 | $CH_2(2,2-Cl_2-cC_3H_3)$ | Cl | $CH_2CN$ |

$C_3H_7$ = n-propyl
$cC_3H_5$ = cyclopropyl

Very preferred embodiments of the present invention relate to the compounds of formula I, in particular of formula I1, where A is one of preferred radicals A2 listed in table A.

Each individual line of table A constitutes a preferred radical A2 according to the present invention.

Within the group of radicals A2 listed in table A, a very preferred subgroup relates to the radicals A2 wherein $R^{A''}$ in table A is H.

Preferred radicals A2 are also the radicals of the type A2.N1bx

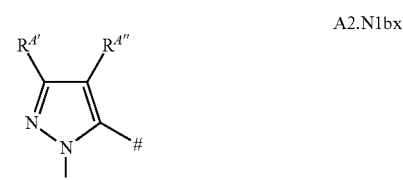

A2.N1bx where # denotes the point of attachment to the remainder of the compound of formula I, $R^N$ is as defined herein, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

Examples of radicals A2.N1bx are the radicals of the types A2.N1bx numbered A2.N1b1 to A2.N1b1014 wherein # denotes the point of attachment to the remainder of the compound of formula I, $R^N$, $R^{A'}$ and $R^{A''}$ are represented by each line of the above Table A.

Preferred radicals A2 are also the radicals of the type A2.N1cx

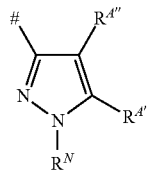

A2.N1cx where # denotes the point of attachment to the remainder of the compound of formula I, $R^N$ is as defined herein, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

Examples of radicals A2.N1cx are the radicals of the types A2.N1cx numbered A2.N1c1 to A2.N1c1014 wherein # denotes the point of attachment to the remainder of the compound of formula I, $R^N$, $R^{A'}$ and $R^{A''}$ are represented by each line of the above Table A.

Particular embodiments of radicals A2 are also the radicals of the types A2.Ox and A2.Oax respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

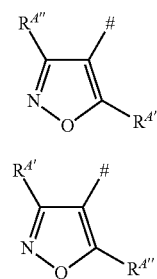

A2.Ox

A2.Oax

Examples of radicals A2.Ox and A2.Oax respectively are the radicals A2.O1 to A2.O169 and A2.Oa1 to A2.Oa169 wherein # denotes the point of attachment to the remainder of the compound of formula I, $R^{A'}$ and $R^{A''}$ are represented by each line of the following Table $R^A$:

Particular embodiments of radicals A2 are also the radicals of the types A2.O1bx and A2.O2bx respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

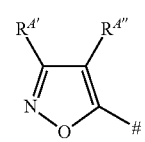

A2.O1bx

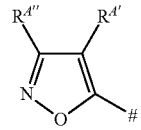

A2.O2bx

Examples of radicals of the types A2.O1bx and A2.O2bx respectively are the radicals A2.O1b1 to A2.O1b169 and A2.O2b1 to A2.O2b169 wherein # denotes the point of attachment to the remainder of the compound of formula I, $R^{A'}$ and $R^{A''}$ are represented by each line of the following Table $R^A$:

Particular embodiments of radicals A2 are also the radicals of the types A2.O1cx and A2.O2cx respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

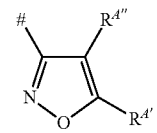

A2.O1cx

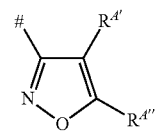

A2.O2cx

Examples of radicals of the types A2.O1cx and A2.O2cx respectively are the radicals A2.O1c1 to A2.O1b169 and A2.O2c1 to A2.O2c169 wherein # denotes the point of attachment to the remainder of the compound of formula I, $R^{A'}$ and $R^{A''}$ are represented by each line of the following Table $R^A$.

Particular embodiments of radicals A2 are also the radicals of the types A2.Sx and A2.Sax respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

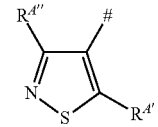

A2.Sx

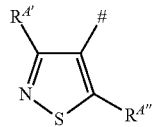

A2.Sax

Examples of radicals of the types A2.Sx and A2.Sax respectively are the radicals A2.S1 to A2.S169 and A2.Sa1 to A2.Sa169 wherein # denotes the point of attachment to the remainder of the compound of formula I, $R^{A'}$ and $R^{A''}$ are represented by each line of the following Table $R^A$.

Particular embodiments of radicals A2 are also the radicals of the types A2.S1bx and A2.S2bx respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

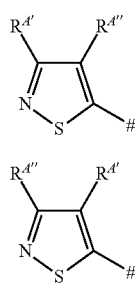

A2.S1bx

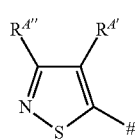

A2.S2bx

Examples of radicals of the types A2.S1 bx and A2.S2bx respectively are the radicals A2.S1b1 to A2.S1b169 and A2.S2b1 to A2.S2b169 wherein # denotes the point of attachment to the remainder of the compound of formula I, $R^{A'}$ and $R^{A''}$ are represented by each line of the following Table $R^A$.

Particular embodiments of radicals A2 are also the radicals of the types A2.S1cx and A2.S2cx respectively, where # denotes the point of attachment to the remainder of the compound of formula I, $R^{A'}$ is hydrogen or has one of the meanings given for $R^A$, and where $R^{A''}$ is hydrogen or has one of the meanings given for $R^A$. In particular $R^{A'}$ is hydrogen or has one of the preferred meanings of $R^A$. In particular $R^{A''}$ is hydrogen or has one of the preferred meanings of $R^A$.

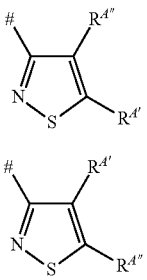

A2.S1cx

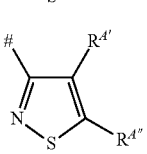

A2.S2cx

Examples of radicals of the types A2.S1cx and A2.S2cx respectively numbered A2.S1c1 to A2.S1c169 and A2.S2c1 to A2.S2c169 wherein # denotes the point of attachment to the remainder of the compound of formula I, $R^{A'}$ and $R^{A''}$ are represented by each line of the following Table $R^A$:

TABLE $R^A$

| Line | $R^{A'}$ | $R^{A''}$ |
| --- | --- | --- |
| 1 | H | H |
| 2 | $CH_3$ | H |
| 3 | $CH_2CH_3$ | H |
| 4 | $CH_2CH_2CH_3$ | H |
| 5 | $CHF_2$ | H |
| 6 | $CF_3$ | H |
| 7 | F | H |
| 8 | Cl | H |
| 9 | Br | H |
| 10 | I | H |
| 11 | $cC_3H_5$ | H |
| 12 | CN | H |
| 13 | $CH_2CN$ | H |
| 14 | H | $CH_3$ |
| 15 | $CH_3$ | $CH_3$ |
| 16 | $CH_2CH_3$ | $CH_3$ |
| 17 | $CH_2CH_2CH_3$ | $CH_3$ |
| 18 | $CHF_2$ | $CH_3$ |
| 19 | $CF_3$ | $CH_3$ |
| 20 | F | $CH_3$ |
| 21 | Cl | $CH_3$ |
| 22 | Br | $CH_3$ |
| 23 | I | $CH_3$ |
| 24 | $cC_3H_5$ | $CH_3$ |
| 25 | CN | $CH_3$ |
| 26 | $CH_2CN$ | $CH_3$ |
| 27 | H | $CH_2CH_3$ |
| 28 | $CH_3$ | $CH_2CH_3$ |
| 29 | $CH_2CH_3$ | $CH_2CH_3$ |
| 30 | $CH_2CH_2CH_3$ | $CH_2CH_3$ |
| 31 | $CHF_2$ | $CH_2CH_3$ |
| 32 | $CF_3$ | $CH_2CH_3$ |
| 33 | F | $CH_2CH_3$ |
| 34 | Cl | $CH_2CH_3$ |
| 35 | Br | $CH_2CH_3$ |
| 36 | I | $CH_2CH_3$ |
| 37 | $cC_3H_5$ | $CH_2CH_3$ |
| 38 | CN | $CH_2CH_3$ |
| 39 | $CH_2CN$ | $CH_2CH_3$ |
| 40 | H | $CH_2CH_2CH_3$ |
| 41 | $CH_3$ | $CH_2CH_2CH_3$ |
| 42 | $CH_2CH_3$ | $CH_2CH_2CH_3$ |
| 43 | $CH_2CH_2CH_3$ | $CH_2CH_2CH_3$ |
| 44 | $CHF_2$ | $CH_2CH_2CH_3$ |
| 45 | $CF_3$ | $CH_2CH_2CH_3$ |
| 46 | F | $CH_2CH_2CH_3$ |
| 47 | Cl | $CH_2CH_2CH_3$ |
| 48 | Br | $CH_2CH_2CH_3$ |
| 49 | I | $CH_2CH_2CH_3$ |
| 50 | $cC_3H_5$ | $CH_2CH_2CH_3$ |
| 51 | CN | $CH_2CH_2CH_3$ |
| 52 | $CH_2CN$ | $CH_2CH_2CH_3$ |
| 53 | H | $CHF_2$ |
| 54 | $CH_3$ | $CHF_2$ |
| 55 | $CH_2CH_3$ | $CHF_2$ |
| 56 | $CH_2CH_2CH_3$ | $CHF_2$ |
| 57 | $CHF_2$ | $CHF_2$ |
| 58 | $CF_3$ | $CHF_2$ |
| 59 | F | $CHF_2$ |
| 60 | Cl | $CHF_2$ |
| 61 | Br | $CHF_2$ |
| 62 | I | $CHF_2$ |
| 63 | $cC_3H_5$ | $CHF_2$ |
| 64 | CN | $CHF_2$ |
| 65 | $CH_2CN$ | $CHF_2$ |
| 66 | H | $CF_3$ |
| 67 | $CH_3$ | $CF_3$ |
| 68 | $CH_2CH_3$ | $CF_3$ |
| 69 | $CH_2CH_2CH_3$ | $CF_3$ |
| 70 | $CHF_2$ | $CF_3$ |
| 71 | $CF_3$ | $CF_3$ |
| 72 | F | $CF_3$ |
| 73 | Cl | $CF_3$ |
| 74 | Br | $CF_3$ |
| 75 | I | $CF_3$ |
| 76 | $cC_3H_5$ | $CF_3$ |
| 77 | CN | $CF_3$ |
| 78 | $CH_2CN$ | $CF_3$ |
| 79 | H | F |
| 80 | $CH_3$ | F |
| 81 | $CH_2CH_3$ | F |
| 82 | $CH_2CH_2CH_3$ | F |

TABLE R<sup>A</sup>-continued

| Line | R<sup>A'</sup> | R<sup>A"</sup> |
|---|---|---|
| 83 | $CHF_2$ | F |
| 84 | $CF_3$ | F |
| 85 | F | F |
| 86 | Cl | F |
| 87 | Br | F |
| 88 | I | F |
| 89 | $cC_3H_5$ | F |
| 90 | CN | F |
| 91 | $CH_2CN$ | F |
| 92 | H | Cl |
| 93 | $CH_3$ | Cl |
| 94 | $CH_2CH_3$ | Cl |
| 95 | $CH_2CH_2CH_3$ | Cl |
| 96 | $CHF_2$ | Cl |
| 97 | $CF_3$ | Cl |
| 98 | F | Cl |
| 99 | Cl | Cl |
| 100 | Br | Cl |
| 101 | I | Cl |
| 102 | $cC_3H_5$ | Cl |
| 103 | CN | Cl |
| 104 | $CH_2CN$ | Cl |
| 105 | H | Br |
| 106 | $CH_3$ | Br |
| 107 | $CH_2CH_3$ | Br |
| 108 | $CH_2CH_2CH_3$ | Br |
| 109 | $CHF_2$ | Br |
| 110 | $CF_3$ | Br |
| 111 | F | Br |
| 112 | Cl | Br |
| 113 | Br | Br |
| 114 | I | Br |
| 115 | $cC_3H_5$ | Br |
| 116 | CN | Br |
| 117 | $CH_2CN$ | Br |
| 118 | H | I |
| 119 | $CH_3$ | I |
| 120 | $CH_2CH_3$ | I |
| 121 | $CH_2CH_2CH_3$ | I |
| 122 | $CHF_2$ | I |
| 123 | $CF_3$ | I |
| 124 | F | I |
| 125 | Cl | I |
| 126 | Br | I |
| 127 | I | I |
| 128 | $cC_3H_5$ | I |
| 129 | CN | I |
| 130 | $CH_2CN$ | I |
| 131 | H | $cC_3H_5$ |
| 132 | $CH_3$ | $cC_3H_5$ |
| 133 | $CH_2CH_3$ | $cC_3H_5$ |
| 134 | $CH_2CH_2CH_3$ | $cC_3H_5$ |
| 135 | $CHF_2$ | $cC_3H_5$ |
| 136 | $CF_3$ | $cC_3H_5$ |
| 137 | F | $cC_3H_5$ |
| 138 | Cl | $cC_3H_5$ |
| 139 | Br | $cC_3H_5$ |
| 140 | I | $cC_3H_5$ |
| 141 | $cC_3H_5$ | $cC_3H_5$ |
| 142 | CN | $cC_3H_5$ |
| 143 | $CH_2CN$ | $cC_3H_5$ |
| 144 | H | CN |
| 145 | $CH_3$ | CN |
| 146 | $CH_2CH_3$ | CN |
| 147 | $CH_2CH_2CH_3$ | CN |
| 148 | $CHF_2$ | CN |
| 149 | $CF_3$ | CN |
| 150 | F | CN |
| 151 | Cl | CN |
| 152 | Br | CN |
| 153 | I | CN |
| 154 | $cC_3H_5$ | CN |
| 155 | CN | CN |
| 156 | $CH_2CN$ | CN |
| 157 | H | $CH_2CN$ |
| 158 | $CH_3$ | $CH_2CN$ |
| 159 | $CH_2CH_3$ | $CH_2CN$ |
| 160 | $CH_2CH_2CH_3$ | $CH_2CN$ |
| 161 | $CHF_2$ | $CH_2CN$ |
| 162 | $CF_3$ | $CH_2CN$ |
| 163 | F | $CH_2CN$ |
| 164 | Cl | $CH_2CN$ |
| 165 | Br | $CH_2CN$ |
| 166 | I | $CH_2CN$ |
| 167 | $cC_3H_5$ | $CH_2CN$ |
| 168 | CN | $CH_2CN$ |
| 169 | $CH_2CN$ | $CH_2CN$ |

$cC_3H_5$ = cyclopropyl

A further embodiment of the invention relates to compounds of formula I, to the salts and N-oxides thereof and to the methods and uses of such compounds, wherein A is a radical A1.

An embodiment of the invention relates to hetaryl (thio) carboxamide compounds of formula I, to the N-oxides and tautomers thereof and to the salts thereof and to the methods and uses of such compounds, wherein A is a radical A1 and the remaining radicals $R^1$ and X are as here above defined.

Within the embodiment relating to compounds of formula I wherein A is A1, a particularly preferred embodiment relates to compounds wherein Z is $NR^N$. In this embodiment, $R^N$ has preferably one of the preferred or particularly preferred meanings given above in connection with the radical A2, in particular one of the meanings given in lines 1 to 123 of Table $R^N$.

Within the embodiment relating to compounds wherein A is A1, further embodiment relates to compounds wherein Z is O.

Within the embodiment relating to compounds wherein A is A1, further embodiment relates to compounds wherein Z is S.

A further embodiment relates to compounds of formula I, wherein A is A1, wherein X is O and $R^1$ have in particular one of the preferred meanings as defined herein.

Within this preferred embodiment, preference is particularly given to compounds of formula I wherein n is 1.

Among the compounds of formula I, wherein A is A1, a further embodiment relates to compounds of the formula I, wherein X is O, $R^1$ have one of the preferred meanings as defined herein and wherein n is 2.

Among the compounds of formula I, wherein A is A1, preference is given to those compounds, wherein $R^A$ has the meanings as defined in the different embodiments wherein A is A2.

Embodiments of the present invention relate to compounds of formula I wherein A is selected from the following suitable examples of radicals A1.

A further embodiment of the invention relates to compounds of formula I, to the salts and N-oxides thereof and to the methods and uses of such compounds, wherein A is a radical A3.

An embodiment of the invention relates to hetaryl (thio) carboxamide compounds of formula I, to their salts, to their tautomers and N-oxides and to the salts thereof and to the methods and uses of such compounds, wherein A is a radical A3 and the remaining radicals $R^1$ and X are as here above defined.

Within the embodiment relating to compounds of formula I wherein A is A3, a particularly preferred embodiment relates to compounds wherein Z is $NR^N$.

Within the embodiment relating to compounds wherein A is A3, further embodiment relates to compounds wherein Z is O.

Within the embodiment relating to compounds wherein A is A3, further embodiment relates to compounds wherein Z is S.

A further embodiment relates to compounds of formula I, wherein A is A3, wherein X is O and $R^1$ have in particular one of the preferred meanings as defined herein.

Within this preferred embodiment, preference is particularly given to compounds of formula I wherein n is 1.

Among the compounds of formula I, wherein A is A3, a further embodiment relates to compounds of the formula I, wherein X is O, $R^1$ have one of the preferred meanings as defined herein and wherein n is 2.

Among the compounds of formula I, wherein A is A3, preference is given to those compounds, wherein $R^4$ has the meanings as defined in the different embodiments wherein A is A2.

Each group of suitable example of radicals A3 constitutes an embodiment of the invention.

For reason of clarity, when analogy is established between a radical A2 and a radical A3 this should mean that the N atom at position 2 in radical A2 is exchanged with the substituent at position 3 in the radical as represented in the following illustrative scheme:

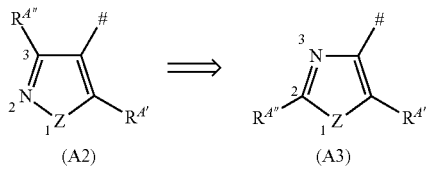

(A2)        (A3)

For a structural analogy, only meanings at positions 2 and 3 are exchanged in the context of the radicals A2 and A3

Analog to the above mentioned radicals of formulae A2.a to A2.z and A2.aa to A2.tt, examples of suitable radicals A3 are the radicals of formulae A3.a, A3.b, A3.c, A3.d, A3.e, A3.f, A3.g, A3.h, A3.i, A3.k, A3.l, A3.m, A3.n, A3.o, A3.p, A3.q, A3.r, A3.s, A3.t, A3.u, A3.v, A3.w, A3.x, A3.y, A3.z, A3.aa, A3.bb, A3.cc, A3.dd, A3.ee, A3.ff, A3.gg, A3.hh, A3.ii, A3.kk, A3.mm, A3.nn, A3.oo, A3.pp, A3.qq, A3.rr, A3.ss, A3.tt, A3.uu and A3.vv, which structures are analog to the structures of the above radicals of formulae A2.a to A2.z and A2.aa to A2.vv and wherein Z is $NR^N$ with $R^N$ being preferably as defined hereabove in the embodiment relating to $R^N$, and wherein $R^N$ is e.g. a radical as defined in one line of table $R^N$ (radicals A3.a1-A3.a123 to A3.z1-A3.z123 and A3.aa123 to A3.vv123).

Analog to the above mentioned radicals of formulae A2O.a to A2O.z and A2O.aa to A2O.tt, further suitable radicals A3 are the radicals of formulae A3O.a, A3O.b, A3O.c, A3O.d, A3O.e, A3O.f, A3O.g, A3O.h, A3O.i, A3O.k, A3O.l, A3O.m, A3O.n, A3O.o, A3O.p, A3O.q, A3O.r, A3O.s, A3O.t, A3O.u, A3O.v, A3O.w, A3O.x, A3O.y, A3O.z, A3O.aa, A3O.bb, A3O.cc, A3O.dd, A3O.ee, A3O.ff, A3O.gg, A3O.hh, A3O.ii, A3O.kk, A3O.mm, A3O.nn, A3O.oo, A3O.pp, A3O.qq, A3O.rr, A3O.ss, A3O.tt, A3O.uu and A3O.vv which structures are analog to the structures of the above radicals of formulae A2O.a to A2O.z and A2O.aa to A2O.vv and wherein Z is O.

Analog to the above mentioned radicals of formulae A2S.a to A2S.z and A2S.aa to A2S.tt, further suitable radicals A3 are the radicals of formulae A3S.a, A3S.b, A3S.c, A3S.d, A3S.e, A3S.f, A3S.g, A3S.h, A3S.i, A3S.k, A3S.l, A3S.m, A3S.n, A3S.o, A3S.p, A3S.q, A3S.r, A3S.s, A3S.t, A3S.u, A3S.v, A3S.w, A3S.x, A3S.y, A3S.z, A3S.aa, A3.bb, A3O.cc, A3S.dd, A3S.ee, A3S.ff, A3S.gg, A3S.hh, A3S.ii, A3S.kk, A3S.mm, A3S.nn, A3S.oo, A3S.pp, A3S.qq, A3S.rr, A3S.ss, A3S.tt, A3S.uu and A3S.vv which structures are analog to the structures of the above radicals of formulae A2S.a to A2S.z and A2S.aa to A2S.vv and wherein Z is S.

Particular preference is given to the radicals of the formulae A3.a, A3.b, A3.c, A3.d, A3.e, A3.f, A3.n, A3.o, A3.q, A3.r, A3.s, A3.t, A3.u, A3.v, A3.w, A3.x, A3.y and A3.z.

Very particular preference is given to radicals of the formulae A3.n, A3.o, A3.q, A3.r, A3.s, A3.t, A3.u, A3.v, A3.w, A3.x, A3.y and A3.z.

Particular preference is also given to the radicals of the formulae A3.aa, A3.bb, A3.cc, A3.dd, A3.ee, A1.ff, A3.gg, A3.hh, A3.kk, A3.ss, A3.tt, A3.uu and A3.vv.

An embodiment of the invention relates to compounds of formula I, to the salts and N-oxides thereof and to the methods and uses of such compounds, wherein A is a radical of the formulae A4, A5, A6 or A7 and the remaining radicals $R^1$ and X are as here above defined.

Within the embodiment relating to compounds of formula I wherein A is a radical of the formulae A4, A5, A6 or A7, a particularly preferred embodiment relates to compounds wherein Z is $NR^N$.

Within the embodiment relating to compounds of formula I wherein A is a radical of the formulae A4, A5, A6 or A7, further embodiment relates to compounds wherein Z is O.

Within the embodiment relating to compounds of formula I wherein A is a radical of the formulae A4, A5, A6 or A7, further embodiment relates to compounds wherein Z is S.

A further embodiment relates to compounds of formula I, wherein A is a radical of the formulae A4, A5, A6 or A7, wherein X is O and $R^1$ have in particular one of the preferred meanings as defined herein.

Within this embodiment, preference is particularly given to compounds of formula I wherein n is 1.

Among the compounds of formula I, wherein A is a radical of the formulae A4, A5, A6 or A7, preference is given to those compounds, wherein $R^4$ has the meanings as defined in the different embodiments wherein A is A2.

Embodiment of the present invention relates to compounds of formula I wherein A is selected from the following suitable example of radicals A4, A5, A6 or A7.

Each group of suitable example of radicals A4, A5, A6 or A7 constitutes an embodiment of the invention.

Particular embodiments of the invention relate to the compounds of formula I, to their salts and N-oxides, where the radical A is a radical of formula A4:

(A4)

wherein # indicates the point of attachment to the remainder of formula I and $R^{A'}$ is as defined herein. Examples of radicals A4 are those, wherein $R^{A'}$ has one of the meanings of line 1 to 13 of Table $R^A$ and wherein Z is $NR^N$ with $R^N$ being as preferably defined hereabove in the embodiment relating to $R^N$, and wherein $R^N$ is e.g. a radical as defined in one line of Table $R^N$.

In analogy to the above cited examples of suitable radicals A4, further suitable radicals A4 are the radicals wherein Z is O.

In analogy to the above cited examples of suitable radicals A4, further suitable radicals A4 are the radicals wherein Z is S.

Particular embodiments of the invention relate to the compounds of formula I, to their salts and N-oxides, where the radical A is a radical of formula A5:

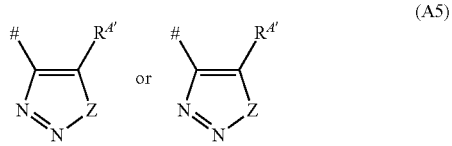

(A5)

wherein # indicates the point of attachment to the remainder of formula I and $R^{A'}$ is as defined herein. Examples of radicals A5 are those, wherein $R^{A'}$ have the each meaning of line 1 to 13 of Table $R^A$ and wherein Z is $NR^N$ with $R^N$ being as preferably defined hereabove in the embodiment relating to $R^N$, and wherein $R^N$ is e.g. a radical as defined in one line of Table $R^N$.

In analogy to the above cited examples of suitable radicals A5, further suitable radicals A5 are the radicals wherein Z is O.

In analogy to the above cited examples of suitable radicals A5, further suitable radicals A5 are the radicals wherein Z is S.

Particular embodiments of the invention relate to the compounds of formula I, to their salts and N-oxides, where the radical A is a radical of formula A6:

(A6)

wherein # indicates the point of attachment to the remainder of formula I and wherein Z and $R^{A'}$ is as defined herein. Examples of radicals A6 are those, wherein $R^{A'}$ has one of the meanings of line 1 to 13 of Table $R^A$ and wherein Z is $NR^N$ with $R^N$ being as preferably defined hereabove in the embodiment relating to $R^N$, and wherein $R^N$ is e.g. a radical as defined in one line of Table $R^N$.

In analogy to the above cited examples of suitable radicals A6, further suitable radicals A6 are the radicals wherein Z is O.

In analogy to the above cited examples of suitable radicals A6, further suitable radicals A6 are the radicals wherein Z is S.

Particular embodiments of the invention relate to the compounds of formula I, to their salts and N-oxides, where the radical A is a radical of formula A7:

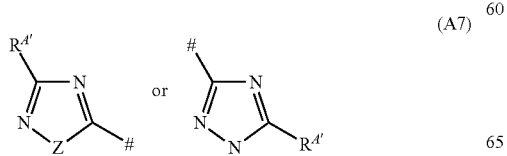

(A7)

wherein # indicates the point of attachment to the remainder of formula I and wherein Z and $R^{A'}$ is as defined herein. Examples of radicals A7 are those, wherein $R^{A'}$ has one of the meanings of line 1 to 13 of Table $R^A$ and wherein Z is $NR^N$ with $R^N$ being as preferably defined hereabove in the embodiment relating to $R^N$, and wherein $R^N$ is e.g. a radical as defined in one line of Table $R^N$ In analogy to the above cited examples of suitable radicals A7, further suitable radicals A7 are the radicals wherein Z is O.

In analogy to the above cited examples of suitable radicals A7, further suitable radicals A7 are the radicals wherein Z is S.

A further embodiment of the invention relates to compounds of formula I, to the salts and N-oxides thereof and to the methods and uses of such compounds, wherein A is a radical A8:

(A8)

wherein # denotes the point of attachment to the remainder of formula I, $Z^1$ is N or C—$R^{Z1}$;
$Z^2$ is N or C—$R^{Z2}$;
$Z^3$ is N or C—$R^{Z3}$;
$Z^4$ is N or C—$R^{Z4}$;
$Z^5$ is N or C—$R^{Z5}$;
provided that one or two of the variables $Z^1$, $Z^2$, $Z^3$, $Z^4$ or $Z^5$ is N;

$R^{Z1}$, $R^{Z5}$ are independently of each other selected from the group consisting of hydrogen, halogen, CN, $NO_2$, $OR^{a1}$, $C(Y)R^{b1}$, $S(O)_mR^{d1}$ with m being 0, 1 or 2, $C_1$-$C_6$-alkyl, $C_2$-$C_6$-alkenyl, $C_2$-$C_6$-alkynyl, wherein the 3 last mentioned radicals may be unsubstituted or may be partially or fully halogenated, $C_1$-$C_5$-alkylen-CN, $C_1$-$C_5$-alkylen-$OR^a$, $C_1$-$C_5$-alkylen-$C(Y)R^b$, $C_1$-$C_5$-alkylen-$C(Y)OR^c$, $C_3$-$C_{10}$-cycloalkyl-$C_1$-$C_5$-alkyl, $C_5$-$C_{10}$-cycloalkenyl-$C_1$-$C_5$-alkyl, 3- to 10-membered heterocyclyl-$C_1$-$C_5$-alkyl, saturated or unsaturated 3 to 10 membered heterocyclyl, $C_3$-$C_{10}$-cycloalkyl and $C_5$-$C_{10}$-cycloalkenyl, wherein cycloalkyl, cycloalkenyl and heterocyclyl in the 6 last mentioned radicals may be unsubstituted or may carry 1, 2, 3, 4 or 5 identical or different substituents $R^y$;

$R^{Z2}$, $R^{Z4}$ are independently of each other selected from the group consisting of hydrogen, halogen, CN, $NO_2$, $OR^{a2}$, $C(Y)R^{b2}$, $S(O)_mR^{d2}$ with m being 0, 1 or 2, $C_1$-$C_{10}$-alkyl, $C_2$-$C_{10}$-alkenyl, $C_2$-$C_{10}$-alkynyl, wherein the 3 last mentioned radicals may be unsubstituted or may be partially or fully halogenated, $C_1$-$C_5$-alkylen-CN, $C_1$-$C_5$-alkylen-$OR^a$, $C_1$-$C_5$-alkylen-$C(Y)R^b$, $C_1$-$C_5$-alkylen-$C(Y)OR^c$, $C_3$-$C_{10}$-cycloalkyl-$C_1$-$C_5$-alkyl, $C_5$-$C_{10}$-cycloalkenyl-$C_1$-$C_5$-alkyl, 3- to 10-membered heterocyclyl-$C_1$-$C_5$-alkyl, saturated 3 to 10 membered heterocyclyl, $C_3$-$C_{10}$-cycloalkyl and $C_5$-$C_{10}$-cycloalkenyl, wherein cycloalkyl, cycloalkenyl and heterocyclyl in the 6 last mentioned radicals may be unsubstituted or may carry 1, 2, 3, 4 or 5 identical or different substituents $R^y$;

$R^{Z3}$ is selected from the group consisting of hydrogen, halogen, CN, $NO_2$, $OR^{a3}$, $C(Y)R^{b3}$, $S(O)_mR^{d3}$ with m being 0, 1 or 2, $C_1$-$C_{10}$-alkyl, $C_2$-$C_{10}$-alkenyl, $C_2$-$C_{10}$-alkynyl, wherein the 3 last mentioned radicals may be unsubstituted or may be partially or fully halogenated, $C_1$-$C_5$-alkylen-CN, $C_1$-$C_5$-alkylen-OR$^a$, $C_1$-$C_5$-alkylen-C(Y)R$^b$, $C_1$-$C_5$-alkylen-C(Y)OR$^c$, $C_3$-$C_{10}$-cycloalkyl-$C_1$-$C_5$-alkyl, $C_5$-$C_{10}$-cycloalkenyl-$C_1$-$C_5$-alkyl, 3- to 10-membered heterocyclyl-$C_1$-$C_5$-alkyl, saturated 3 to 10 membered heterocyclyl, $C_3$-$C_{10}$-cycloalkyl and $C_5$-$C_{10}$-cycloalkenyl, wherein cycloalkyl, cycloalkenyl and heterocyclyl in the 6 last mentioned radicals may be unsubstituted or may carry 1, 2, 3, 4 or 5 identical or different substituents R$^y$;

wherein Y, R$^y$, R$^a$, R$^b$ and R$^c$ are as defined herein and have in particular one of the meanings, and wherein R$^{a1}$, R$^{a2}$ are independently of each other selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

R$^{b1}$, R$^{b2}$ are independently of each other selected from hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, and $C_1$-$C_4$-alkoxy-$C_1$-$C_4$-alkyl;

R$^{d1}$, R$^{d2}$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which are independently of each other selected from halogen, cyano, nitro, $C_1$-$C_4$-alkyl, $C_1$-$C_4$-haloalkyl, $C_1$-$C_4$-alkoxy and $C_1$-$C_4$-haloalkoxy;

R$^{a3}$ has one of the meanings given for R$^a$, except for hydrogen;

R$^{b3}$ has one of the meanings given for R$^b$; and

R$^{d3}$ has one of the meanings given for R$^d$.

An embodiment of the invention relates to hetaryl (thio) carboxamide compounds of formula I, to their salts, to their tautomers and N-oxides and to the salts thereof and to the methods and uses of such compounds, wherein A is a radical A8, which is preferably a pyrimidinyl group, and the remaining radicals R$^1$ and X are as here above defined.

A particular embodiment relates to compounds of formula I, wherein A is A8, wherein X is O and R$^1$ have in particular one of the preferred meanings as defined herein.

Among the compounds of formula I, wherein A is A8, preference is given to those compounds, wherein R$^A$ has the meanings as defined in the different embodiments wherein A is A2.

Among the compounds of formula I wherein A is A8, preference is further given to those compounds, wherein the heterocycle of the radical A 1 or 2 of the variables Z$^1$, Z$^2$, Z$^3$, Z$^4$ or Z$^5$ are N and the remaining groups are C—R$^{Z1}$, C—Z$^2$, C—R$^{Z3}$, C—R$^{Z4}$ or C—R$^{Z5}$. Examples of such compounds are compounds of formulae I or II, wherein the heterocycle A is selected from the radicals pyrazine-2-yl, pyridazine-3-yl, pyridazine-4-yl, pyrimidine-5-yl, pyrimidine-4-yl, pyrimidine-2-yl, 1,2,3-triazine-4-yl, 1,2,3-triazine-5-yl, 1,2,4-triazine-3-yl, 1,2,4-triazine-5-yl and 1,2,4-triazine-6-yl, wherein these radicals are substituted with variables R$^{Z1}$, R$^{Z2}$, R$^{Z3}$, R$^{Z4}$ and R$^{Z5}$ at their respective carbon atoms. Preferably the heterocycle A represents a pyrimidine-5-yl moiety.

Among the compounds of formula I wherein A is A8, preference is further given to those compounds wherein R$^{Z1}$ and R$^{Z5}$, if present, are different from a radical SR$^{d1}$, and wherein R$^{z1}$ and R$^{z5}$ are preferably selected independently of each other from hydrogen, halogen, CN, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_5$-alkylen-CN, $C_1$-$C_5$-alkylen-OR$^a$, $C_1$-$C_5$-alkylen-C(Y)R$^b$ and $C_1$-$C_5$-alkylen-C(Y)OR$^c$, $C_3$-$C_{10}$-cycloalkyl, $C_5$-$C_{10}$-cycloalkenyl, saturated or unsaturated 3- to 10-membered heterocyclyl, $C_3$-$C_{10}$-cycloalkyl-$C_1$-$C_5$-alkyl, $C_5$-$C_{10}$-cycloalkenyl-$C_1$-$C_5$-alkyl, 3- to 10-membered heterocyclyl-$C_1$-$C_5$-alkyl, wherein cycloalkyl, cycloalkenyl and heterocyclyl in the 6 last mentioned radicals may be unsubstituted or may carry 1, 2, 3, 4 or 5 identical or different substituents R$^y$, wherein Y is defined herein and in particular is oxygen, wherein R$^a$, R$^b$ and R$^c$ are as defined herein and in particular are selected independently of each other from the group consisting of hydrogen, $C_1$-$C_4$-alkyl, $C_1$-$C_4$-haloalkyl, $C_1$-$C_4$-alkoxy-$C_1$-$C_4$-alkyl, heterocyclyl-$C_1$-$C_4$-alkyl and hetaryl-$C_1$-$C_4$-alkyl, more preferably from the group consisting of hydrogen, $C_1$-$C_4$-alkyl and $C_1$-$C_4$-alkoxy-$C_1$-$C_2$-alkyl, and most preferably from the group consisting of hydrogen, methyl and ethyl, and wherein the substituents R$^y$ are as defined herein and in particular are selected independently of each other from halogen, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

More preferably R$^{Z1}$ and R$^{Z5}$, if present, are selected independently of each other from hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_3$-alkylen-CN, $C_1$-$C_3$-alkylen-OR$^a$, $C_3$-$C_7$-cycloalkyl, $C_3$-$C_1$-cycloalkyl-$C_1$-$C_3$-alkyl, and 3- to 7-membered saturated heterocyclyl-$C_1$-$C_3$-alkyl, wherein cycloalkyl and heterocyclyl in the 3 last mentioned radicals may be unsubstituted or may carry 1, 2, 3, 4 or 5 identical or different substituents R$^y$, wherein R$^a$ is as defined herein and in particular is selected from the group consisting of hydrogen, $C_1$-$C_4$-alkyl, $C_1$-$C_4$-haloalkyl and $C_1$-$C_4$-alkoxy-$C_1$-$C_2$-alkyl, and specifically from the group consisting of hydrogen, methyl, ethyl, difluormethyl and trifluoromethyl, and wherein the substituents R$^y$ are as defined herein and in particular are selected independently of each other from halogen, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

In a particular preferred embodiment of the invention R$^{Z1}$ and R$^{Z5}$, if present, are selected independently of each other from hydrogen, fluorine, chlorine, bromine, methyl, ethyl, n-propyl, isopropyl, cyclopropyl, isobutyl, cyclopropylmethyl, fluoromethyl, difluoromethyl, trifluoromethyl, 1-fluoroethyl, 2-fluoroethyl, 2,2,2-trifluoroethyl, methoxymethyl, difluoromethoxymethyl, trifluoromethoxymethyl, cyanomethyl, 2-methoxy-1-ethyl, 2-difluoromethoxy-1-ethyl, 2-trifluoromethoxy-1-ethyl, and 2-cyano-1-ethyl.

Among the compounds of formula I preference is further given to those compounds wherein R$^{Z2}$ and R$^{Z4}$, if present, are selected independently of each other from hydrogen, halogen, CN, NO$_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_5$-alkylen-CN, $C_1$-$C_5$-alkylen-OR$^a$, $C_1$-$C_5$-alkylen-C(Y)R$^b$, $C_1$-$C_5$-alkylen-C(Y)OR$^c$, $C_3$-$C_{10}$-cycloalkyl, $C_5$-$C_{10}$-cycloalkenyl, saturated or partially unsaturated 3- to 10-membered heterocyclyl, $C_3$-$C_{10}$-cycloalkyl-$C_1$-$C_5$-alkyl, $C_5$-$C_{10}$-cycloalkenyl-$C_1$-$C_5$-alkyl, saturated or partially unsaturated 3- to 10-membered heterocyclyl-$C_1$-$C_5$-alkyl, wherein cycloalkyl, cycloalkenyl and heterocyclyl in the 6 last mentioned radicals may be unsubstituted or may carry 1, 2, 3, 4 or 5 identical or different substituents $R^y$, wherein Y is defined herein and in particular is oxygen, wherein $R^a$, $R^b$ and $R^c$ are as defined herein and in particular are selected independently of each other from the group consisting of hydrogen, $C_1$-$C_4$-alkyl, $C_1$-$C_4$-haloalkyl, $C_1$-$C_4$-alkoxy-$C_1$-$C_4$-alkyl, heterocyclyl-$C_1$-$C_4$-alkyl and hetaryl-$C_1$-$C_4$-alkyl, more preferably from the group consisting of hydrogen, $C_1$-$C_4$-alkyl and $C_1$-$C_4$-alkoxy-$C_1$-$C_2$-alkyl, and most preferably from the group consisting of hydrogen, methyl and ethyl, and wherein the substituents $R^y$ are as defined herein and in particular are selected independently of each other from halogen, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

More preferably $R^{Z2}$ and $R^{Z4}$, if present, are selected independently of each other from hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_3$-alkylen-CN, $C_1$-$C_3$-alkylen-$OR^a$, $C_3$-$C_7$-cycloalkyl, and 3- to 7-membered saturated heterocyclyl-$C_1$-$C_3$-alkyl, wherein cycloalkyl and heterocyclyl in the 3 last mentioned radicals may be unsubstituted or may carry 1, 2, 3, 4 or 5 identical or different substituents $R^y$, wherein $R^a$ is as defined herein and in particular is selected from the group consisting of hydrogen, $C_1$-$C_4$-alkyl, $C_1$-$C_4$-haloalkyl and $C_1$-$C_4$-alkoxy-$C_1$-$C_2$-alkyl, and specifically from the group consisting of hydrogen, methyl, ethyl, difluormethyl and trifluoromethyl, and wherein the substituents $R^y$ are as defined herein and in particular are selected independently of each other from halogen, $NO_2$, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

In a particular preferred embodiment of the invention $R^{Z2}$ and $R^{Z4}$, if present, are selected independently of each other from hydrogen, fluorine, chlorine, bromine, methyl, ethyl, n-propyl, isopropyl, cyclopropyl, isobutyl, cyclopropylmethyl, fluoromethyl, difluoromethyl, trifluoromethyl, 1-fluoroethyl, 2-fluoroethyl, 2,2,2-trifluoroethyl, methoxymethyl, difluoromethoxymethyl, trifluoromethoxymethyl, cyanomethyl, 2-methoxy-1-ethyl, 2-difluoromethoxy-1-ethyl, 2-trifluoromethoxy-1-ethyl, and 2-cyano-1-ethyl.

Among the compounds of formula I preference is further given to those compounds wherein $R^{Z3}$, if present, is selected from hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-haloalkylsulfinyl, $C_1$-$C_4$-alkylsulfonyl, $C_1$-$C_4$-haloalkylsulfonyl, $C_1$-$C_5$-alkylen-CN, $C_1$-$C_5$-alkylen-$OR^a$, $C_1$-$C_5$-alkylen-C(Y)$R^b$, $C_1$-$C_5$-alkylen-C(Y)$OR^c$, $C_3$-$C_{10}$-cycloalkyl, $C_5$-$C_{10}$-cycloalkenyl, saturated or partially unsaturated 3 to 10 membered heterocyclyl, $C_3$-$C_{10}$-cycloalkyl-$C_1$-$C_5$-alkyl, $C_5$-$C_{10}$-cycloalkenyl-$C_1$-$C_5$-alkyl and 3- to 10-membered heterocyclyl-$C_1$-$C_5$-alkyl, wherein cycloalkyl, cycloalkenyl and heterocyclyl in the 6 last mentioned radicals may be unsubstituted or may carry 1, 2, 3, 4 or 5 identical or different substituents $R^y$, wherein Y is defined herein and in particular is oxygen, wherein $R^a$, $R^b$ and $R^c$ are as defined herein and in particular are selected independently of each other from the group consisting of hydrogen, $C_1$-$C_4$-alkyl, $C_1$-$C_4$-haloalkyl, $C_1$-$C_4$-alkoxy-$C_1$-$C_4$-alkyl, heterocyclyl-$C_1$-$C_4$-alkyl and hetaryl-$C_1$-$C_4$-alkyl, more preferably from the group consisting of hydrogen, $C_1$-$C_4$-alkyl and $C_1$-$C_4$-alkoxy-$C_1$-$C_2$-alkyl, and most preferably from the group consisting of hydrogen, methyl and ethyl, and wherein the substituents $R^y$ are as defined herein and in particular are selected independently of each other from halogen, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

More preferably $R^{Z3}$, if present, is selected from hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_3$-alkylen-CN, $C_1$-$C_3$-alkylen-$OR^a$, $C_3$-$C_7$-cycloalkyl, $C_3$-$C_7$-cycloalkyl-$C_1$-$C_3$-alkyl, and 3- to 7-membered saturated heterocyclyl-$C_1$-$C_3$-alkyl, wherein cycloalkyl and heterocyclyl in the 3 last mentioned radicals may be unsubstituted or may carry 1, 2, 3, 4 or 5 identical or different substituents $R^y$, wherein $R^a$ is as defined herein and in particular is selected from the group consisting of hydrogen, $C_1$-$C_4$-alkyl, $C_1$-$C_4$-haloalkyl and $C_1$-$C_4$-alkoxy-$C_1$-$C_2$-alkyl, and specifically from the group consisting of hydrogen, methyl, ethyl, difluormethyl and trifluoromethyl, and wherein the substituents $R^y$ are as defined herein and in particular are selected independently of each other from halogen, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

In a particular preferred embodiment of the invention $R^{Z3}$, if present, is selected from hydrogen, fluorine, chlorine, bromine, methyl, ethyl, n-propyl, isopropyl, cyclopropyl, isobutyl, cyclopropylmethyl, fluoromethyl, difluoromethyl, trifluoromethyl, 1-fluoroethyl, 2-fluoroethyl, 2,2,2-trifluoroethyl, methoxymethyl, difluoromethoxymethyl, trifluoromethoxymethyl, cyanomethyl, 2-methoxy-1-ethyl, 2-difluoromethoxy-1-ethyl, 2-trifluoromethoxy-1-ethyl, and 2-cyano-1-ethyl.

A particular preferred embodiment of the invention relates to compounds of the formula I, to the salts thereof, the N-oxides thereof and the salts of the N-oxides thereof and to the methods and uses of such compounds, wherein A is a radical A8-1,

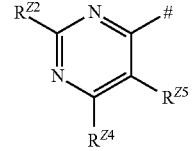

(A8-1)

wherein #, $R^{Z2}$, $R^{Z4}$ and $R^{Z5}$ are as defined herein.

Preferably one or two of the substituents $R^{Z2}$, $R^{Z4}$ and $R^{Z5}$ are hydrogen.

Examples of suitable radicals A8-1 are the radicals of formulae A8-1.1 to A8-1.173, as defined in Table A8-1:

TABLE A8-1

| | |
|---|---|
| (A8-1.1) | PY4 |
| (A8-1.2) | 2-Cl-PY4 |
| (A8-1.3) | 2-Br-PY4 |
| (A8-1.4) | 2-$CH_3$-PY4 |
| (A8-1.5) | 2-$C_2H_5$-PY4 |
| (A8-1.6) | 2-$cC_3H_5$-PY4 |
| (A8-1.7) | 2-$CH(CH_3)_2$-PY4 |
| (A8-1.8) | 2-$CH_2CH(CH_3)_2$-PY4 |
| (A8-1.9) | 2-$CH_2cC_3H_5$-PY4 |
| (A8-1.10) | 2-$CHF_2$-PY4 |
| (A8-1.11) | 2-$CF_3$-PY4 |
| (A8-1.12) | 2-$CH_2CF_3$-PY4 |
| (A8-1.13) | 2-$CH_2OCH_3$-PY4 |
| (A8-1.14) | 2-$CH_2OCHF_2$-PY4 |
| (A8-1.15) | 2-$CH_2OCF_3$-PY4 |
| (A8-1.16) | 2-$CH_2CN$-PY4 |
| (A8-1.17) | 2-$CH_2CH_2OCH_3$-PY4 |
| (A8-1.18) | 2-$OCH_3$-PY4 |
| (A8-1.19) | 2-$OCF_3$-PY4 |
| (A8-1.20) | 5,6-$(CH_3)_2$-PY4 |
| (A8-1.21) | 5-$CH_3$-6-$C_2H_5$-PY4 |

TABLE A8-1-continued

| | |
|---|---|
| (A8-1.22) | 6-CH$_3$-5-C$_2$H$_5$-PY4 |
| (A8-1.23) | 5,6-(C$_2$H$_5$)$_2$-PY4 |
| (A8-1.24) | 2,5,6-(CH$_3$)$_3$-PY4 |
| (A8-1.25) | 2,5-(CH$_3$)$_2$-6-C$_2$H$_5$-PY4 |
| (A8-1.26) | 2,6-(CH$_3$)$_2$-5-C$_2$H$_5$-PY4 |
| (A8-1.27) | 2-CH$_3$-5,6-(C$_2$H$_5$)$_2$-PY4 |
| (A8-1.28) | 2-CF$_3$-5,6-(CH$_3$)$_2$-PY4 |
| (A8-1.29) | 2-CF$_3$-5-CH$_3$-6-C$_2$H$_5$-PY4 |
| (A8-1.30) | 2-CF$_3$-6-CH$_3$-5-C$_2$H$_5$-PY4 |
| (A8-1.31) | 2-CF$_3$-5,6-(C$_2$H$_5$)$_2$-PY4 |
| (A8-1.32) | 2-cC$_3$H$_5$-5,6-(CH$_3$)$_2$-PY4 |
| (A8-1.33) | 2-cC$_3$H$_5$-5-CH$_3$-6-C$_2$H$_5$-PY4 |
| (A8-1.34) | 2-cC$_3$H$_5$-6-CH$_3$-5-C$_2$H$_5$-PY4 |
| (A8-1.35) | 2-cC$_3$H$_5$-5,6-(C$_2$H$_5$)$_2$-PY4 |
| (A8-1.36) | 2-CH(CH$_3$)$_2$-5,6-(CH$_3$)$_2$-PY4 |
| (A8-1.37) | 2-CH(CH$_3$)$_2$-5-CH$_3$-6-C$_2$H$_5$-PY4 |
| (A8-1.38) | 2-CH(CH$_3$)$_2$-6-CH$_3$-5-C$_2$H$_5$-PY4 |
| (A8-1.39) | 2-CH(CH$_3$)$_2$-5,6-(C$_2$H$_5$)$_2$-PY4 |
| (A8-1.40) | 2-CH$_2$CH(CH$_3$)$_2$-5,6-(CH$_3$)$_2$-PY4 |
| (A8-1.41) | 2-CH$_2$CH(CH$_3$)$_2$-5-CH$_3$-6-C$_2$H$_5$-PY4 |
| (A8-1.42) | 2-CH$_2$CH(CH$_3$)$_2$-6-CH$_3$-5-C$_2$H$_5$-PY4 |
| (A8-1.43) | 2-CH$_2$CH(CH$_3$)$_2$-5,6-(C$_2$H$_5$)$_2$-PY4 |
| (A8-1.44) | 2-CH$_2$cC$_3$H$_5$-5,6-(CH$_3$)$_2$-PY4 |
| (A8-1.45) | 2-CH$_2$cC$_3$H$_5$-5-CH$_3$-6-C$_2$H$_5$-PY4 |
| (A8-1.46) | 2-CH$_2$cC$_3$H$_5$-6-CH$_3$-5-C$_2$H$_5$-PY4 |
| (A8-1.47) | 2-CH$_2$cC$_3$H$_5$-5,6-(C$_2$H$_5$)$_2$-PY4 |
| (A8-1.48) | 6-CH$_3$-PY4 |
| (A8-1.49) | 2-CH$_3$-6-CH$_3$-PY4 |
| (A8-1.50) | 2-CF$_3$-6-CH$_3$-PY4 |
| (A8-1.51) | 2-cC$_3$H$_5$-6-CH$_3$-PY4 |
| (A8-1.52) | 2-CH(CH$_3$)$_2$-6-CH$_3$-PY4 |
| (A8-1.53) | 2-CH$_2$CH(CH$_3$)$_2$-6-CH$_3$-PY4 |
| (A8-1.54) | 2-CH$_2$cC$_3$H$_5$-6-CH$_3$-PY4 |
| (A8-1.55) | 6-C$_2$H$_5$-PY4 |
| (A8-1.56) | 2-CH$_3$-6-C$_2$H$_5$-PY4 |
| (A8-1.57) | 2-CF$_3$-6-C$_2$H$_5$-PY4 |
| (A8-1.58) | 2-cC$_3$H$_5$-6-C$_2$H$_5$-PY4 |
| (A8-1.59) | 2-CH(CH$_3$)$_2$-6-C$_2$H$_5$-PY4 |
| (A8-1.60) | 2-CH$_2$CH(CH$_3$)$_2$-6-C$_2$H$_5$-PY4 |
| (A8-1.61) | 2-CH$_2$cC$_3$H$_5$-6-C$_2$H$_5$-PY4 |
| (A8-1.62) | 6-CF$_3$-PY4 |
| (A8-1.63) | 2-CH$_3$-6-CF$_3$-PY4 |
| (A8-1.64) | 2,6-(CF$_3$)$_2$-PY4 |
| (A8-1.65) | 2-cC$_3$H$_5$-6-CF$_3$-PY4 |
| (A8-1.66) | 2-CH(CH$_3$)$_2$-6-CF$_3$-PY4 |
| (A8-1.67) | 2-CH$_2$CH(CH$_3$)$_2$-6-CF$_3$-PY4 |
| (A8-1.68) | 2-CH$_2$cC$_3$H$_5$-6-CF$_3$-PY4 |
| (A8-1.69) | 6-CHF$_2$-PY4 |
| (A8-1.70) | 2-CH$_3$-6-CHF$_2$-PY4 |
| (A8-1.71) | 2-CF$_3$-6-CHF$_2$-PY4 |
| (A8-1.72) | 2-cC$_3$H$_5$-6-CHF$_2$-PY4 |
| (A8-1.73) | 2-CH(CH$_3$)$_2$-6-CHF$_2$-PY4 |
| (A8-1.74) | 2-CH$_2$CH(CH$_3$)$_2$-6-CHF$_2$-PY4 |
| (A8-1.75) | 2-CH$_2$cC$_3$H$_5$-6-CHF$_2$-PY4 |
| (A8-1.76) | 6-CH$_2$CF$_3$-PY4 |
| (A8-1.77) | 6-CH$_2$OCH$_3$-PY4 |
| (A8-1.78) | 6-CH$_2$OCHF$_2$-PY4 |
| (A8-1.79) | 6-CH$_2$OCF$_3$-PY4 |
| (A8-1.80) | 6-CH$_2$CN-PY4 |
| (A8-1.81) | 6-CH$_2$CH$_2$OCH$_3$-PY4 |
| (A8-1.82) | 2-CH$_3$-6-CH$_2$CF$_3$-PY4 |
| (A8-1.83) | 2-CH$_3$-6-CH$_2$OCH$_3$-PY4 |
| (A8-1.84) | 2-CH$_3$-6-CH$_2$OCHF$_2$-PY4 |
| (A8-1.85) | 2-CH$_3$-6-CH$_2$OCF$_3$-PY4 |
| (A8-1.86) | 2-CH$_3$-6-CH$_2$CN-PY4 |
| (A8-1.87) | 2-CH$_3$-6-CH$_2$CH$_2$OCH$_3$-PY4 |
| (A8-1.88) | 2-CF$_3$-6-CH$_2$CF$_3$-PY4 |
| (A8-1.89) | 2-CF$_3$-6-CH$_2$OCH$_3$-PY4 |
| (A8-1.90) | 2-CF$_3$-6-CH$_2$OCHF$_2$-PY4 |
| (A8-1.91) | 2-CF$_3$-6-CH$_2$OCF$_3$-PY4 |
| (A8-1.92) | 2-CF$_3$-6-CH$_2$CN-PY4 |
| (A8-1.93) | 2-CF$_3$-6-CH$_2$CH$_2$OCH$_3$-PY4 |
| (A8-1.94) | 2-cC$_3$H$_5$-6-CH$_2$CF$_3$-PY4 |
| (A8-1.95) | 2-cC$_3$H$_5$-6-CH$_2$OCH$_3$-PY4 |
| (A8-1.96) | 2-cC$_3$H$_5$-6-CH$_2$OCHF$_2$-PY4 |
| (A8-1.97) | 2-cC$_3$H$_5$-6-CH$_2$OCF$_3$-PY4 |
| (A8-1.98) | 2-cC$_3$H$_5$-6-CH$_2$CN-PY4 |
| (A8-1.99) | 2-cC$_3$H$_5$-6-CH$_2$CH$_2$OCH$_3$-PY4 |
| (A8-1.100) | 2-CH(CH$_3$)$_2$-6-CH$_2$CF$_3$-PY4 |
| (A8-1.101) | 2-CH(CH$_3$)$_2$-6-CH$_2$OCH$_3$-PY4 |
| (A8-1.102) | 2-CH(CH$_3$)$_2$-6-CH$_2$OCHF$_2$-PY4 |
| (A8-1.103) | 2-CH(CH$_3$)$_2$-6-CH$_2$OCF$_3$-PY4 |
| (A8-1.104) | 2-CH(CH$_3$)$_2$-6-CH$_2$CN-PY4 |
| (A8-1.105) | 2-CH(CH$_3$)$_2$-6-CH$_2$CH$_2$OCH$_3$-PY4 |
| (A8-1.106) | 2-CH$_2$CH(CH$_3$)$_2$-6-CH$_2$CF$_3$-PY4 |
| (A8-1.107) | 2-CH$_2$CH(CH$_3$)$_2$-6-CH$_2$OCH$_3$-PY4 |
| (A8-1.108) | 2-CH$_2$CH(CH$_3$)$_2$-6-CH$_2$OCHF$_2$-PY4 |
| (A8-1.109) | 2-CH$_2$CH(CH$_3$)$_2$-6-CH$_2$OCF$_3$-PY4 |
| (A8-1.110) | 2-CH$_2$CH(CH$_3$)$_2$-6-CH$_2$CN-PY4 |
| (A8-1.111) | 2-CH$_2$CH(CH$_3$)$_2$-6-CH$_2$CH$_2$OCH$_3$-PY4 |
| (A8-1.112) | 2-CH$_2$cC$_3$H$_5$-6-CH$_2$CF$_3$-PY4 |
| (A8-1.113) | 2-CH$_2$cC$_3$H$_5$-6-CH$_2$OCH$_3$-PY4 |
| (A8-1.114) | 2-CH$_2$cC$_3$H$_5$-6-CH$_2$OCHF$_2$-PY4 |
| (A8-1.115) | 2-CH$_2$cC$_3$H$_5$-6-CH$_2$OCF$_3$-PY4 |
| (A8-1.116) | 2-CH$_2$cC$_3$H$_5$-6-CH$_2$CN-PY4 |
| (A8-1.117) | 2-CH$_2$cC$_3$H$_5$-6-CH$_2$CH$_2$OCH$_3$-PY4 |
| (A8-1.118) | 6-Cl-PY4 |
| (A8-1.119) | 2-CH$_3$-6-Cl-PY4 |
| (A8-1.120) | 2-CF$_3$-6-Cl-PY4 |
| (A8-1.121) | 2-cC$_3$H$_5$-6-Cl-PY4 |
| (A8-1.122) | 2-CH(CH$_3$)$_2$-6-Cl-PY4 |
| (A8-1.123) | 2-CH$_2$CH(CH$_3$)$_2$-6-Cl-PY4 |
| (A8-1.124) | 2-CH$_2$cC$_3$H$_5$-6-Cl-PY4 |
| (A8-1.125) | 6-Br-PY4 |
| (A8-1.126) | 2-CH$_3$-6-Br-PY4 |
| (A8-1.127) | 2-CF$_3$-6-Br-PY4 |
| (A8-1.128) | 2-cC$_3$H$_5$-6-Br-PY4 |
| (A8-1.129) | 2-CH(CH$_3$)$_2$-6-Br-PY4 |
| (A8-1.130) | 2-CH$_2$CH(CH$_3$)$_2$-6-Br-PY4v |
| (A8-1.131) | 2-CH$_2$cC$_3$H$_5$-6-Br-PY4 |
| (A8-1.132) | 6-cC$_3$H$_5$-PY4 |
| (A8-1.133) | 6-CH(CH$_3$)$_2$-PY4 |
| (A8-1.134) | 6-CH$_2$CH(CH$_3$)$_2$-PY4 |
| (A8-1.135) | 6-CH$_2$cC$_3$H$_5$-PY4 |
| (A8-1.136) | 2-CH$_3$-6-cC$_3$H$_5$-PY4 |
| (A8-1.137) | 2-CH$_3$-6-CH(CH$_3$)$_2$-PY4 |
| (A8-1.138) | 2-CH$_3$-6-CH$_2$CH(CH$_3$)$_2$-PY4 |
| (A8-1.139) | 2-CH$_3$-6-CH$_2$cC$_3$H$_5$-PY4 |
| (A8-1.140) | 2-CF$_3$-6-cC$_3$H$_5$-PY4 |
| (A8-1.141) | 2-CF$_3$-6-CH(CH$_3$)$_2$-PY4 |
| (A8-1.142) | 2-CF$_3$-6-CH$_2$CH(CH$_3$)$_2$-PY4 |
| (A8-1.143) | 2-CF$_3$-6-CH$_2$cC$_3$H$_5$-PY4 |
| (A8-1.144) | 2,6-(cC$_3$H$_5$)$_2$-PY4 |
| (A8-1.145) | 2-cC$_3$H$_5$-6-CH(CH$_3$)$_2$-PY4 |
| (A8-1.146) | 2-cC$_3$H$_5$-6-CH$_2$CH(CH$_3$)$_2$-PY4 |
| (A8-1.147) | 2-cC$_3$H$_5$-6-CH$_2$cC$_3$H$_5$-PY4 |
| (A8-1.148) | 2-CH(CH$_3$)$_2$-6-cC$_3$H$_5$-PY4 |
| (A8-1.149) | 2,6-[CH(CH$_3$)$_2$]$_2$-PY4 |
| (A8-1.150) | 2-CH(CH$_3$)$_2$-6-CH$_2$CH(CH$_3$)$_2$-PY4 |
| (A8-1.151) | 2-CH(CH$_3$)$_2$-6-CH$_2$cC$_3$H$_5$-PY4 |
| (A8-1.152) | 2-CH$_2$CH(CH$_3$)$_2$-6-cC$_3$H$_5$-PY4 |
| (A8-1.153) | 2-CH$_2$CH(CH$_3$)$_2$-6-CH(CH$_3$)$_2$-PY4 |
| (A8-1.154) | 2,6-[CH$_2$CH(CH$_3$)$_2$]$_2$-PY4 |
| (A8-1.155) | 2-CH$_2$CH(CH$_3$)$_2$-6-CH$_2$cC$_3$H$_5$-PY4 |
| (A8-1.156) | 2-CH$_2$cC$_3$H$_5$-6-cC$_3$H$_5$-PY4 |
| (A8-1.157) | 2-CH$_2$cC$_3$H$_5$-6-CH(CH$_3$)$_2$-PY4 |
| (A8-1.158) | 2-CH$_2$cC$_3$H$_5$-6-CH$_2$CH(CH$_3$)$_2$-PY4 |
| (A8-1.159) | 2,6-(CH$_2$cC$_3$H$_5$)$_2$-PY4 |
| (A8-1.160) | 6-OCH$_3$-PY4 |
| (A8-1.161) | 2-CH$_3$-6-OCH$_3$-PY4 |
| (A8-1.162) | 2-CF$_3$-6-OCH$_3$-PY4 |
| (A8-1.163) | 2-cC$_3$H$_5$-6-OCH$_3$-PY4 |
| (A8-1.164) | 2-CH(CH$_3$)$_2$-6-OCH$_3$-PY4 |
| (A8-1.165) | 2-CH$_2$CH(CH$_3$)$_2$-6-OCH$_3$-PY4 |
| (A8-1.166) | 2-CH$_2$cC$_3$H$_5$-6-OCH$_3$-PY4 |
| (A8-1.167) | 6-OCHF$_2$-PY4 |
| (A8-1.168) | 2-CH$_3$-6-OCHF$_2$-PY4 |
| (A8-1.169) | 2-CF$_3$-6-OCHF$_2$-PY4 |
| (A8-1.170) | 2-cC$_3$H$_5$-6-OCHF$_2$-PY4 |
| (A8-1.171) | 2-CH(CH$_3$)$_2$-6-OCHF$_2$-PY4 |
| (A8-1.172) | 2-CH$_2$CH(CH$_3$)$_2$-6-OCHF$_2$-PY4 |
| (A8-1.173) | 2-CH$_2$cC$_3$H$_5$-6-OCHF$_2$-PY4 |

PY4 = pyrimidin-4-yl
cC$_3$H$_5$ = cyclopropyl

Another preferred embodiment of the invention relates to the compounds of the formula I, to the salts thereof, the N-oxides thereof and the salts of the N-oxides thereof and to the methods and uses of such compounds, wherein A is a radical A8-2,

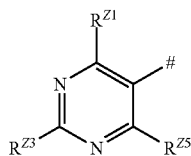

(A8-2)

wherein #, $R^{Z1}$, $R^{Z3}$ and $R^{Z5}$ are as defined herein.

Another preferred embodiment of the present invention relates to compounds of formula I wherein A is selected from the suitable example of radicals A8.

Examples of suitable radicals A8-2 are the radicals of formulae A8-2.1 to A8-2.131, as defined in Table A8-2.

TABLE A8-2

| | |
|---|---|
| (A8-2.1) | 5-Pyrimidinyl |
| (A8-2.2) | 2-Cl-PY5 |
| (A8-2.3) | 2-Br-PY5 |
| (A8-2.4) | 2-$CH_3$-PY5 |
| (A8-2.5) | 2-$C_2H_5$-PY5 |
| (A8-2.6) | 2-c-$C_3H_5$-PY5 |
| (A8-2.7) | 2-$CH(CH_3)_2$-PY5 |
| (A8-2.8) | 2-Isobutyl-PY5 |
| (A8-2.9) | 2-$CH_2$-c-$C_3H_5$-PY5 |
| (A8-2.10) | 2-$CHF_2$-PY5 |
| (A8-2.11) | 2-$CF_3$-PY5 |
| (A8-2.12) | 2-$CH_2CF_3$-PY5 |
| (A8-2.13) | 2-$CH_2OCH_3$-PY5 |
| (A8-2.14) | 2-$CH_2OCHF_2$-PY5 |
| (A8-2.15) | 2-$CH_2OCF_3$-PY5 |
| (A8-2.16) | 2-$CH_2CN$-PY5 |
| (A8-2.17) | 2-$CH_2CH_2OCH_3$-PY5 |
| (A8-2.18) | 2-$OCH_3$-PY5 |
| (A8-2.19) | 2-$OC_2H_5$-PY5 |
| (A8-2.20) | 2-Cl-4-$CH_3$-PY5 |
| (A8-2.21) | 2-Br-4-$CH_3$-PY5 |
| (A8-2.22) | 2,4-$(CH_3)_2$-PY5 |
| (A8-2.23) | 2-$C_2H_5$-4-$CH_3$-PY5 |
| (A8-2.24) | 2-c-$C_3H_5$-4-$CH_3$-PY5 |
| (A8-2.25) | 2-$CH(CH_3)_2$-4-$CH_3$-PY5 |
| (A8-2.26) | 2-Isobutyl-4-$CH_3$-PY5 |
| (A8-2.27) | 2-$CH_2$-c-$C_3H_5$-4-$CH_3$-PY5 |
| (A8-2.28) | 2-$CHF_2$-4-$CH_3$-PY5 |
| (A8-2.29) | 2-$CF_3$-4-$CH_3$-PY5 |
| (A8-2.30) | 2-$CH_2CF_3$-4-$CH_3$-PY5 |
| (A8-2.31) | 2-$CH_2OCH_3$-4-$CH_3$-PY5 |
| (A8-2.32) | 2-$CH_2OCHF_2$-4-$CH_3$-PY5 |
| (A8-2.33) | 2-$CH_2OCF_3$-4-$CH_3$-PY5 |
| (A8-2.34) | 2-$CH_2CN$-4-$CH_3$-PY5 |
| (A8-2.35) | 2-$CH_2OC_2H_5$-4-$CH_3$-PY5 |
| (A8-2.36) | 2-$OCH_3$-4-$CH_3$-PY5 |
| (A8-2.37) | 2-$OC_2H_5$-4-$CH_3$-PY5 |
| (A8-2.38) | 2-Cl-4-$CF_3$-PY5 |
| (A8-2.39) | 2-Br-4-$CF_3$-PY5 |
| (A8-2.40) | 2-$CH_3$-4-$CF_3$-PY5 |
| (A8-2.41) | 2-$C_2H_5$-4-$CF_3$-PY5 |
| (A8-2.42) | 2-c-$C_3H_5$-4-$CF_3$-PY5 |
| (A8-2.43) | 2-$CH(CH_3)_2$-4-$CF_3$-PY5 |
| (A8-2.44) | 2-Isobutyl-4-$CF_3$-PY5 |
| (A8-2.45) | 2-$CH_2$-c-$C_3H_5$-4-$CF_3$-PY5 |
| (A8-2.46) | 2-$CHF_2$-4-$CF_3$-PY5 |
| (A8-2.47) | 2-$CF_3$-4-$CF_3$-PY5 |
| (A8-2.48) | 2-$CH_2CF_3$-4-$CF_3$-PY5 |
| (A8-2.49) | 2-$CH_2OCH_3$-4-$CF_3$-PY5 |
| (A8-2.50) | 2-$CH_2OCHF_2$-4-$CF_3$-PY5 |
| (A8-2.51) | 2-$CH_2OCF_3$-4-$CF_3$-PY5 |
| (A8-2.52) | 2-$CH_2CN$-4-$CF_3$-PY5 |
| (A8-2.53) | 2-$CH_2OC_2H_5$-4-$CF_3$-PY5 |
| (A8-2.54) | 2-$OCH_3$-4-$CF_3$-PY5 |
| (A8-2.55) | 2-$OC_2H_5$-4-$CF_3$-PY5 |
| (A8-2.56) | 2,4-$Cl_2$-PY5 |
| (A8-2.57) | 2-$CH_3$-4-Cl-PY5 |
| (A8-2.58) | 2-$OC_2H_5$-4-Cl-PY5 |
| (A8-2.59) | 2-c-$C_3H_5$-4-Cl-PY5 |
| (A8-2.60) | 2-$CH(CH_3)_2$-4-Cl-PY5 |
| (A8-2.61) | 2-Isobutyl-4-Cl-PY5 |
| (A8-2.62) | 2-$CH_2$-c-$C_3H_5$-4-Cl-PY5 |
| (A8-2.63) | 2-$CHF_2$-4-Cl-PY5 |
| (A8-2.64) | 2-$CF_3$-4-Cl-PY5 |
| (A8-2.65) | 2-$CH_2CF_3$-4-Cl-PY5 |
| (A8-2.66) | 2-$CH_2OCH_3$-4-Cl-PY5 |
| (A8-2.67) | 2-$CH_2OCHF_2$-4-Cl-PY5 |
| (A8-2.68) | 2-$CH_2OCF_3$-4-Cl-PY5 |
| (A8-2.69) | 2-$CH_2CN$-4-Cl-PY5 |
| (A8-2.70) | 2-$CH_2OC_2H_5$-4-Cl-PY5 |
| (A8-2.71) | 2-$OCH_3$-4-Cl-PY5 |
| (A8-2.72) | 2-$OC_2H_5$-4-Cl-PY5 |
| (A8-2.73) | 2-Cl-4-$C_2H_5$-PY5 |
| (A8-2.74) | 2,4-$Br_2$-PY5 |
| (A8-2.75) | 2-$CH_3$-4-Br-PY5 |
| (A8-2.76) | 2-$C_2H_5$-4-Br-PY5 |
| (A8-2.77) | 2-c-$C_3H_5$-4-Br-PY5 |
| (A8-2.78) | 2-$CH(CH_3)_2$-4-Br-PY5 |
| (A8-2.79) | 2-Isobutyl-4-Br-PY5 |
| (A8-2.80) | 2-$CH_2$-c-$C_3H_5$-4-Br-PY5 |
| (A8-2.81) | 2-$CHF_2$-4-Br-PY5 |
| (A8-2.82) | 2-$CF_3$-4-Br-PY5 |
| (A8-2.83) | 2-$CH_2CF_3$-4-Br-PY5 |
| (A8-2.84) | 2-$CH_2OCH_3$-4-Br-PY5 |
| (A8-2.85) | 2-$CH_2OCHF_2$-4-Br-PY5 |
| (A8-2.86) | 2-$CH_2OCF_3$-4-Br-PY5 |
| (A8-2.87) | 2-$CH_2CN$-4-Br-PY5 |
| (A8-2.88) | 2-$CH_2OC_2H_5$-4-Br-PY5 |
| (A8-2.89) | 2-$OCH_3$-4-Br-PY5 |
| (A8-2.90) | 2-$OC_2H_5$-4-Br-PY5 |
| (A8-2.91) | 2-Br-4-$C_2H_5$-PY5 |
| (A8-2.92) | 2-$CH_3$-4-$C_2H_5$-PY5 |
| (A8-2.93) | 2-$C_2H_5$-4-$C_2H_5$-PY5 |
| (A8-2.94) | 2-c-$C_3H_5$-4-$C_2H_5$-PY5 |
| (A8-2.95) | 2-$CH(CH_3)_2$-4-$C_2H_5$-PY5 |
| (A8-2.96) | 2-Isobutyl-4-$C_2H_5$-PY5 |
| (A8-2.97) | 2-$CH_2$-c-$C_3H_5$-4-$C_2H_5$-PY5 |
| (A8-2.98) | 2-$CHF_2$-4-$C_2H_5$-PY5 |
| (A8-2.99) | 2-$CF_3$-4-$C_2H_5$-PY5 |
| (A8-2.100) | 2-$CH_2CF_3$-4-$C_2H_5$-PY5 |
| (A8-2.101) | 2-$CH_2OCH_3$-4-$C_2H_5$-PY5 |
| (A8-2.102) | 2-$CH_2OCHF_2$-4-$C_2H_5$-PY5 |
| (A8-2.103) | 2-$CH_2OCF_3$-4-$C_2H_5$-PY5 |
| (A8-2.104) | 2-$CH_2CN$-4-$C_2H_5$-PY5 |
| (A8-2.105) | 2-$CH_2OC_2H_5$-4-$C_2H_5$-PY5 |
| (A8-2.106) | 2-$OCH_3$-4-$C_2H_5$-PY5 |
| (A8-2.107) | 2-$OC_2H_5$-4-$C_2H_5$-PY5 |
| (A8-2.108) | 2-Cl-4-$CHF_2$-PY5 |
| (A8-2.109) | 2-Br-4-$CHF_2$-PY5 |
| (A8-2.110) | 2-$CH_3$-4-$CHF_2$-PY5 |
| (A8-2.111) | 2-$C_2H_5$-4-$CHF_2$-PY5 |
| (A8-2.112) | 2-c-$C_3H_5$-4-$CHF_2$-PY5 |
| (A8-2.113) | 2-$CH(CH_3)_2$-4-$CHF_2$-PY5 |
| (A8-2.114) | 2-Isobutyl-4-$CHF_2$-PY5 |
| (A8-2.115) | 2-$CH_2$-c-$C_3H_5$-4-$CHF_2$-PY5 |
| (A8-2.116) | 2,4-$(CHF_2)_2$-PY5 |
| (A8-2.117) | 2-$CF_3$-4-$CHF_2$-PY5 |
| (A8-2.118) | 2-$CH_2CF_3$-4-$CHF_2$-PY5 |
| (A8-2.119) | 2-$CH_2OCH_3$-4-$CHF_2$-PY5 |
| (A8-2.120) | 2-$CH_2OCHF_2$-4-$CHF_2$-PY5 |
| (A8-2.121) | 2-$CH_2OCF_3$-4-$CHF_2$-PY5 |
| (A8-2.122) | 2-$CH_2CN$-4-$CHF_2$-PY5 |
| (A8-2.123) | 2-$CH_2OC_2H_5$-4-$CHF_2$-PY5 |
| (A8-2.124) | 2-$OCH_3$-4-$CHF_2$-PY5 |
| (A8-2.125) | 2-$OC_2H_5$-4-$CHF_2$-PY5 |
| (A8-2.126) | 4-$CH_3$-PY5 |
| (A8-2.127) | 4-$CF_3$-PY5 |
| (A8-2.128) | 4-Cl-PY5 |
| (A8-2.129) | 4-Br-PY5 |
| (A8-2.130) | 4-$C_2H_5$-PY5 |
| (A8-2.131) | 4-$CHF_2$-PY5 |

PY5 = pyrimidin-5-yl
c-$C_3H_5$ = cyclopropyl

Another preferred embodiment of the invention relates to compounds of the formula I, to the salts thereof, the N-oxides thereof and the salts of the N-oxides thereof and to the methods and uses of such compounds, wherein A is a radical A8-3,

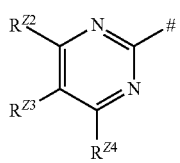

(A8-3)

wherein #, $R^{Z2}$, $R^{Z3}$ and $R^{Z4}$ are as defined herein.

Examples of suitable radicals A8-3 are the radicals of formulae A8-3.1 to A8-3.13, as defined in Table A8-3.

TABLE A8-3

| | |
|---|---|
| (A8-3.1) | 2-Pyrimidinyl |
| (A8-3.2) | 4-$CH_3$-2-pyrimidinyl |
| (A8-3.3) | 5-$CH_3$-2-pyrimidinyl |
| (A8-3.4) | 4-$C_2H_5$-2-pyrimidinyl |
| (A8-3.5) | 5-$C_2H_5$-2-pyrimidinyl |
| (A8-3.6) | 4-$CF_3$-2-pyrimidinyl |
| (A8-3.7) | 5-$CF_3$-2-pyrimidinyl |
| (A8-3.8) | 4,5-$(CH_3)_2$-2-pyrimidinyl |
| (A8-3.9) | 4,5,6-$(CH_3)_3$-2-pyrimidinyl |
| (A8-3.10) | 4-$C_2H_5$-5-$CH_3$-2-pyrimidinyl |
| (A8-3.11) | 4-$CH_3$-5-$C_2H_5$-2-pyrimidinyl |
| (A8-3.12) | 4-$CF_3$-5-$CH_3$-2-pyrimidinyl |
| (A8-3.13) | 4-$CH_3$-5-$CF_3$-2-pyrimidinyl |

A preferred embodiment of the invention relates to compounds of the formula I and to the salts thereof, the N-oxides thereof and the salts of the N-oxides thereof, wherein $X^1$ is O. These compounds are hereinafter also referred to as compounds I1.

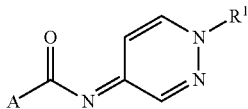

(I1)

In formula I1, the variables A and $R^1$ are as defined herein.

Among the compounds of the formula I1, preference is given to those compounds, wherein the radicals A and $R^1$ have one of the preferred meanings.

A preferred embodiment of the invention relates to the compounds of the formula I1, to their N-oxides and their salts, wherein $R^1$ is selected from the group consisting of CN, $C_1$-$C_{10}$-alkyl, $C_1$-$C_{10}$-haloalkyl, $C_3$-$C_{10}$-alkenyl, $C_3$-$C_{10}$-haloalkenyl, $C_3$-$C_{10}$-alkynyl, $C_1$-$C_4$-alkylene-CN and $C_1$-$C_4$-alkylene-$OR^a$, in particular from the group consisting of CN, $C_1$-$C_4$-alkyl, $C_1$-$C_4$-haloalkyl, $C_3$-$C_4$-alkenyl, $C_3$-$C_4$-haloalkenyl, $C_3$-$C_4$-alkynyl, $C_1$-$C_4$-alkylene-CN and $C_1$-$C_4$-alkylene-$OR^a$. where $R^a$ is as defined herein and wherein $R^a$, where occurring, preferably has one of the meanings given as preferred meanings and where $R^a$ is in particular selected from hydrogen, $C_1$-$C_4$-alkyl and $C_1$-$C_4$-haloalkyl.

Another preferred embodiment of the invention relates to the compounds of the formula I1, to their N-oxides and their salts, wherein $R^1$ is selected from the group consisting of $C_1$-$C_4$-alkylene-CN, $C_1$-$C_4$-alkylene-$OR^a$, $C_1$-$C_4$-alkylene-$C(Y)R^b$, $C_1$-$C_4$-alkylen-$NR^eR^f$, $C_1$-$C_4$-alkylen-$C(Y)NR^gR^h$, phenyl-$C_1$-$C_4$-alkyl, in particular benzyl, heterocyclyl-$C_1$-$C_4$-alkyl, in particular heterocyclylmethyl, and hetaryl-$C_1$-$C_4$-alkyl, in particular hetarylmethyl, wherein the phenyl, heterocyclyl or hetaryl ring in last six mentioned radicals may be unsubstituted or may carry 1, 2, 3, 4 or 5 radicals $R^y$, which are as defined herein and which are preferably selected respectively from $NO_2$, $C_1$-$C_4$-alkoxy, $C_1$-$C_4$-haloalkoxy, $C_1$-$C_4$-alkylsulfonyl and $C_1$-$C_4$-haloalkylsulfonyl or from halogen, $NO_2$, $C_1$-$C_4$-alkyl, $C_1$-$C_4$-haloalkyl, $C_1$-$C_4$-alkoxy, $C_1$-$C_4$-haloalkoxy.

A further particular preferred embodiment of the invention relates to compounds of the formula I1, to their N-oxides and their salts, wherein $R^1$ is selected from the group consisting of phenyl and hetaryl, in particular from phenyl, wherein phenyl and hetaryl are unsubstituted or carry 1, 2, 3, 4 or 5 radicals $R^y$, which are as defined herein and which are preferably selected respectively from $NO_2$, $C_1$-$C_4$-alkoxy, $C_1$-$C_4$-haloalkoxy, $C_1$-$C_4$-alkylsulfonyl and $C_1$-$C_4$-haloalkylsulfonyl or from halogen, $NO_2$, $C_1$-$C_4$-alkyl, $C_1$-$C_4$-haloalkyl, $C_1$-$C_4$-alkoxy, $C_1$-$C_4$-haloalkoxy.

A further particular preferred embodiment of the invention relates to the compounds of the formula I1, to their N-oxides and their salts, wherein $R^1$ is selected from the group consisting of $C_1$-$C_4$-alkyl, $C_1$-$C_4$-haloalkyl and $C_1$-$C_4$-alkoxy-$C_1$-$C_4$-alkyl. Among this embodiment, particular preference is given to compounds, wherein $R^1$ is $C_1$-$C_3$-alkyl. Further, among this embodiment, likewise preference is given to compounds, wherein $R^1$ is $C_1$-$C_3$-haloalkyl or $C_1$-$C_2$-alkoxy-$C_1$-$C_2$-alkyl.

In another particular preferred embodiment, the invention relates to compounds of formula I1, to their N-oxides and their salts, wherein, $R^1$ is selected from the group consisting of $C_1$-$C_4$-alkylen-$NR^eR^f$, phenyl-$C_1$-$C_4$-alkyl, in particular benzyl, 1-phenylethyl or 2-phenylethyl, heterocyclyl-$C_1$-$C_4$-alkyl, in particular heterocyclylmethyl, 1-heterocyclylethyl or 2-heterocyclylethyl, and hetaryl-$C_1$-$C_4$-alkyl, in particular hetaryl-methyl, 1-hetarylethyl or 2-hetarylethyl, wherein the last twelve mentioned radicals may be unsubstituted or may carry 1, 2 or 3 radicals $R^y$, which are as defined above and which are preferably selected from halogen, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylsulfonyl and $C_1$-$C_4$-haloalkylsulfonyl.

A very preferred embodiment of the invention relates to compounds of the formula I1 and to the salts thereof, the N-oxides thereof and the salts of the N-oxides thereof, wherein A is a radical A2, in particular a radical A2, where Z is N—$R^N$, where $R^N$ is as defined herein and wherein $R^N$ is preferably selected from the group consisting of $NO_2$, $C_1$-$C_{10}$-alkyl, $C_2$-$C_{10}$-alkenyl and $C_2$-$C_{10}$-alkynyl, wherein the three last mentioned radicals may be unsubstituted or may be partially or fully halogenated or may carry 1, 2 or 3 identical or different substituents $R^x$, or wherein $R^N$ is further selected from $OR^a$, $C(Y)R^b$, $C(Y)OR^c$, $S(O)_mR^d$, $NR^eR^f$, $C(Y)NR^gR^h$, $S(O)_mNR^eR^f$, $C(Y)NR^iNR^eR^f$, $C_1$-$C_5$-alkylene-$OR^a$, $C_1$-$C_5$-alkylene-CN, $C_1$-$C_5$-alkylene-$C(Y)R^b$, $C_1$-$C_5$-alkylene-$C(Y)OR^c$, $C_1$-$C_5$-alkylene-$NR^eR^f$, $C_1$-$C_5$-alkylene-$C(Y)NR^gR^h$, $C_1$-$C_5$-alkylene-$S(O)_mR^d$, $C_1$-$C_5$-alkylene-$S(O)_mNR^eR^f$, $C_1$-$C_5$-alkylene-$NR^iNR^eR^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents $R^y$.

In the compounds of formula I1, wherein A is A2 and Z is N—$R^N$, $R^N$ is more preferably selected from the group consisting of $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents $R^x$, $C_1$-$C_4$-alkoxy-$C_2$-$C_4$-alkyl, $C_1$-$C_4$-alkylene-CN, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_5$-$C_{10}$-cycloalkenyl-$C_1$-$C_5$-alkyl, where the rings in the 8 last mentioned radicals may be unsubstituted or may carry 1, 2 or 3 identical or different substituents $R^y$. In the compounds of formula I1, wherein A is A2 and Z is N—$R^N$, $R^N$ is more preferably selected from $C_1$-$C_6$-alkyl, $C_1$-$C_6$-haloalkyl, $C_3$-$C_6$-cycloalkyl, $C_3$-$C_6$-cycloalkyl-$C_1$-$C_4$-alkyl, where the cycloalkyl moiety is in the last two mentioned radicals is unsubstituted or carries 1 or 2 radicals selected from halogen, CN and $C_1$-$C_2$-haloalkyl, heterocyclyl-$C_1$-$C_4$-alkyl, $C_1$-$C_4$-alkoxy-$C_1$-$C_4$-alkyl and $C_1$-$C_4$-alkylene-CN. In particular $R^N$ is selected from the group consisting of $C_1$-$C_4$-alkyl, $C_1$-$C_4$-haloalkyl, $C_1$-$C_2$-alkoxy-$C_2$-$C_4$-alkyl, $C_1$-$C_4$-alkylene-CN, $C_3$-$C_6$-cycloalkyl and $C_3$-$C_6$-cycloalkyl-$C_1$-$C_4$-alkyl, where the cycloalkyl moiety is in the last two mentioned radicals is unsubstituted or carries 1 or 2 radicals selected from halogen, CN and $C_1$-$C_2$-haloalkyll. Especially, $R^N$ is $C_1$-$C_4$-alkyl or $C_1$-$C_4$-haloalkyl.

Within this very preferred embodiment of the invention, wherein A in formula I1 is a radical A2, where Z is N—$R^N$, the radical A is e.g. selected from the radicals of formulae A2.a, A2.b, A2.c, A2.d, A2.e, A2.f, A2.g, A2.h, A2.i, A2.k, A2.l, A2.m, A2.n, A2.o, A2.p, A2.q, A2.r, A2.s, A2.t, A2.u, A2.v, A2.w, A2.x, A2.y, A2.z, A2.aa, A2.bb, A2.cc, A2.dd, A2.ee, A2.ff, A2.gg, A2.hh, A2.ii, A2.kk, A2.mm, A2.nn, A2.oo, A2.pp, A2.qq, A2.rr, A2.ss and A2.tt, with preference given to radicals A2.a, A2.b, A2.c, A2.d, A2.e, A2.f, A2.n, A2.o, A2.q, A2.r, A2.s, A2.t, A2.u, A2.v, A2.w, A2.x, A2.y, A2.z, A2.aa, A2.bb, A2.cc, A2.dd, A2.ee, A2.gg, A2.hh, A2.ii, A2.rr, A2.ss and A2.tt and with particular preference given to radicals of formulae A2.o, A2.p, A2.r and A2.tt, wherein Z is N$R^N$ with $R^N$ being as defined the lines of table $R^N$, in particular as defined in lines R.N 1 to R.N 8, R.N 13, R.N 15, R.N 23, R.N 24, R.N 73 to R.N 78 and R.N 82 to R.N 95.

Within this above embodiment, very particular preference is further given to the compounds of formula I1, wherein A is a radical A2, where Z is N—$R^N$, e.g. a radical, selected from the radicals A2.N1 to A2.N13, A2.N40 to A2.N52, A2.N79 to A2.N91, A2.N119 to A2.N130, A2.N157 to A2.N169, A2.N196 to A2.N208, A2.N235 to A2.N247, A2.N274 to A2.N286, A2.N313 to A2.N325, A2.N352 to A2.N364, A2.N391 to A2.N403, A2.N430 to A2.N442, A2.N469 to A2.N481, A2.N508 to A2.N520, A2.N547 to A2.N559, A2.N586 to A2.N598, A2.N625 to A2.N637, A2.N664 to A2.N676, A2.N703 to A2.N715, A2.N742 to A2.N754, A2.N781 to A2.N793, A2.N820 to A2.N832, A2.N859 to A2.N871, A2.N898 to A2.N910, A2.N937 to A2.N949 and A2.N976 to A2.N988.

Examples of compounds of this particularly preferred embodiment are the compounds given in the following tables 1 to 338. The corresponding salts of the compounds, their N-oxides and the salts of their N-oxides are also included in this embodiment. The groups mentioned for a substituent in the tables are furthermore per se, independently of the combination in which they are mentioned, a particularly preferred aspect of the substituent in question.

Table 1: Compounds of the formulae I1, wherein A is a radical A2-N1 and $R^1$ has one of the meanings given in Table B.
Table 2: Compounds of the formulae I1, wherein A is a radical A2-N2 and $R^1$ has one of the meanings given in Table B.
Table 3: Compounds of the formulae I1, wherein A is a radical A2-N3 and $R^1$ has one of the meanings given in Table B.
Table 4: Compounds of the formulae I1, wherein A is a radical A2-N4 and $R^1$ has one of the meanings given in Table B.
Table 5: Compounds of the formulae I1, wherein A is a radical A2-N5 and $R^1$ has one of the meanings given in Table B.
Table 6: Compounds of the formulae I1, wherein A is a radical A2-N6 and $R^1$ has one of the meanings given in Table B.
Table 7: Compounds of the formulae I1, wherein A is a radical A2-N7 and $R^1$ has one of the meanings given in Table B.
Table 8: Compounds of the formulae I1, wherein A is a radical A2-N8 and $R^1$ has one of the meanings given in Table B.
Table 9: Compounds of the formulae I1, wherein A is a radical A2-N9 and $R^1$ has one of the meanings given in Table B.
Table 10: Compounds of the formulae I1, wherein A is a radical A2-N10 and $R^1$ has one of the meanings given in Table B.
Table 11: Compounds of the formulae I1, wherein A is a radical A2-N11 and $R^1$ has one of the meanings given in Table B.
Table 12: Compounds of the formulae I1, wherein A is a radical A2-N12 and $R^1$ has one of the meanings given in Table B.
Table 13: Compounds of the formulae I1, wherein A is a radical A2-N13 and $R^1$ has one of the meanings given in Table B.
Table 14: Compounds of the formulae I1, wherein A is a radical A2-N40 and $R^1$ has one of the meanings given in Table B.
Table 15: Compounds of the formulae I1, wherein A is a radical A2-N41 and $R^1$ has one of the meanings given in Table B.
Table 16: Compounds of the formulae I1, wherein A is a radical A2-N42 and $R^1$ has one of the meanings given in Table B.
Table 17: Compounds of the formulae I1, wherein A is a radical A2-N43 and $R^1$ has one of the meanings given in Table B.
Table 18: Compounds of the formulae I1, wherein A is a radical A2-N44 and $R^1$ has one of the meanings given in Table B.
Table 19: Compounds of the formulae I1, wherein A is a radical A2-N45 and $R^1$ has one of the meanings given in Table B.
Table 20: Compounds of the formulae I1, wherein A is a radical A2-N46 and $R^1$ has one of the meanings given in Table B.
Table 21: Compounds of the formulae I1, wherein A is a radical A2-N47 and $R^1$ has one of the meanings given in Table B.
Table 22: Compounds of the formulae I1, wherein A is a radical A2-N48 and $R^1$ has one of the meanings given in Table B.
Table 23: Compounds of the formulae I1, wherein A is a radical A2-N49 and $R^1$ has one of the meanings given in Table B.
Table 24: Compounds of the formulae I1, wherein A is a radical A2-N50 and $R^1$ has one of the meanings given in Table B.
Table 25: Compounds of the formulae I1, wherein A is a radical A2-N51 and $R^1$ has one of the meanings given in Table B.
Table 26: Compounds of the formulae I1, wherein A is a radical A2-N52 and $R^1$ has one of the meanings given in Table B.
Table 27: Compounds of the formulae I1, wherein A is a radical A2-N79 and $R^1$ has one of the meanings given in Table B.
Table 28: Compounds of the formulae I1, wherein A is a radical A2-N80 and $R^1$ has one of the meanings given in Table B.
Table 29: Compounds of the formulae I1, wherein A is a radical A2-N81 and $R^1$ has one of the meanings given in Table B.

Table 30: Compounds of the formulae I1, wherein A is a radical A2-N82 and $R^1$ has one of the meanings given in Table B.
Table 31: Compounds of the formulae I1, wherein A is a radical A2-N83 and $R^1$ has one of the meanings given in Table B.
Table 32: Compounds of the formulae I1, wherein A is a radical A2-N84 and $R^1$ has one of the meanings given in Table B.
Table 33: Compounds of the formulae I1, wherein A is a radical A2-N85 and $R^1$ has one of the meanings given in Table B.
Table 34: Compounds of the formulae I1, wherein A is a radical A2-N86 and $R^1$ has one of the meanings given in Table B.
Table 35: Compounds of the formulae I1, wherein A is a radical A2-N87 and $R^1$ has one of the meanings given in Table B.
Table 36: Compounds of the formulae I1, wherein A is a radical A2-N88 and $R^1$ has one of the meanings given in Table B.
Table 37: Compounds of the formulae I1, wherein A is a radical A2-N89 and $R^1$ has one of the meanings given in Table B.
Table 38: Compounds of the formulae I1, wherein A is a radical A2-N90 and $R^1$ has one of the meanings given in Table B.
Table 39: Compounds of the formulae I1, wherein A is a radical A2-N91 and $R^1$ has one of the meanings given in Table B.
Table 40: Compounds of the formulae I1, wherein A is a radical A2-N118 and $R^1$ has one of the meanings given in Table B.
Table 41: Compounds of the formulae I1, wherein A is a radical A2-N119 and $R^1$ has one of the meanings given in Table B.
Table 42: Compounds of the formulae I1, wherein A is a radical A2-N120 and $R^1$ has one of the meanings given in Table B.
Table 43: Compounds of the formulae I1, wherein A is a radical A2-N121 and $R^1$ has one of the meanings given in Table B.
Table 44: Compounds of the formulae I1, wherein A is a radical A2-N122 and $R^1$ has one of the meanings given in Table B.
Table 45: Compounds of the formulae I1, wherein A is a radical A2-N123 and $R^1$ has one of the meanings given in Table B.
Table 46: Compounds of the formulae I1, wherein A is a radical A2-N124 and $R^1$ has one of the meanings given in Table B.
Table 47: Compounds of the formulae I1, wherein A is a radical A2-N125 and $R^1$ has one of the meanings given in Table B.
Table 48: Compounds of the formulae I1, wherein A is a radical A2-N126 and $R^1$ has one of the meanings given in Table B.
Table 49: Compounds of the formulae I1, wherein A is a radical A2-N127 and $R^1$ has one of the meanings given in Table B.
Table 50: Compounds of the formulae I1, wherein A is a radical A2-N128 and $R^1$ has one of the meanings given in Table B.
Table 51: Compounds of the formulae I1, wherein A is a radical A2-N129 and $R^1$ has one of the meanings given in Table B.
Table 52: Compounds of the formulae I1, wherein A is a radical A2-N130 and $R^1$ has one of the meanings given in Table B.
Table 53: Compounds of the formulae I1, wherein A is a radical A2-N157 and $R^1$ has one of the meanings given in Table B.
Table 54: Compounds of the formulae I1, wherein A is a radical A2-N158 and $R^1$ has one of the meanings given in Table B.
Table 55: Compounds of the formulae I1, wherein A is a radical A2-N159 and $R^1$ has one of the meanings given in Table B.
Table 56: Compounds of the formulae I1, wherein A is a radical A2-N160 and $R^1$ has one of the meanings given in Table B.
Table 57: Compounds of the formulae I1, wherein A is a radical A2-N161 and $R^1$ has one of the meanings given in Table B.
Table 58: Compounds of the formulae I1, wherein A is a radical A2-N162 and $R^1$ has one of the meanings given in Table B.
Table 59: Compounds of the formulae I1, wherein A is a radical A2-N163 and $R^1$ has one of the meanings given in Table B.
Table 60: Compounds of the formulae I1, wherein A is a radical A2-N164 and $R^1$ has one of the meanings given in Table B.
Table 61: Compounds of the formulae I1, wherein A is a radical A2-N165 and $R^1$ has one of the meanings given in Table B.
Table 62: Compounds of the formulae I1, wherein A is a radical A2-N166 and $R^1$ has one of the meanings given in Table B.
Table 63: Compounds of the formulae I1, wherein A is a radical A2-N167 and $R^1$ has one of the meanings given in Table B.
Table 64: Compounds of the formulae I1, wherein A is a radical A2-N168 and $R^1$ has one of the meanings given in Table B.
Table 65: Compounds of the formulae I1, wherein A is a radical A2-N169 and $R^1$ has one of the meanings given in Table B.
Table 66: Compounds of the formulae I1, wherein A is a radical A2-N196 and $R^1$ has one of the meanings given in Table B.
Table 67: Compounds of the formulae I1, wherein A is a radical A2-N197 and $R^1$ has one of the meanings given in Table B.
Table 68: Compounds of the formulae I1, wherein A is a radical A2-N198 and $R^1$ has one of the meanings given in Table B.
Table 69: Compounds of the formulae I1, wherein A is a radical A2-N199 and $R^1$ has one of the meanings given in Table B.
Table 70: Compounds of the formulae I1, wherein A is a radical A2-N200 and $R^1$ has one of the meanings given in Table B.
Table 71: Compounds of the formulae I1, wherein A is a radical A2-N201 and $R^1$ has one of the meanings given in Table B.
Table 72: Compounds of the formulae I1, wherein A is a radical A2-N202 and $R^1$ has one of the meanings given in Table B.
Table 73: Compounds of the formulae I1, wherein A is a radical A2-N203 and $R^1$ has one of the meanings given in Table B.

Table 74: Compounds of the formulae I1, wherein A is a radical A2-N204 and $R^1$ has one of the meanings given in Table B.
Table 75: Compounds of the formulae I1, wherein A is a radical A2-N205 and $R^1$ has one of the meanings given in Table B.
Table 76: Compounds of the formulae I1, wherein A is a radical A2-N206 and $R^1$ has one of the meanings given in Table B.
Table 77: Compounds of the formulae I1, wherein A is a radical A2-N207 and $R^1$ has one of the meanings given in Table B.
Table 78: Compounds of the formulae I1, wherein A is a radical A2-N208 and $R^1$ has one of the meanings given in Table B.
Table 79: Compounds of the formulae I1, wherein A is a radical A2-N235 and $R^1$ has one of the meanings given in Table B.
Table 80: Compounds of the formulae I1, wherein A is a radical A2-N236 and $R^1$ has one of the meanings given in Table B.
Table 81: Compounds of the formulae I1, wherein A is a radical A2-N237 and $R^1$ has one of the meanings given in Table B.
Table 82: Compounds of the formulae I1, wherein A is a radical A2-N238 and $R^1$ has one of the meanings given in Table B.
Table 83: Compounds of the formulae I1, wherein A is a radical A2-N239 and $R^1$ has one of the meanings given in Table B.
Table 84: Compounds of the formulae I1, wherein A is a radical A2-N240 and $R^1$ has one of the meanings given in Table B.
Table 85: Compounds of the formulae I1, wherein A is a radical A2-N241 and $R^1$ has one of the meanings given in Table B.
Table 86: Compounds of the formulae I1, wherein A is a radical A2-N242 and $R^1$ has one of the meanings given in Table B.
Table 87: Compounds of the formulae I1, wherein A is a radical A2-N243 and $R^1$ has one of the meanings given in Table B.
Table 88: Compounds of the formulae I1, wherein A is a radical A2-N244 and $R^1$ has one of the meanings given in Table B.
Table 89: Compounds of the formulae I1, wherein A is a radical A2-N245 and $R^1$ has one of the meanings given in Table B.
Table 90: Compounds of the formulae I1, wherein A is a radical A2-N246 and $R^1$ has one of the meanings given in Table B.
Table 91: Compounds of the formulae I1, wherein A is a radical A2-N247 and $R^1$ has one of the meanings given in Table B.
Table 92: Compounds of the formulae I1, wherein A is a radical A2-N274 and $R^1$ has one of the meanings given in Table B.
Table 93: Compounds of the formulae I1, wherein A is a radical A2-N275 and $R^1$ has one of the meanings given in Table B.
Table 94: Compounds of the formulae I1, wherein A is a radical A2-N276 and $R^1$ has one of the meanings given in Table B.
Table 95: Compounds of the formulae I1, wherein A is a radical A2-N277 and $R^1$ has one of the meanings given in Table B.
Table 96: Compounds of the formulae I1, wherein A is a radical A2-N278 and $R^1$ has one of the meanings given in Table B.
Table 97: Compounds of the formulae I1, wherein A is a radical A2-N279 and $R^1$ has one of the meanings given in Table B.
Table 98: Compounds of the formulae I1, wherein A is a radical A2-N280 and $R^1$ has one of the meanings given in Table B.
Table 99: Compounds of the formulae I1, wherein A is a radical A2-N281 and $R^1$ has one of the meanings given in Table B.
Table 100: Compounds of the formulae I1, wherein A is a radical A2-N282 and $R^1$ has one of the meanings given in Table B.
Table 101: Compounds of the formulae I1, wherein A is a radical A2-N283 and $R^1$ has one of the meanings given in Table B.
Table 102: Compounds of the formulae I1, wherein A is a radical A2-N284 and $R^1$ has one of the meanings given in Table B.
Table 103: Compounds of the formulae I1, wherein A is a radical A2-N285 and $R^1$ has one of the meanings given in Table B.
Table 104: Compounds of the formulae I1, wherein A is a radical A2-N286 and $R^1$ has one of the meanings given in Table B.
Table 105: Compounds of the formulae I1, wherein A is a radical A2-N313 and $R^1$ has one of the meanings given in Table B.
Table 106: Compounds of the formulae I1, wherein A is a radical A2-N314 and $R^1$ has one of the meanings given in Table B.
Table 107: Compounds of the formulae I1, wherein A is a radical A2-N315 and $R^1$ has one of the meanings given in Table B.
Table 108: Compounds of the formulae I1, wherein A is a radical A2-N316 and $R^1$ has one of the meanings given in Table B.
Table 109: Compounds of the formulae I1, wherein A is a radical A2-N317 and $R^1$ has one of the meanings given in Table B.
Table 110: Compounds of the formulae I1, wherein A is a radical A2-N318 and $R^1$ has one of the meanings given in Table B.
Table 111: Compounds of the formulae I1, wherein A is a radical A2-N319 and $R^1$ has one of the meanings given in Table B.
Table 112: Compounds of the formulae I1, wherein A is a radical A2-N320 and $R^1$ has one of the meanings given in Table B.
Table 113: Compounds of the formulae I1, wherein A is a radical A2-N321 and $R^1$ has one of the meanings given in Table B.
Table 114: Compounds of the formulae I1, wherein A is a radical A2-N322 and $R^1$ has one of the meanings given in Table B.
Table 115: Compounds of the formulae I1, wherein A is a radical A2-N323 and $R^1$ has one of the meanings given in Table B.
Table 116: Compounds of the formulae I1, wherein A is a radical A2-N324 and $R^1$ has one of the meanings given in Table B.
Table 117: Compounds of the formulae I1, wherein A is a radical A2-N325 and $R^1$ has one of the meanings given in Table B.

Table 118: Compounds of the formulae I1, wherein A is a radical A2-N352 and R$^1$ has one of the meanings given in Table B.
Table 119: Compounds of the formulae I1, wherein A is a radical A2-N353 and R$^1$ has one of the meanings given in Table B.
Table 120: Compounds of the formulae I1, wherein A is a radical A2-N354 and R$^1$ has one of the meanings given in Table B.
Table 121: Compounds of the formulae I1, wherein A is a radical A2-N355 and R$^1$ has one of the meanings given in Table B.
Table 122: Compounds of the formulae I1, wherein A is a radical A2-N356 and R$^1$ has one of the meanings given in Table B.
Table 123: Compounds of the formulae I1, wherein A is a radical A2-N357 and R$^1$ has one of the meanings given in Table B.
Table 124: Compounds of the formulae I1, wherein A is a radical A2-N358 and R$^1$ has one of the meanings given in Table B.
Table 125: Compounds of the formulae I1, wherein A is a radical A2-N359 and R$^1$ has one of the meanings given in Table B.
Table 126: Compounds of the formulae I1, wherein A is a radical A2-N360 and R$^1$ has one of the meanings given in Table B.
Table 127: Compounds of the formulae I1, wherein A is a radical A2-N361 and R$^1$ has one of the meanings given in Table B.
Table 128: Compounds of the formulae I1, wherein A is a radical A2-N362 and R$^1$ has one of the meanings given in Table B.
Table 129: Compounds of the formulae I1, wherein A is a radical A2-N363 and R$^1$ has one of the meanings given in Table B.
Table 130: Compounds of the formulae I1, wherein A is a radical A2-N364 and R$^1$ has one of the meanings given in Table B.
Table 131: Compounds of the formulae I1, wherein A is a radical A2-N391 and R$^1$ has one of the meanings given in Table B.
Table 132: Compounds of the formulae I1, wherein A is a radical A2-N392 and R$^1$ has one of the meanings given in Table B.
Table 133: Compounds of the formulae I1, wherein A is a radical A2-N393 and R$^1$ has one of the meanings given in Table B.
Table 134: Compounds of the formulae I1, wherein A is a radical A2-N394 and R$^1$ has one of the meanings given in Table B.
Table 135: Compounds of the formulae I1, wherein A is a radical A2-N395 and R$^1$ has one of the meanings given in Table B.
Table 136: Compounds of the formulae I1, wherein A is a radical A2-N396 and R$^1$ has one of the meanings given in Table B.
Table 137: Compounds of the formulae I1, wherein A is a radical A2-N397 and R$^1$ has one of the meanings given in Table B.
Table 138: Compounds of the formulae I1, wherein A is a radical A2-N398 and R$^1$ has one of the meanings given in Table B.
Table 139: Compounds of the formulae I1, wherein A is a radical A2-N399 and R$^1$ has one of the meanings given in Table B.
Table 140: Compounds of the formulae I1, wherein A is a radical A2-N400 and R$^1$ has one of the meanings given in Table B.
Table 141: Compounds of the formulae I1, wherein A is a radical A2-N401 and R$^1$ has one of the meanings given in Table B.
Table 142: Compounds of the formulae I1, wherein A is a radical A2-N402 and R$^1$ has one of the meanings given in Table B.
Table 143: Compounds of the formulae I1, wherein A is a radical A2-N403 and R$^1$ has one of the meanings given in Table B.
Table 144: Compounds of the formulae I1, wherein A is a radical A2-N430 and R$^1$ has one of the meanings given in Table B.
Table 145: Compounds of the formulae I1, wherein A is a radical A2-N431 and R$^1$ has one of the meanings given in Table B.
Table 146: Compounds of the formulae I1, wherein A is a radical A2-N432 and R$^1$ has one of the meanings given in Table B.
Table 147: Compounds of the formulae I1, wherein A is a radical A2-N433 and R$^1$ has one of the meanings given in Table B.
Table 148: Compounds of the formulae I1, wherein A is a radical A2-N434 and R$^1$ has one of the meanings given in Table B.
Table 149: Compounds of the formulae I1, wherein A is a radical A2-N435 and R$^1$ has one of the meanings given in Table B.
Table 150: Compounds of the formulae I1, wherein A is a radical A2-N436 and R$^1$ has one of the meanings given in Table B.
Table 151: Compounds of the formulae I1, wherein A is a radical A2-N437 and R$^1$ has one of the meanings given in Table B.
Table 152: Compounds of the formulae I1, wherein A is a radical A2-N438 and R$^1$ has one of the meanings given in Table B.
Table 153: Compounds of the formulae I1, wherein A is a radical A2-N439 and R$^1$ has one of the meanings given in Table B.
Table 154: Compounds of the formulae I1, wherein A is a radical A2-N440 and R$^1$ has one of the meanings given in Table B.
Table 155: Compounds of the formulae I1, wherein A is a radical A2-N441 and R$^1$ has one of the meanings given in Table B.
Table 156: Compounds of the formulae I1, wherein A is a radical A2-N442 and R$^1$ has one of the meanings given in Table B.
Table 157: Compounds of the formulae I1, wherein A is a radical A2-N469 and R$^1$ has one of the meanings given in Table B.
Table 158: Compounds of the formulae I1, wherein A is a radical A2-N470 and R$^1$ has one of the meanings given in Table B.
Table 159: Compounds of the formulae I1, wherein A is a radical A2-N471 and R$^1$ has one of the meanings given in Table B.
Table 160: Compounds of the formulae I1, wherein A is a radical A2-N472 and R$^1$ has one of the meanings given in Table B.
Table 161: Compounds of the formulae I1, wherein A is a radical A2-N473 and R$^1$ has one of the meanings given in Table B.

Table 162: Compounds of the formulae I1, wherein A is a radical A2-N474 and $R^1$ has one of the meanings given in Table B.
Table 163: Compounds of the formulae I1, wherein A is a radical A2-N475 and $R^1$ has one of the meanings given in Table B.
Table 164: Compounds of the formulae I1, wherein A is a radical A2-N476 and $R^1$ has one of the meanings given in Table B.
Table 165: Compounds of the formulae I1, wherein A is a radical A2-N477 and $R^1$ has one of the meanings given in Table B.
Table 166: Compounds of the formulae I1, wherein A is a radical A2-N478 and $R^1$ has one of the meanings given in Table B.
Table 167: Compounds of the formulae I1, wherein A is a radical A2-N479 and $R^1$ has one of the meanings given in Table B.
Table 168: Compounds of the formulae I1, wherein A is a radical A2-N480 and $R^1$ has one of the meanings given in Table B.
Table 169: Compounds of the formulae I1, wherein A is a radical A2-N481 and $R^1$ has one of the meanings given in Table B.
Table 170: Compounds of the formulae I1, wherein A is a radical A2-N508 and $R^1$ has one of the meanings given in Table B.
Table 171: Compounds of the formulae I1, wherein A is a radical A2-N509 and $R^1$ has one of the meanings given in Table B.
Table 172: Compounds of the formulae I1, wherein A is a radical A2-N510 and $R^1$ has one of the meanings given in Table B.
Table 173: Compounds of the formulae I1, wherein A is a radical A2-N511 and $R^1$ has one of the meanings given in Table B.
Table 174: Compounds of the formulae I1, wherein A is a radical A2-N512 and $R^1$ has one of the meanings given in Table B.
Table 175: Compounds of the formulae I1, wherein A is a radical A2-N513 and $R^1$ has one of the meanings given in Table B.
Table 176: Compounds of the formulae I1, wherein A is a radical A2-N514 and $R^1$ has one of the meanings given in Table B.
Table 177: Compounds of the formulae I1, wherein A is a radical A2-N515 and $R^1$ has one of the meanings given in Table B.
Table 178: Compounds of the formulae I1, wherein A is a radical A2-N516 and $R^1$ has one of the meanings given in Table B.
Table 179: Compounds of the formulae I1, wherein A is a radical A2-N517 and $R^1$ has one of the meanings given in Table B.
Table 180: Compounds of the formulae I1, wherein A is a radical A2-N518 and $R^1$ has one of the meanings given in Table B.
Table 181: Compounds of the formulae I1, wherein A is a radical A2-N519 and $R^1$ has one of the meanings given in Table B.
Table 182: Compounds of the formulae I1, wherein A is a radical A2-N520 and $R^1$ has one of the meanings given in Table B.
Table 183: Compounds of the formulae I1, wherein A is a radical A2-N547 and $R^1$ has one of the meanings given in Table B.
Table 184: Compounds of the formulae I1, wherein A is a radical A2-N548 and $R^1$ has one of the meanings given in Table B.
Table 185: Compounds of the formulae I1, wherein A is a radical A2-N549 and $R^1$ has one of the meanings given in Table B.
Table 186: Compounds of the formulae I1, wherein A is a radical A2-N550 and $R^1$ has one of the meanings given in Table B.
Table 187: Compounds of the formulae I1, wherein A is a radical A2-N551 and $R^1$ has one of the meanings given in Table B.
Table 188: Compounds of the formulae I1, wherein A is a radical A2-N552 and $R^1$ has one of the meanings given in Table B.
Table 189: Compounds of the formulae I1, wherein A is a radical A2-N553 and $R^1$ has one of the meanings given in Table B.
Table 190: Compounds of the formulae I1, wherein A is a radical A2-N554 and $R^1$ has one of the meanings given in Table B.
Table 191: Compounds of the formulae I1, wherein A is a radical A2-N555 and $R^1$ has one of the meanings given in Table B.
Table 192: Compounds of the formulae I1, wherein A is a radical A2-N556 and $R^1$ has one of the meanings given in Table B.
Table 193: Compounds of the formulae I1, wherein A is a radical A2-N557 and $R^1$ has one of the meanings given in Table B.
Table 194: Compounds of the formulae I1, wherein A is a radical A2-N558 and $R^1$ has one of the meanings given in Table B.
Table 195: Compounds of the formulae I1, wherein A is a radical A2-N559 and $R^1$ has one of the meanings given in Table B.
Table 196: Compounds of the formulae I1, wherein A is a radical A2-N586 and $R^1$ has one of the meanings given in Table B.
Table 197: Compounds of the formulae I1, wherein A is a radical A2-N587 and $R^1$ has one of the meanings given in Table B.
Table 198: Compounds of the formulae I1, wherein A is a radical A2-N588 and $R^1$ has one of the meanings given in Table B.
Table 199: Compounds of the formulae I1, wherein A is a radical A2-N589 and $R^1$ has one of the meanings given in Table B.
Table 200: Compounds of the formulae I1, wherein A is a radical A2-N590 and $R^1$ has one of the meanings given in Table B.
Table 201: Compounds of the formulae I1, wherein A is a radical A2-N591 and $R^1$ has one of the meanings given in Table B.
Table 202: Compounds of the formulae I1, wherein A is a radical A2-N592 and $R^1$ has one of the meanings given in Table B.
Table 203: Compounds of the formulae I1, wherein A is a radical A2-N593 and $R^1$ has one of the meanings given in Table B.
Table 204: Compounds of the formulae I1, wherein A is a radical A2-N594 and $R^1$ has one of the meanings given in Table B.
Table 205: Compounds of the formulae I1, wherein A is a radical A2-N595 and $R^1$ has one of the meanings given in Table B.

Table 206: Compounds of the formulae I1, wherein A is a radical A2-N596 and R¹ has one of the meanings given in Table B.
Table 207: Compounds of the formulae I1, wherein A is a radical A2-N597 and R¹ has one of the meanings given in Table B.
Table 208: Compounds of the formulae I1, wherein A is a radical A2-N598 and R¹ has one of the meanings given in Table B.
Table 209: Compounds of the formulae I1, wherein A is a radical A2-N625 and R¹ has one of the meanings given in Table B.
Table 210: Compounds of the formulae I1, wherein A is a radical A2-N626 and R¹ has one of the meanings given in Table B.
Table 211: Compounds of the formulae I1, wherein A is a radical A2-N627 and R¹ has one of the meanings given in Table B.
Table 212: Compounds of the formulae I1, wherein A is a radical A2-N628 and R¹ has one of the meanings given in Table B.
Table 213: Compounds of the formulae I1, wherein A is a radical A2-N629 and R¹ has one of the meanings given in Table B.
Table 214: Compounds of the formulae I1, wherein A is a radical A2-N630 and R¹ has one of the meanings given in Table B.
Table 215: Compounds of the formulae I1, wherein A is a radical A2-N631 and R¹ has one of the meanings given in Table B.
Table 216: Compounds of the formulae I1, wherein A is a radical A2-N632 and R¹ has one of the meanings given in Table B.
Table 217: Compounds of the formulae I1, wherein A is a radical A2-N633 and R¹ has one of the meanings given in Table B.
Table 218: Compounds of the formulae I1, wherein A is a radical A2-N634 and R¹ has one of the meanings given in Table B.
Table 219: Compounds of the formulae I1, wherein A is a radical A2-N635 and R¹ has one of the meanings given in Table B.
Table 220: Compounds of the formulae I1, wherein A is a radical A2-N636 and R¹ has one of the meanings given in Table B.
Table 221: Compounds of the formulae I1, wherein A is a radical A2-N637 and R¹ has one of the meanings given in Table B.
Table 222: Compounds of the formulae I1, wherein A is a radical A2-N664 and R¹ has one of the meanings given in Table B.
Table 223: Compounds of the formulae I1, wherein A is a radical A2-N665 and R¹ has one of the meanings given in Table B.
Table 224: Compounds of the formulae I1, wherein A is a radical A2-N666 and R¹ has one of the meanings given in Table B.
Table 225: Compounds of the formulae I1, wherein A is a radical A2-N667 and R¹ has one of the meanings given in Table B.
Table 226: Compounds of the formulae I1, wherein A is a radical A2-N668 and R¹ has one of the meanings given in Table B.
Table 227: Compounds of the formulae I1, wherein A is a radical A2-N669 and R¹ has one of the meanings given in Table B.
Table 228: Compounds of the formulae I1, wherein A is a radical A2-N670 and R¹ has one of the meanings given in Table B.
Table 229: Compounds of the formulae I1, wherein A is a radical A2-N671 and R¹ has one of the meanings given in Table B.
Table 230: Compounds of the formulae I1, wherein A is a radical A2-N672 and R¹ has one of the meanings given in Table B.
Table 231: Compounds of the formulae I1, wherein A is a radical A2-N673 and R¹ has one of the meanings given in Table B.
Table 232: Compounds of the formulae I1, wherein A is a radical A2-N674 and R¹ has one of the meanings given in Table B.
Table 233: Compounds of the formulae I1, wherein A is a radical A2-N675 and R¹ has one of the meanings given in Table B.
Table 234: Compounds of the formulae I1, wherein A is a radical A2-N676 and R¹ has one of the meanings given in Table B.
Table 235: Compounds of the formulae I1, wherein A is a radical A2-N703 and R¹ has one of the meanings given in Table B.
Table 236: Compounds of the formulae I1, wherein A is a radical A2-N704 and R¹ has one of the meanings given in Table B.
Table 237: Compounds of the formulae I1, wherein A is a radical A2-N705 and R¹ has one of the meanings given in Table B.
Table 238: Compounds of the formulae I1, wherein A is a radical A2-N706 and R¹ has one of the meanings given in Table B.
Table 239: Compounds of the formulae I1, wherein A is a radical A2-N707 and R¹ has one of the meanings given in Table B.
Table 240: Compounds of the formulae I1, wherein A is a radical A2-N708 and R¹ has one of the meanings given in Table B.
Table 241: Compounds of the formulae I1, wherein A is a radical A2-N709 and R¹ has one of the meanings given in Table B.
Table 242: Compounds of the formulae I1, wherein A is a radical A2-N710 and R¹ has one of the meanings given in Table B.
Table 243: Compounds of the formulae I1, wherein A is a radical A2-N711 and R¹ has one of the meanings given in Table B.
Table 244: Compounds of the formulae I1, wherein A is a radical A2-N712 and R¹ has one of the meanings given in Table B.
Table 245: Compounds of the formulae I1, wherein A is a radical A2-N713 and R¹ has one of the meanings given in Table B.
Table 246: Compounds of the formulae I1, wherein A is a radical A2-N714 and R¹ has one of the meanings given in Table B.
Table 247: Compounds of the formulae I1, wherein A is a radical A2-N715 and R¹ has one of the meanings given in Table B.
Table 248: Compounds of the formulae I1, wherein A is a radical A2-N742 and R¹ has one of the meanings given in Table B.
Table 249: Compounds of the formulae I1, wherein A is a radical A2-N743 and R¹ has one of the meanings given in Table B.

Table 250: Compounds of the formulae I1, wherein A is a radical A2-N744 and R$^1$ has one of the meanings given in Table B.
Table 251: Compounds of the formulae I1, wherein A is a radical A2-N745 and R$^1$ has one of the meanings given in Table B.
Table 252: Compounds of the formulae I1, wherein A is a radical A2-N746 and R$^1$ has one of the meanings given in Table B.
Table 253: Compounds of the formulae I1, wherein A is a radical A2-N747 and R$^1$ has one of the meanings given in Table B.
Table 254: Compounds of the formulae I1, wherein A is a radical A2-N748 and R$^1$ has one of the meanings given in Table B.
Table 255: Compounds of the formulae I1, wherein A is a radical A2-N749 and R$^1$ has one of the meanings given in Table B.
Table 256: Compounds of the formulae I1, wherein A is a radical A2-N750 and R$^1$ has one of the meanings given in Table B.
Table 257: Compounds of the formulae I1, wherein A is a radical A2-N751 and R$^1$ has one of the meanings given in Table B.
Table 258: Compounds of the formulae I1, wherein A is a radical A2-N752 and R$^1$ has one of the meanings given in Table B.
Table 259: Compounds of the formulae I1, wherein A is a radical A2-N753 and R$^1$ has one of the meanings given in Table B.
Table 260: Compounds of the formulae I1, wherein A is a radical A2-N754 and R$^1$ has one of the meanings given in Table B.
Table 261: Compounds of the formulae I1, wherein A is a radical A2-N781 and R$^1$ has one of the meanings given in Table B.
Table 262: Compounds of the formulae I1, wherein A is a radical A2-N782 and R$^1$ has one of the meanings given in Table B.
Table 263: Compounds of the formulae I1, wherein A is a radical A2-N783 and R$^1$ has one of the meanings given in Table B.
Table 264: Compounds of the formulae I1, wherein A is a radical A2-N784 and R$^1$ has one of the meanings given in Table B.
Table 265: Compounds of the formulae I1, wherein A is a radical A2-N785 and R$^1$ has one of the meanings given in Table B.
Table 266: Compounds of the formulae I1, wherein A is a radical A2-N786 and R$^1$ has one of the meanings given in Table B.
Table 267: Compounds of the formulae I1, wherein A is a radical A2-N787 and R$^1$ has one of the meanings given in Table B.
Table 268: Compounds of the formulae I1, wherein A is a radical A2-N788 and R$^1$ has one of the meanings given in Table B.
Table 269: Compounds of the formulae I1, wherein A is a radical A2-N789 and R$^1$ has one of the meanings given in Table B.
Table 270: Compounds of the formulae I1, wherein A is a radical A2-N790 and R$^1$ has one of the meanings given in Table B.
Table 271: Compounds of the formulae I1, wherein A is a radical A2-N791 and R$^1$ has one of the meanings given in Table B.
Table 272: Compounds of the formulae I1, wherein A is a radical A2-N792 and R$^1$ has one of the meanings given in Table B.
Table 273: Compounds of the formulae I1, wherein A is a radical A2-N793 and R$^1$ has one of the meanings given in Table B.
Table 274: Compounds of the formulae I1, wherein A is a radical A2-N820 and R$^1$ has one of the meanings given in Table B.
Table 275: Compounds of the formulae I1, wherein A is a radical A2-N821 and R$^1$ has one of the meanings given in Table B.
Table 276: Compounds of the formulae I1, wherein A is a radical A2-N822 and R$^1$ has one of the meanings given in Table B.
Table 277: Compounds of the formulae I1, wherein A is a radical A2-N823 and R$^1$ has one of the meanings given in Table B.
Table 278: Compounds of the formulae I1, wherein A is a radical A2-N824 and R$^1$ has one of the meanings given in Table B.
Table 279: Compounds of the formulae I1, wherein A is a radical A2-N825 and R$^1$ has one of the meanings given in Table B.
Table 280: Compounds of the formulae I1, wherein A is a radical A2-N826 and R$^1$ has one of the meanings given in Table B.
Table 281: Compounds of the formulae I1, wherein A is a radical A2-N827 and R$^1$ has one of the meanings given in Table B.
Table 282: Compounds of the formulae I1, wherein A is a radical A2-N828 and R$^1$ has one of the meanings given in Table B.
Table 283: Compounds of the formulae I1, wherein A is a radical A2-N829 and R$^1$ has one of the meanings given in Table B.
Table 284: Compounds of the formulae I1, wherein A is a radical A2-N830 and R$^1$ has one of the meanings given in Table B.
Table 285: Compounds of the formulae I1, wherein A is a radical A2-N831 and R$^1$ has one of the meanings given in Table B.
Table 286: Compounds of the formulae I1, wherein A is a radical A2-N832 and R$^1$ has one of the meanings given in Table B.
Table 287: Compounds of the formulae I1, wherein A is a radical A2-N859 and R$^1$ has one of the meanings given in Table B.
Table 288: Compounds of the formulae I1, wherein A is a radical A2-N860 and R$^1$ has one of the meanings given in Table B.
Table 289: Compounds of the formulae I1, wherein A is a radical A2-N861 and R$^1$ has one of the meanings given in Table B.
Table 290: Compounds of the formulae I1, wherein A is a radical A2-N862 and R$^1$ has one of the meanings given in Table B.
Table 291: Compounds of the formulae I1, wherein A is a radical A2-N863 and R$^1$ has one of the meanings given in Table B.
Table 292: Compounds of the formulae I1, wherein A is a radical A2-N864 and R$^1$ has one of the meanings given in Table B.
Table 293: Compounds of the formulae I1, wherein A is a radical A2-N865 and R$^1$ has one of the meanings given in Table B.

Table 294: Compounds of the formulae I1, wherein A is a radical A2-N866 and $R^1$ has one of the meanings given in Table B.
Table 295: Compounds of the formulae I1, wherein A is a radical A2-N867 and $R^1$ has one of the meanings given in Table B.
Table 296: Compounds of the formulae I1, wherein A is a radical A2-N868 and $R^1$ has one of the meanings given in Table B.
Table 297: Compounds of the formulae I1, wherein A is a radical A2-N869 and $R^1$ has one of the meanings given in Table B.
Table 298: Compounds of the formulae I1, wherein A is a radical A2-N870 and $R^1$ has one of the meanings given in Table B.
Table 299: Compounds of the formulae I1, wherein A is a radical A2-N871 and $R^1$ has one of the meanings given in Table B.
Table 300: Compounds of the formulae I1, wherein A is a radical A2-N898 and $R^1$ has one of the meanings given in Table B.
Table 301: Compounds of the formulae I1, wherein A is a radical A2-N899 and $R^1$ has one of the meanings given in Table B.
Table 302: Compounds of the formulae I1, wherein A is a radical A2-N900 and $R^1$ has one of the meanings given in Table B.
Table 303: Compounds of the formulae I1, wherein A is a radical A2-N901 and $R^1$ has one of the meanings given in Table B.
Table 304: Compounds of the formulae I1, wherein A is a radical A2-N902 and $R^1$ has one of the meanings given in Table B.
Table 305: Compounds of the formulae I1, wherein A is a radical A2-N903 and $R^1$ has one of the meanings given in Table B.
Table 306: Compounds of the formulae I1, wherein A is a radical A2-N904 and $R^1$ has one of the meanings given in Table B.
Table 307: Compounds of the formulae I1, wherein A is a radical A2-N905 and $R^1$ has one of the meanings given in Table B.
Table 308: Compounds of the formulae I1, wherein A is a radical A2-N906 and $R^1$ has one of the meanings given in Table B.
Table 309: Compounds of the formulae I1, wherein A is a radical A2-N907 and $R^1$ has one of the meanings given in Table B.
Table 310: Compounds of the formulae I1, wherein A is a radical A2-N908 and $R^1$ has one of the meanings given in Table B.
Table 311: Compounds of the formulae I1, wherein A is a radical A2-N909 and $R^1$ has one of the meanings given in Table B.
Table 312: Compounds of the formulae I1, wherein A is a radical A2-N910 and $R^1$ has one of the meanings given in Table B.
Table 313: Compounds of the formulae I1, wherein A is a radical A2-N937 and $R^1$ has one of the meanings given in Table B.
Table 314: Compounds of the formulae I1, wherein A is a radical A2-N938 and $R^1$ has one of the meanings given in Table B.
Table 315: Compounds of the formulae I1, wherein A is a radical A2-N939 and $R^1$ has one of the meanings given in Table B.
Table 316: Compounds of the formulae I1, wherein A is a radical A2-N940 and $R^1$ has one of the meanings given in Table B.
Table 317: Compounds of the formulae I1, wherein A is a radical A2-N941 and $R^1$ has one of the meanings given in Table B.
Table 318: Compounds of the formulae I1, wherein A is a radical A2-N942 and $R^1$ has one of the meanings given in Table B.
Table 319: Compounds of the formulae I1, wherein A is a radical A2-N943 and $R^1$ has one of the meanings given in Table B.
Table 320: Compounds of the formulae I1, wherein A is a radical A2-N944 and $R^1$ has one of the meanings given in Table B.
Table 321: Compounds of the formulae I1, wherein A is a radical A2-N945 and $R^1$ has one of the meanings given in Table B.
Table 322: Compounds of the formulae I1, wherein A is a radical A2-N946 and $R^1$ has one of the meanings given in Table B.
Table 323: Compounds of the formulae I1, wherein A is a radical A2-N947 and $R^1$ has one of the meanings given in Table B.
Table 324: Compounds of the formulae I1, wherein A is a radical A2-N948 and $R^1$ has one of the meanings given in Table B.
Table 325: Compounds of the formulae I1, wherein A is a radical A2-N949 and $R^1$ has one of the meanings given in Table B.
Table 326: Compounds of the formulae I1, wherein A is a radical A2-N976 and $R^1$ has one of the meanings given in Table B.
Table 327: Compounds of the formulae I1, wherein A is a radical A2-N977 and $R^1$ has one of the meanings given in Table B.
Table 328: Compounds of the formulae I1, wherein A is a radical A2-N978 and $R^1$ has one of the meanings given in Table B.
Table 329: Compounds of the formulae I1, wherein A is a radical A2-N979 and $R^1$ has one of the meanings given in Table B.
Table 330: Compounds of the formulae I1, wherein A is a radical A2-N980 and $R^1$ has one of the meanings given in Table B.
Table 331: Compounds of the formulae I1, wherein A is a radical A2-N981 and $R^1$ has one of the meanings given in Table B.
Table 332: Compounds of the formulae I1, wherein A is a radical A2-N982 and $R^1$ has one of the meanings given in Table B.
Table 333: Compounds of the formulae I1, wherein A is a radical A2-N983 and $R^1$ has one of the meanings given in Table B.
Table 334: Compounds of the formulae I1, wherein A is a radical A2-N984 and $R^1$ has one of the meanings given in Table B.
Table 335: Compounds of the formulae I1, wherein A is a radical A2-N985 and $R^1$ has one of the meanings given in Table B.
Table 336: Compounds of the formulae I1, wherein A is a radical A2-N986 and $R^1$ has one of the meanings given in Table B.
Table 337: Compounds of the formulae I1, wherein A is a radical A2-N987 and $R^1$ has one of the meanings given in Table B.

Table 338: Compounds of the formulae I1, wherein A is a radical A2-N988 and $R^1$ has one of the meanings given in Table B.

TABLE B

| No. | Radical $R^1$ |
|---|---|
| 1 | $CH_3$ |
| 2 | $CH_2CH_3$ |
| 3 | $CH_2CH_2CH_3$ |
| 4 | $CH_2(CH_3)_2$ |
| 5 | $CH_2CH_2CH_2CH_3$ |
| 6 | $C(CH_3)_3$ |
| 7 | $CH_2CH(CH_3)_2$ |
| 8 | $CH(CH_3)CH_2CH_3$ |
| 9 | $CH_2CH_2OCH_3$ |
| 10 | $CH_2CH_2OCH_2CH_3$ |
| 11 | $CH(OCH_3)CH_3$ |
| 12 | $CH(OCH_2CH_3)CH_3$ |
| 13 | cyclopropylmethyl |
| 14 | $CH_2CN$ |
| 15 | $CH(CN)CH_3$ |
| 16 | $CH_2CH_2(CN)$ |
| 17 | $CH_2CH=CH_2$ |
| 18 | cyclopropyl |
| 19 | $CH_2CF_3$ |
| 20 | pyridin-2-ylmethyl |
| 21 | pyridin-3-ylmethyl |
| 22 | pyridin-4-ylmethyl |
| 23 | furan-2-ylmethyl |
| 24 | furan-3-ylmethyl |
| 25 | thiophen-2-ylmethyl |
| 26 | thiophen-3-ylmethyl |
| 27 | tetrahydrofuran-2-ylmethyl |
| 28 | tetrahydrofuran-3-ylmethyl |
| 29 | pyrrol-2-ylmethyl |
| 30 | pyrrol-3-ylmethyl |
| 31 | 1-methylpyrrol-3-ylmethyl |
| 32 | 1-methylpyrrol-2-ylmethyl |
| 33 | $CH_2C_6H_5$ |
| 34 | cis-2-buten-1-yl |
| 35 | trans-2-buten-1-yl |
| 36 | $CH_2C\equiv CH$ |
| 37 | $CH_2C\equiv CCH_3$ |

A very preferred embodiment of the invention relates to compounds of the formula I1 and to the salts thereof, the N-oxides thereof and the salts of the N-oxides thereof, wherein A is a radical A8.

Within this embodiment, very particular preference is further given to the compounds of formula I1, wherein A is a radical A8 selected from the radicals A8-1, A8-2 and A8-3, and particularly selected from the radicals A8-1.1 to A8-1.173, A8-2.1 to A8-2.131 and A8-3.1 to A8-3.13.

Examples of compounds of this particularly preferred embodiment are the compounds given in the following tables 339 to 655 The groups mentioned for a substituent in the tables are furthermore per se, independently of the combination in which they are mentioned, a particularly preferred aspect of the substituent in question.

Table 339: Compounds of the formula I1 wherein A is a radical A8-1.1 and $R^1$ has one of the meanings given in Table B.
Table 340: Compounds of the formula I1 wherein A is a radical A8-1.2 and $R^1$ has one of the meanings given in Table B.
Table 341: Compounds of the formula I1 wherein A is a radical A8-1.3 and $R^1$ has one of the meanings given in Table B.
Table 342: Compounds of the formula I1 wherein A is a radical A8-1.4 and $R^1$ has one of the meanings given in Table B.
Table 343: Compounds of the formula I1 wherein A is a radical A8-1.5 and $R^1$ has one of the meanings given in Table B.
Table 344: Compounds of the formula I1 wherein A is a radical A8-1.6 and $R^1$ has one of the meanings given in Table B.
Table 345: Compounds of the formula I1 wherein A is a radical A8-1.7 and $R^1$ has one of the meanings given in Table B.
Table 346: Compounds of the formula I1 wherein A is a radical A8-1.8 and $R^1$ has one of the meanings given in Table B.
Table 347: Compounds of the formula I1 wherein A is a radical A8-1.9 and $R^1$ has one of the meanings given in Table B.
Table 348: Compounds of the formula I1 wherein A is a radical A8-1.10 and $R^1$ has one of the meanings given in Table B.
Table 349: Compounds of the formula I1 wherein A is a radical A8-1.11 and $R^1$ has one of the meanings given in Table B.
Table 350: Compounds of the formula I1 wherein A is a radical A8-1.12 and $R^1$ has one of the meanings given in Table B.
Table 351: Compounds of the formula I1 wherein A is a radical A8-1.13 and $R^1$ has one of the meanings given in Table B.
Table 352: Compounds of the formula I1 wherein A is a radical A8-1.14 and $R^1$ has one of the meanings given in Table B.
Table 353: Compounds of the formula I1 wherein A is a radical A8-1.15 and $R^1$ has one of the meanings given in Table B.
Table 354: Compounds of the formula I1 wherein A is a radical A8-1.16 and $R^1$ has one of the meanings given in Table B.
Table 355: Compounds of the formula I1 wherein A is a radical A8-1.17 and $R^1$ has one of the meanings given in Table B.
Table 356: Compounds of the formula I1 wherein A is a radical A8-1.18 and $R^1$ has one of the meanings given in Table B.
Table 357: Compounds of the formula I1 wherein A is a radical A8-1.19 and $R^1$ has one of the meanings given in Table B.
Table 358: Compounds of the formula I1 wherein A is a radical A8-1.20 and $R^1$ has one of the meanings given in Table B.
Table 359: Compounds of the formula I1 wherein A is a radical A8-1.21 and $R^1$ has one of the meanings given in Table B.
Table 360: Compounds of the formula I1 wherein A is a radical A8-1.22 and $R^1$ has one of the meanings given in Table B.
Table 361: Compounds of the formula I1 wherein A is a radical A8-1.23 and $R^1$ has one of the meanings given in Table B.
Table 362: Compounds of the formula I1 wherein A is a radical A8-1.24 and $R^1$ has one of the meanings given in Table B.
Table 363: Compounds of the formula I1 wherein A is a radical A8-1.25 and $R^1$ has one of the meanings given in Table B.
Table 364: Compounds of the formula I1 wherein A is a radical A8-1.26 and $R^1$ has one of the meanings given in Table B.
Table 365: Compounds of the formula I1 wherein A is a radical A8-1.27 and $R^1$ has one of the meanings given in Table B.

Table 366: Compounds of the formula I1 wherein A is a radical A8-1.28 and $R^1$ has one of the meanings given in Table B.
Table 367: Compounds of the formula I1 wherein A is a radical A8-1.29 and $R^1$ has one of the meanings given in Table B.
Table 368: Compounds of the formula I1 wherein A is a radical A8-1.30 and $R^1$ has one of the meanings given in Table B.
Table 369: Compounds of the formula I1 wherein A is a radical A8-1.31 and $R^1$ has one of the meanings given in Table B.
Table 370: Compounds of the formula I1 wherein A is a radical A8-1.32 and $R^1$ has one of the meanings given in Table B.
Table 371: Compounds of the formula I1 wherein A is a radical A8-1.33 and $R^1$ has one of the meanings given in Table B.
Table 372: Compounds of the formula I1 wherein A is a radical A8-1.34 and $R^1$ has one of the meanings given in Table B.
Table 373: Compounds of the formula I1 wherein A is a radical A8-1.35 and $R^1$ has one of the meanings given in Table B.
Table 374: Compounds of the formula I1 wherein A is a radical A8-1.36 and $R^1$ has one of the meanings given in Table B.
Table 375: Compounds of the formula I1 wherein A is a radical A8-1.37 and $R^1$ has one of the meanings given in Table B.
Table 376: Compounds of the formula I1 wherein A is a radical A8-1.38 and $R^1$ has one of the meanings given in Table B.
Table 377: Compounds of the formula I1 wherein A is a radical A8-1.39 and $R^1$ has one of the meanings given in Table B.
Table 378: Compounds of the formula I1 wherein A is a radical A8-1.40 and $R^1$ has one of the meanings given in Table B.
Table 379: Compounds of the formula I1 wherein A is a radical A8-1.41 and $R^1$ has one of the meanings given in Table B.
Table 380: Compounds of the formula I1 wherein A is a radical A8-1.42 and $R^1$ has one of the meanings given in Table B.
Table 381: Compounds of the formula I1 wherein A is a radical A8-1.43 and $R^1$ has one of the meanings given in Table B.
Table 382: Compounds of the formula I1 wherein A is a radical A8-1.44 and $R^1$ has one of the meanings given in Table B.
Table 383: Compounds of the formula I1 wherein A is a radical A8-1.45 and $R^1$ has one of the meanings given in Table B.
Table 384: Compounds of the formula I1 wherein A is a radical A8-1.46 and $R^1$ has one of the meanings given in Table B.
Table 385: Compounds of the formula I1 wherein A is a radical A8-1.47 and $R^1$ has one of the meanings given in Table B.
Table 386: Compounds of the formula I1 wherein A is a radical A8-1.48 and $R^1$ has one of the meanings given in Table B.
Table 387: Compounds of the formula I1 wherein A is a radical A8-1.49 and $R^1$ has one of the meanings given in Table B.
Table 388: Compounds of the formula I1 wherein A is a radical A8-1.50 and $R^1$ has one of the meanings given in Table B.
Table 389: Compounds of the formula I1 wherein A is a radical A8-1.51 and $R^1$ has one of the meanings given in Table B.
Table 390: Compounds of the formula I1 wherein A is a radical A8-1.52 and $R^1$ has one of the meanings given in Table B.
Table 391: Compounds of the formula I1 wherein A is a radical A8-1.53 and $R^1$ has one of the meanings given in Table B.
Table 392: Compounds of the formula I1 wherein A is a radical A8-1.54 and $R^1$ has one of the meanings given in Table B.
Table 393: Compounds of the formula I1 wherein A is a radical A8-1.55 and $R^1$ has one of the meanings given in Table B.
Table 394: Compounds of the formula I1 wherein A is a radical A8-1.56 and $R^1$ has one of the meanings given in Table B.
Table 395: Compounds of the formula I1 wherein A is a radical A8-1.57 and $R^1$ has one of the meanings given in Table B.
Table 396: Compounds of the formula I1 wherein A is a radical A8-1.58 and $R^1$ has one of the meanings given in Table B.
Table 397: Compounds of the formula I1 wherein A is a radical A8-1.59 and $R^1$ has one of the meanings given in Table B.
Table 398: Compounds of the formula I1 wherein A is a radical A8-1.60 and $R^1$ has one of the meanings given in Table B.
Table 399: Compounds of the formula I1 wherein A is a radical A8-1.61 and $R^1$ has one of the meanings given in Table B.
Table 400: Compounds of the formula I1 wherein A is a radical A8-1.62 and $R^1$ has one of the meanings given in Table B.
Table 401: Compounds of the formula I1 wherein A is a radical A8-1.63 and $R^1$ has one of the meanings given in Table B.
Table 402: Compounds of the formula I1 wherein A is a radical A8-1.64 and $R^1$ has one of the meanings given in Table B.
Table 403: Compounds of the formula I1 wherein A is a radical A8-1.65 and $R^1$ has one of the meanings given in Table B.
Table 404: Compounds of the formula I1 wherein A is a radical A8-1.66 and $R^1$ has one of the meanings given in Table B.
Table 405: Compounds of the formula I1 wherein A is a radical A8-1.67 and $R^1$ has one of the meanings given in Table B.
Table 406: Compounds of the formula I1 wherein A is a radical A8-1.68 and $R^1$ has one of the meanings given in Table B.
Table 407: Compounds of the formula I1 wherein A is a radical A8-1.69 and $R^1$ has one of the meanings given in Table B.
Table 408: Compounds of the formula I1 wherein A is a radical A8-1.70 and $R^1$ has one of the meanings given in Table B.
Table 409: Compounds of the formula I1 wherein A is a radical A8-1.71 and $R^1$ has one of the meanings given in Table B.

Table 410: Compounds of the formula I1 wherein A is a radical A8-1.72 and $R^1$ has one of the meanings given in Table B.
Table 411: Compounds of the formula I1 wherein A is a radical A8-1.73 and $R^1$ has one of the meanings given in Table B.
Table 412: Compounds of the formula I1 wherein A is a radical A8-1.74 and $R^1$ has one of the meanings given in Table B.
Table 413: Compounds of the formula I1 wherein A is a radical A8-1.75 and $R^1$ has one of the meanings given in Table B.
Table 414: Compounds of the formula I1 wherein A is a radical A8-1.76 and $R^1$ has one of the meanings given in Table B.
Table 415: Compounds of the formula I1 wherein A is a radical A8-1.77 and $R^1$ has one of the meanings given in Table B.
Table 416: Compounds of the formula I1 wherein A is a radical A8-1.78 and $R^1$ has one of the meanings given in Table B.
Table 417: Compounds of the formula I1 wherein A is a radical A8-1.79 and $R^1$ has one of the meanings given in Table B.
Table 418: Compounds of the formula I1 wherein A is a radical A8-1.80 and $R^1$ has one of the meanings given in Table B.
Table 419: Compounds of the formula I1 wherein A is a radical A8-1.81 and $R^1$ has one of the meanings given in Table B.
Table 420: Compounds of the formula I1 wherein A is a radical A8-1.82 and $R^1$ has one of the meanings given in Table B.
Table 421: Compounds of the formula I1 wherein A is a radical A8-1.83 and $R^1$ has one of the meanings given in Table B.
Table 422: Compounds of the formula I1 wherein A is a radical A8-1.84 and $R^1$ has one of the meanings given in Table B.
Table 423: Compounds of the formula I1 wherein A is a radical A8-1.85 and $R^1$ has one of the meanings given in Table B.
Table 424: Compounds of the formula I1 wherein A is a radical A8-1.86 and $R^1$ has one of the meanings given in Table B.
Table 425: Compounds of the formula I1 wherein A is a radical A8-1.87 and $R^1$ has one of the meanings given in Table B.
Table 426: Compounds of the formula I1 wherein A is a radical A8-1.88 and $R^1$ has one of the meanings given in Table B.
Table 427: Compounds of the formula I1 wherein A is a radical A8-1.89 and $R^1$ has one of the meanings given in Table B.
Table 428: Compounds of the formula I1 wherein A is a radical A8-1.90 and $R^1$ has one of the meanings given in Table B.
Table 429: Compounds of the formula I1 wherein A is a radical A8-1.91 and $R^1$ has one of the meanings given in Table B.
Table 430: Compounds of the formula I1 wherein A is a radical A8-1.92 and $R^1$ has one of the meanings given in Table B.
Table 431: Compounds of the formula I1 wherein A is a radical A8-1.93 and $R^1$ has one of the meanings given in Table B.
Table 432: Compounds of the formula I1 wherein A is a radical A8-1.94 and $R^1$ has one of the meanings given in Table B.
Table 433: Compounds of the formula I1 wherein A is a radical A8-1.95 and $R^1$ has one of the meanings given in Table B.
Table 434: Compounds of the formula I1 wherein A is a radical A8-1.96 and $R^1$ has one of the meanings given in Table B.
Table 435: Compounds of the formula I1 wherein A is a radical A8-1.97 and $R^1$ has one of the meanings given in Table B.
Table 436: Compounds of the formula I1 wherein A is a radical A8-1.98 and $R^1$ has one of the meanings given in Table B.
Table 437: Compounds of the formula I1 wherein A is a radical A8-1.99 and $R^1$ has one of the meanings given in Table B.
Table 438: Compounds of the formula I1 wherein A is a radical A8-1.100 and $R^1$ has one of the meanings given in Table B.
Table 439: Compounds of the formula I1 wherein A is a radical A8-1.101 and $R^1$ has one of the meanings given in Table B.
Table 440: Compounds of the formula I1 wherein A is a radical A8-1.102 and $R^1$ has one of the meanings given in Table B.
Table 441: Compounds of the formula I1 wherein A is a radical A8-1.103 and $R^1$ has one of the meanings given in Table B.
Table 442: Compounds of the formula I1 wherein A is a radical A8-1.104 and $R^1$ has one of the meanings given in Table B.
Table 443: Compounds of the formula I1 wherein A is a radical A8-1.105 and $R^1$ has one of the meanings given in Table B.
Table 444: Compounds of the formula I1 wherein A is a radical A8-1.106 and $R^1$ has one of the meanings given in Table B.
Table 445: Compounds of the formula I1 wherein A is a radical A8-1.107 and $R^1$ has one of the meanings given in Table B.
Table 446: Compounds of the formula I1 wherein A is a radical A8-1.108 and $R^1$ has one of the meanings given in Table B.
Table 447: Compounds of the formula I1 wherein A is a radical A8-1.109 and $R^1$ has one of the meanings given in Table B.
Table 448: Compounds of the formula I1 wherein A is a radical A8-1.110 and $R^1$ has one of the meanings given in Table B.
Table 449: Compounds of the formula I1 wherein A is a radical A8-1.111 and $R^1$ has one of the meanings given in Table B.
Table 450: Compounds of the formula I1 wherein A is a radical A8-1.112 and $R^1$ has one of the meanings given in Table B.
Table 451: Compounds of the formula I1 wherein A is a radical A8-1.113 and $R^1$ has one of the meanings given in Table B.
Table 452: Compounds of the formula I1 wherein A is a radical A8-1.114 and $R^1$ has one of the meanings given in Table B.
Table 453: Compounds of the formula I1 wherein A is a radical A8-1.115 and $R^1$ has one of the meanings given in Table B.

Table 454: Compounds of the formula I1 wherein A is a radical A8-1.116 and $R^1$ has one of the meanings given in Table B.
Table 455: Compounds of the formula I1 wherein A is a radical A8-1.117 and $R^1$ has one of the meanings given in Table B.
Table 456: Compounds of the formula I1 wherein A is a radical A8-1.118 and $R^1$ has one of the meanings given in Table B.
Table 457: Compounds of the formula I1 wherein A is a radical A8-1.119 and $R^1$ has one of the meanings given in Table B.
Table 458: Compounds of the formula I1 wherein A is a radical A8-1.120 and $R^1$ has one of the meanings given in Table B.
Table 459: Compounds of the formula I1 wherein A is a radical A8-1.121 and $R^1$ has one of the meanings given in Table B.
Table 460: Compounds of the formula I1 wherein A is a radical A8-1.122 and $R^1$ has one of the meanings given in Table B.
Table 461: Compounds of the formula I1 wherein A is a radical A8-1.123 and $R^1$ has one of the meanings given in Table B.
Table 462: Compounds of the formula I1 wherein A is a radical A8-1.124 and $R^1$ has one of the meanings given in Table B.
Table 463: Compounds of the formula I1 wherein A is a radical A8-1.125 and $R^1$ has one of the meanings given in Table B.
Table 464: Compounds of the formula I1 wherein A is a radical A8-1.126 and $R^1$ has one of the meanings given in Table B.
Table 465: Compounds of the formula I1 wherein A is a radical A8-1.127 and $R^1$ has one of the meanings given in Table B.
Table 466: Compounds of the formula I1 wherein A is a radical A8-1.128 and $R^1$ has one of the meanings given in Table B.
Table 467: Compounds of the formula I1 wherein A is a radical A8-1.129 and $R^1$ has one of the meanings given in Table B.
Table 468: Compounds of the formula I1 wherein A is a radical A8-1.130 and $R^1$ has one of the meanings given in Table B.
Table 469: Compounds of the formula I1 wherein A is a radical A8-1.131 and $R^1$ has one of the meanings given in Table B.
Table 470: Compounds of the formula I1 wherein A is a radical A8-1.132 and $R^1$ has one of the meanings given in Table B.
Table 471: Compounds of the formula I1 wherein A is a radical A8-1.133 and $R^1$ has one of the meanings given in Table B.
Table 472: Compounds of the formula I1 wherein A is a radical A8-1.134 and $R^1$ has one of the meanings given in Table B.
Table 473: Compounds of the formula I1 wherein A is a radical A8-1.135 and $R^1$ has one of the meanings given in Table B.
Table 474: Compounds of the formula I1 wherein A is a radical A8-1.136 and $R^1$ has one of the meanings given in Table B.
Table 475: Compounds of the formula I1 wherein A is a radical A8-1.137 and $R^1$ has one of the meanings given in Table B.
Table 476: Compounds of the formula I1 wherein A is a radical A8-1.138 and $R^1$ has one of the meanings given in Table B.
Table 477: Compounds of the formula I1 wherein A is a radical A8-1.139 and $R^1$ has one of the meanings given in Table B.
Table 478: Compounds of the formula I1 wherein A is a radical A8-1.140 and $R^1$ has one of the meanings given in Table B.
Table 479: Compounds of the formula I1 wherein A is a radical A8-1.141 and $R^1$ has one of the meanings given in Table B.
Table 480: Compounds of the formula I1 wherein A is a radical A8-1.142 and $R^1$ has one of the meanings given in Table B.
Table 481: Compounds of the formula I1 wherein A is a radical A8-1.143 and $R^1$ has one of the meanings given in Table B.
Table 482: Compounds of the formula I1 wherein A is a radical A8-1.144 and $R^1$ has one of the meanings given in Table B.
Table 483: Compounds of the formula I1 wherein A is a radical A8-1.145 and $R^1$ has one of the meanings given in Table B.
Table 484: Compounds of the formula I1 wherein A is a radical A8-1.146 and $R^1$ has one of the meanings given in Table B.
Table 485: Compounds of the formula I1 wherein A is a radical A8-1.147 and $R^1$ has one of the meanings given in Table B.
Table 486: Compounds of the formula I1 wherein A is a radical A8-1.148 and $R^1$ has one of the meanings given in Table B.
Table 487: Compounds of the formula I1 wherein A is a radical A8-1.149 and $R^1$ has one of the meanings given in Table B.
Table 488: Compounds of the formula I1 wherein A is a radical A8-1.150 and $R^1$ has one of the meanings given in Table B.
Table 489: Compounds of the formula I1 wherein A is a radical A8-1.151 and $R^1$ has one of the meanings given in Table B.
Table 490: Compounds of the formula I1 wherein A is a radical A8-1.152 and $R^1$ has one of the meanings given in Table B.
Table 491: Compounds of the formula I1 wherein A is a radical A8-1.153 and $R^1$ has one of the meanings given in Table B.
Table 492: Compounds of the formula I1 wherein A is a radical A8-1.154 and $R^1$ has one of the meanings given in Table B.
Table 493: Compounds of the formula I1 wherein A is a radical A8-1.155 and $R^1$ has one of the meanings given in Table B.
Table 494: Compounds of the formula I1 wherein A is a radical A8-1.156 and $R^1$ has one of the meanings given in Table B.
Table 495: Compounds of the formula I1 wherein A is a radical A8-1.157 and $R^1$ has one of the meanings given in Table B.
Table 496: Compounds of the formula I1 wherein A is a radical A8-1.158 and $R^1$ has one of the meanings given in Table B.
Table 497: Compounds of the formula I1 wherein A is a radical A8-1.159 and $R^1$ has one of the meanings given in Table B.

Table 498: Compounds of the formula I1 wherein A is a radical A8-1.160 and $R^1$ has one of the meanings given in Table B.
Table 499: Compounds of the formula I1 wherein A is a radical A8-1.161 and $R^1$ has one of the meanings given in Table B.
Table 500: Compounds of the formula I1 wherein A is a radical A8-1.162 and $R^1$ has one of the meanings given in Table B.
Table 501: Compounds of the formula I1 wherein A is a radical A8-1.163 and $R^1$ has one of the meanings given in Table B.
Table 502: Compounds of the formula I1 wherein A is a radical A8-1.164 and $R^1$ has one of the meanings given in Table B.
Table 503: Compounds of the formula I1 wherein A is a radical A8-1.165 and $R^1$ has one of the meanings given in Table B.
Table 504: Compounds of the formula I1 wherein A is a radical A8-1.166 and $R^1$ has one of the meanings given in Table B.
Table 505: Compounds of the formula I1 wherein A is a radical A8-1.167 and $R^1$ has one of the meanings given in Table B.
Table 506: Compounds of the formula I1 wherein A is a radical A8-1.168 and $R^1$ has one of the meanings given in Table B.
Table 507: Compounds of the formula I1 wherein A is a radical A8-1.169 and $R^1$ has one of the meanings given in Table B.
Table 508: Compounds of the formula I1 wherein A is a radical A8-1.170 and $R^1$ has one of the meanings given in Table B.
Table 509: Compounds of the formula I1 wherein A is a radical A8-1.171 and $R^1$ has one of the meanings given in Table B.
Table 510: Compounds of the formula I1 wherein A is a radical A8-1.172 and $R^1$ has one of the meanings given in Table B.
Table 511: Compounds of the formula I1 wherein A is a radical A8-1.173 and $R^1$ has one of the meanings given in Table B.
Table 512: Compounds of the formula I1 wherein A is a radical A8-2.1 and $R^1$ has one of the meanings given in Table B.
Table 513: Compounds of the formula I1 wherein A is a radical A8-2.2 and $R^1$ has one of the meanings given in Table B.
Table 514: Compounds of the formula I1 wherein A is a radical A8-2.3 and $R^1$ has one of the meanings given in Table B.
Table 515: Compounds of the formula I1 wherein A is a radical A8-2.4 and $R^1$ has one of the meanings given in Table B.
Table 516: Compounds of the formula I1 wherein A is a radical A8-2.5 and $R^1$ has one of the meanings given in Table B.
Table 517: Compounds of the formula I1 wherein A is a radical A8-2.6 and $R^1$ has one of the meanings given in Table B.
Table 518: Compounds of the formula I1 wherein A is a radical A8-2.7 and $R^1$ has one of the meanings given in Table B.
Table 519: Compounds of the formula I1 wherein A is a radical A8-2.8 and $R^1$ has one of the meanings given in Table B.
Table 520: Compounds of the formula I1 wherein A is a radical A8-2.9 and $R^1$ has one of the meanings given in Table B.
Table 521: Compounds of the formula I1 wherein A is a radical A8-2.10 and $R^1$ has one of the meanings given in Table B.
Table 522: Compounds of the formula I1 wherein A is a radical A8-2.11 and $R^1$ has one of the meanings given in Table B.
Table 523: Compounds of the formula I1 wherein A is a radical A8-2.12 and $R^1$ has one of the meanings given in Table B.
Table 524: Compounds of the formula I1 wherein A is a radical A8-2.13 and $R^1$ has one of the meanings given in Table B.
Table 525: Compounds of the formula I1 wherein A is a radical A8-2.14 and $R^1$ has one of the meanings given in Table B.
Table 526: Compounds of the formula I1 wherein A is a radical A8-2.15 and $R^1$ has one of the meanings given in Table B.
Table 527: Compounds of the formula I1 wherein A is a radical A8-2.16 and $R^1$ has one of the meanings given in Table B.
Table 528: Compounds of the formula I1 wherein A is a radical A8-2.17 and $R^1$ has one of the meanings given in Table B.
Table 529: Compounds of the formula I1 wherein A is a radical A8-2.18 and $R^1$ has one of the meanings given in Table B.
Table 530: Compounds of the formula I1 wherein A is a radical A8-2.19 and $R^1$ has one of the meanings given in Table B.
Table 531: Compounds of the formula I1 wherein A is a radical A8-2.20 and $R^1$ has one of the meanings given in Table B.
Table 532: Compounds of the formula I1 wherein A is a radical A8-2.21 and $R^1$ has one of the meanings given in Table B.
Table 533: Compounds of the formula I1 wherein A is a radical A8-2.22 and $R^1$ has one of the meanings given in Table B.
Table 534: Compounds of the formula I1 wherein A is a radical A8-2.23 and $R^1$ has one of the meanings given in Table B.
Table 535: Compounds of the formula I1 wherein A is a radical A8-2.24 and $R^1$ has one of the meanings given in Table B.
Table 536: Compounds of the formula I1 wherein A is a radical A8-2.25 and $R^1$ has one of the meanings given in Table B.
Table 537: Compounds of the formula I1 wherein A is a radical A8-2.26 and $R^1$ has one of the meanings given in Table B.
Table 538: Compounds of the formula I1 wherein A is a radical A8-2.27 and $R^1$ has one of the meanings given in Table B.
Table 539: Compounds of the formula I1 wherein A is a radical A8-2.28 and $R^1$ has one of the meanings given in Table B.
Table 540: Compounds of the formula I1 wherein A is a radical A8-2.29 and $R^1$ has one of the meanings given in Table B.
Table 541: Compounds of the formula I1 wherein A is a radical A8-2.30 and $R^1$ has one of the meanings given in Table B.

Table 542: Compounds of the formula I1 wherein A is a radical A8-2.31 and $R^1$ has one of the meanings given in Table B.
Table 543: Compounds of the formula I1 wherein A is a radical A8-2.32 and $R^1$ has one of the meanings given in Table B.
Table 544: Compounds of the formula I1 wherein A is a radical A8-2.33 and $R^1$ has one of the meanings given in Table B.
Table 545: Compounds of the formula I1 wherein A is a radical A8-2.34 and $R^1$ has one of the meanings given in Table B.
Table 546: Compounds of the formula I1 wherein A is a radical A8-2.35 and $R^1$ has one of the meanings given in Table B.
Table 547: Compounds of the formula I1 wherein A is a radical A8-2.36 and $R^1$ has one of the meanings given in Table B.
Table 548: Compounds of the formula I1 wherein A is a radical A8-2.37 and $R^1$ has one of the meanings given in Table B.
Table 549: Compounds of the formula I1 wherein A is a radical A8-2.38 and $R^1$ has one of the meanings given in Table B.
Table 550: Compounds of the formula I1 wherein A is a radical A8-2.39 and $R^1$ has one of the meanings given in Table B.
Table 551: Compounds of the formula I1 wherein A is a radical A8-2.40 and $R^1$ has one of the meanings given in Table B.
Table 552: Compounds of the formula I1 wherein A is a radical A8-2.41 and $R^1$ has one of the meanings given in Table B.
Table 553: Compounds of the formula I1 wherein A is a radical A8-2.42 and $R^1$ has one of the meanings given in Table B.
Table 554: Compounds of the formula I1 wherein A is a radical A8-2.43 and $R^1$ has one of the meanings given in Table B.
Table 555: Compounds of the formula I1 wherein A is a radical A8-2.44 and $R^1$ has one of the meanings given in Table B.
Table 556: Compounds of the formula I1 wherein A is a radical A8-2.45 and $R^1$ has one of the meanings given in Table B.
Table 557: Compounds of the formula I1 wherein A is a radical A8-2.46 and $R^1$ has one of the meanings given in Table B.
Table 558: Compounds of the formula I1 wherein A is a radical A8-2.47 and $R^1$ has one of the meanings given in Table B.
Table 559: Compounds of the formula I1 wherein A is a radical A8-2.48 and $R^1$ has one of the meanings given in Table B.
Table 560: Compounds of the formula I1 wherein A is a radical A8-2.49 and $R^1$ has one of the meanings given in Table B.
Table 561: Compounds of the formula I1 wherein A is a radical A8-2.50 and $R^1$ has one of the meanings given in Table B.
Table 562: Compounds of the formula I1 wherein A is a radical A8-2.51 and $R^1$ has one of the meanings given in Table B.
Table 563: Compounds of the formula I1 wherein A is a radical A8-2.52 and $R^1$ has one of the meanings given in Table B.
Table 564: Compounds of the formula I1 wherein A is a radical A8-2.53 and $R^1$ has one of the meanings given in Table B.
Table 565: Compounds of the formula I1 wherein A is a radical A8-2.54 and $R^1$ has one of the meanings given in Table B.
Table 566: Compounds of the formula I1 wherein A is a radical A8-2.55 and $R^1$ has one of the meanings given in Table B.
Table 567: Compounds of the formula I1 wherein A is a radical A8-2.56 and $R^1$ has one of the meanings given in Table B.
Table 568: Compounds of the formula I1 wherein A is a radical A8-2.57 and $R^1$ has one of the meanings given in Table B.
Table 569: Compounds of the formula I1 wherein A is a radical A8-2.58 and $R^1$ has one of the meanings given in Table B.
Table 570: Compounds of the formula I1 wherein A is a radical A8-2.59 and $R^1$ has one of the meanings given in Table B.
Table 571: Compounds of the formula I1 wherein A is a radical A8-2.60 and $R^1$ has one of the meanings given in Table B.
Table 572: Compounds of the formula I1 wherein A is a radical A8-2.61 and $R^1$ has one of the meanings given in Table B.
Table 573: Compounds of the formula I1 wherein A is a radical A8-2.62 and $R^1$ has one of the meanings given in Table B.
Table 574: Compounds of the formula I1 wherein A is a radical A8-2.63 and $R^1$ has one of the meanings given in Table B.
Table 575: Compounds of the formula I1 wherein A is a radical A8-2.64 and $R^1$ has one of the meanings given in Table B.
Table 576: Compounds of the formula I1 wherein A is a radical A8-2.65 and $R^1$ has one of the meanings given in Table B.
Table 577: Compounds of the formula I1 wherein A is a radical A8-2.66 and $R^1$ has one of the meanings given in Table B.
Table 578: Compounds of the formula I1 wherein A is a radical A8-2.67 and $R^1$ has one of the meanings given in Table B.
Table 579: Compounds of the formula I1 wherein A is a radical A8-2.68 and $R^1$ has one of the meanings given in Table B.
Table 580: Compounds of the formula I1 wherein A is a radical A8-2.69 and $R^1$ has one of the meanings given in Table B.
Table 581: Compounds of the formula I1 wherein A is a radical A8-2.70 and $R^1$ has one of the meanings given in Table B.
Table 582: Compounds of the formula I1 wherein A is a radical A8-2.71 and $R^1$ has one of the meanings given in Table B.
Table 583: Compounds of the formula I1 wherein A is a radical A8-2.72 and $R^1$ has one of the meanings given in Table B.
Table 584: Compounds of the formula I1 wherein A is a radical A8-2.73 and $R^1$ has one of the meanings given in Table B.
Table 585: Compounds of the formula I1 wherein A is a radical A8-2.74 and $R^1$ has one of the meanings given in Table B.

Table 586: Compounds of the formula I1 wherein A is a radical A8-2.75 and $R^1$ has one of the meanings given in Table B.
Table 587: Compounds of the formula I1 wherein A is a radical A8-2.76 and $R^1$ has one of the meanings given in Table B.
Table 588: Compounds of the formula I1 wherein A is a radical A8-2.77 and $R^1$ has one of the meanings given in Table B.
Table 589: Compounds of the formula I1 wherein A is a radical A8-2.78 and $R^1$ has one of the meanings given in Table B.
Table 590: Compounds of the formula I1 wherein A is a radical A8-2.79 and $R^1$ has one of the meanings given in Table B.
Table 591: Compounds of the formula I1 wherein A is a radical A8-2.80 and $R^1$ has one of the meanings given in Table B.
Table 592: Compounds of the formula I1 wherein A is a radical A8-2.81 and $R^1$ has one of the meanings given in Table B.
Table 593: Compounds of the formula I1 wherein A is a radical A8-2.82 and $R^1$ has one of the meanings given in Table B.
Table 594: Compounds of the formula I1 wherein A is a radical A8-2.83 and $R^1$ has one of the meanings given in Table B.
Table 595: Compounds of the formula I1 wherein A is a radical A8-2.84 and $R^1$ has one of the meanings given in Table B.
Table 596: Compounds of the formula I1 wherein A is a radical A8-2.85 and $R^1$ has one of the meanings given in Table B.
Table 597: Compounds of the formula I1 wherein A is a radical A8-2.86 and $R^1$ has one of the meanings given in Table B.
Table 598: Compounds of the formula I1 wherein A is a radical A8-2.87 and $R^1$ has one of the meanings given in Table B.
Table 599: Compounds of the formula I1 wherein A is a radical A8-2.88 and $R^1$ has one of the meanings given in Table B.
Table 600: Compounds of the formula I1 wherein A is a radical A8-2.89 and $R^1$ has one of the meanings given in Table B.
Table 601: Compounds of the formula I1 wherein A is a radical A8-2.90 and $R^1$ has one of the meanings given in Table B.
Table 602: Compounds of the formula I1 wherein A is a radical A8-2.91 and $R^1$ has one of the meanings given in Table B.
Table 603: Compounds of the formula I1 wherein A is a radical A8-2.92 and $R^1$ has one of the meanings given in Table B.
Table 604: Compounds of the formula I1 wherein A is a radical A8-2.93 and $R^1$ has one of the meanings given in Table B.
Table 605: Compounds of the formula I1 wherein A is a radical A8-2.94 and $R^1$ has one of the meanings given in Table B.
Table 606: Compounds of the formula I1 wherein A is a radical A8-2.95 and $R^1$ has one of the meanings given in Table B.
Table 607: Compounds of the formula I1 wherein A is a radical A8-2.96 and $R^1$ has one of the meanings given in Table B.
Table 608: Compounds of the formula I1 wherein A is a radical A8-2.97 and $R^1$ has one of the meanings given in Table B.
Table 609: Compounds of the formula I1 wherein A is a radical A8-2.98 and $R^1$ has one of the meanings given in Table B.
Table 610: Compounds of the formula I1 wherein A is a radical A8-2.99 and $R^1$ has one of the meanings given in Table B.
Table 611: Compounds of the formula I1 wherein A is a radical A8-2.100 and $R^1$ has one of the meanings given in Table B.
Table 612: Compounds of the formula I1 wherein A is a radical A8-2.101 and $R^1$ has one of the meanings given in Table B.
Table 613: Compounds of the formula I1 wherein A is a radical A8-2.102 and $R^1$ has one of the meanings given in Table B.
Table 614: Compounds of the formula I1 wherein A is a radical A8-2.103 and $R^1$ has one of the meanings given in Table B.
Table 615: Compounds of the formula I1 wherein A is a radical A8-2.104 and $R^1$ has one of the meanings given in Table B.
Table 616: Compounds of the formula I1 wherein A is a radical A8-2.105 and $R^1$ has one of the meanings given in Table B.
Table 617: Compounds of the formula I1 wherein A is a radical A8-2.106 and $R^1$ has one of the meanings given in Table B.
Table 618: Compounds of the formula I1 wherein A is a radical A8-2.107 and $R^1$ has one of the meanings given in Table B.
Table 619: Compounds of the formula I1 wherein A is a radical A8-2.108 and $R^1$ has one of the meanings given in Table B.
Table 620: Compounds of the formula I1 wherein A is a radical A8-2.109 and $R^1$ has one of the meanings given in Table B.
Table 621: Compounds of the formula I1 wherein A is a radical A8-2.110 and $R^1$ has one of the meanings given in Table B.
Table 622: Compounds of the formula I1 wherein A is a radical A8-2.111 and $R^1$ has one of the meanings given in Table B.
Table 623: Compounds of the formula I1 wherein A is a radical A8-2.112 and $R^1$ has one of the meanings given in Table B.
Table 624: Compounds of the formula I1 wherein A is a radical A8-2.113 and $R^1$ has one of the meanings given in Table B.
Table 625: Compounds of the formula I1 wherein A is a radical A8-2.114 and $R^1$ has one of the meanings given in Table B.
Table 626: Compounds of the formula I1 wherein A is a radical A8-2.115 and $R^1$ has one of the meanings given in Table B.
Table 627: Compounds of the formula I1 wherein A is a radical A8-2.116 and $R^1$ has one of the meanings given in Table B.
Table 628: Compounds of the formula I1 wherein A is a radical A8-2.17 and $R^1$ has one of the meanings given in Table B.
Table 629: Compounds of the formula I1 wherein A is a radical A8-2.118 and $R^1$ has one of the meanings given in Table B.

Table 630: Compounds of the formula I1 wherein A is a radical A8-2.119 and $R^1$ has one of the meanings given in Table B.
Table 631: Compounds of the formula I1 wherein A is a radical A8-2.120 and $R^1$ has one of the meanings given in Table B.
Table 632: Compounds of the formula I1 wherein A is a radical A8-2.121 and $R^1$ has one of the meanings given in Table B.
Table 633: Compounds of the formula I1 wherein A is a radical A8-2.122 and $R^1$ has one of the meanings given in Table B.
Table 634: Compounds of the formula I1 wherein A is a radical A8-2.123 and $R^1$ has one of the meanings given in Table B.
Table 635: Compounds of the formula I1 wherein A is a radical A8-2.124 and $R^1$ has one of the meanings given in Table B.
Table 636: Compounds of the formula I1 wherein A is a radical A8-2.125 and $R^1$ has one of the meanings given in Table B.
Table 637: Compounds of the formula I1 wherein A is a radical A8-2.126 and $R^1$ has one of the meanings given in Table B.
Table 638: Compounds of the formula I1 wherein A is a radical A8-2.127 and $R^1$ has one of the meanings given in Table B.
Table 639: Compounds of the formula I1 wherein A is a radical A8-2.128 and $R^1$ has one of the meanings given in Table B.
Table 640: Compounds of the formula I1 wherein A is a radical A8-2.129 and $R^1$ has one of the meanings given in Table B.
Table 641: Compounds of the formula I1 wherein A is a radical A8-2.130 and $R^1$ has one of the meanings given in Table B.
Table 642: Compounds of the formula I1 wherein A is a radical A8-2.131 and $R^1$ has one of the meanings given in Table B.
Table 643: Compounds of the formula I1 wherein A is a radical A8-3.1 and $R^1$ has one of the meanings given in Table B.
Table 644: Compounds of the formula I1 wherein A is a radical A8-3.2 and $R^1$ has one of the meanings given in Table B.
Table 645: Compounds of the formula I1 wherein A is a radical A8-3.3 and $R^1$ has one of the meanings given in Table B.
Table 646: Compounds of the formula I1 wherein A is a radical A8-3.4 and $R^1$ has one of the meanings given in Table B.
Table 647: Compounds of the formula I1 wherein A is a radical A8-3.5 and $R^1$ has one of the meanings given in Table B.
Table 648: Compounds of the formula I1 wherein A is a radical A8-3.6 and $R^1$ has one of the meanings given in Table B.
Table 649: Compounds of the formula I1 wherein A is a radical A8-3.7 and $R^1$ has one of the meanings given in Table B.
Table 650: Compounds of the formula I1 wherein A is a radical A8-3.8 and $R^1$ has one of the meanings given in Table B.
Table 651: Compounds of the formula I1 wherein A is a radical A8-3.9 and $R^1$ has one of the meanings given in Table B.
Table 652: Compounds of the formula I1 wherein A is a radical A8-3.10 and $R^1$ has one of the meanings given in Table B.
Table 653: Compounds of the formula I1 wherein A is a radical A8-3.11 and $R^1$ has one of the meanings given in Table B.
Table 654: Compounds of the formula I1 wherein A is a radical A8-3.12 and $R^1$ has one of the meanings given in Table B.
Table 655: Compounds of the formula I1 wherein A is a radical A8-3.13 and $R^1$ has one of the meanings given in Table B.

Further examples of these preferred embodiments are represented by the salts and N-oxides of the preferred compounds according to the present invention as here above defined.

The compounds of the formula I, wherein X is O (compounds I1), can be prepared e.g. according to the method depicted in scheme 1 by reacting a N-(4-pyridazinyl)carboxamide II' with an activated compound $R^1$-LG (LG=leaving group) in sense of an N-alkylation reaction. The reaction can be performed by analogy to known N-alkylation of pyridazines. N-Alkylation of Pyridazines is known in literature and can be found in e.g.: N. Haider, G. Heinisch, *J. Chem. Soc., Perkin Trans.* 1 1988, 401 and S.-F. Chen, R. P. Panzica, *J. Org. Chem.* 1981, 46, 2467.

Scheme 1:

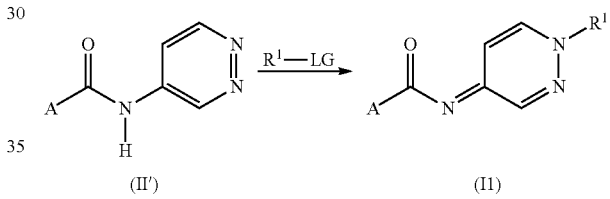

In scheme 1, the radicals A and $R^1$ have the meanings given above and in particular the meanings given as being preferred. LG is a classical leaving group. Classical leaving groups include halogen, such as Cl, Br, I, (halo)alkyl sulfonate and aryl sulfonate groups (R—$SO_2O$, where R is aryl such as phenyl, which is unsubstituted or carries 1, 2 or 3 inert radicals such as methyl, chlorine or methoxy or R is alkyl or haloalkyl) such as mesylate, phenylsulfonate, triflate (OTf) or tosylate, or LG may also be alkylsulfate such as methylsulfate ($CH_3OSO_2O$) or (halo)alkylcarboxylate such as acetate or trifluoroacetate.

The reaction of scheme 1 is particularly suitable for compounds, where LG is attached to $R^1$ via an aliphatic carbon atom, i.e. the carbon atom of $R^1$ to which LG is attached is an aliphatic carbon atom, in particular a primary ($CH_2$) or secondary (CH) carbon atom. The reaction of scheme 1 is customarily performed in the presence of a base. Suitable bases include e.g. alkalimetal hydrides, such as NaH, LiH, KH and the like, alkalimetal hydroxides such as NaOH, KOH and the like or alkalimetal carbonates such as $Na_2CO_3$, $K_2CO_3$ or $Cs_2CO_3$. The reaction is preferably performed in a solvent, more preferably in an aprotic solvent such as dimethylformamide (DMF), acetonitril, dimethyl sulfoxide (DMSO), dichloromethane (DCM), ketones such as cyclohexanone, acetone or methylethyl ketone or mixtures thereof.

The amount of base is preferably at least almost stoichiometric with regard to the compound $R^1$-LG, i.e. the amount of base is preferably at least 0.95 eq. with regard to the compound $R^1$-LG, in particular from 0.95 eq. to 5 eq. with regard to the compound R¹-LG. The compound R¹-LG may be used in almost stoichiometric amounts with regard to the compound of formula II' or in excess, e.g. from 0.9 to 5 mol per mol of compound II'. The reaction temperature may vary from 0° C. to reflux temperature of the reaction mixture, e.g. from 0° C. to 200° C. or from 5° C. to 150° C.

The compounds of the formula I, wherein X is O (compounds I1), can also be prepared according to the method depicted in scheme 2 by reacting a 1-substituted 4-pyridazinimine of the formula III with an acylating agent of the formula IV:

Scheme 2:

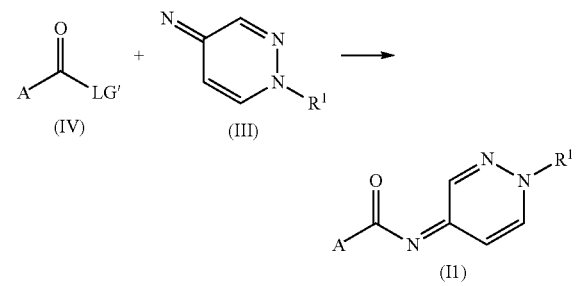

In scheme 2, the radicals A and R¹ have the meanings given above and in particular the meanings given as being preferred. LG' is a suitable leaving group such as OH, halogen, N3, para-nitrophenoxy or pentafluorophenoxy and the like. The reaction of scheme 2 is particularly suitable for compounds, where R¹ is aryl (i.e. optionally substituted phenyl) or hetaryl. Suitable acylating agents IV are carboxylic acids (i.e. LG' is OH) and activated carboxylic acid derivatives, where LG' is e.g. halogen, N3, para-nitrophenoxy or pentafluorophenoxy and the like.

The reaction of activated carboxylic acid derivatives can be performed by analogy to standard procedures such as disclosed in e.g. Houben-Weyl: "Methoden der organ. Chemie" [Methods of Organic Chemistry], Georg-Thieme-Verlag, Stuttgart, New York 1985, Volume E5, pp. 941-1045) or in EP 78989 or DE 3436550. Compounds IV, where LG' is OH are preferably reacted with compounds III in the presence of a coupling agent. Suitable coupling agents and reactions conditions can be taken e.g. from:

coupling agents based on carbodiimides, for example N,N'-dicyclohexylcarbodiimide [J. C. Sheehan, G. P. Hess, J. Am. Chem. Soc. 1955, 77, 1067], N-(3-dimethylaminopropyl)-N'-ethylcarbodiimide;

coupling agents which form mixed anhydrides with carbonic esters, for example 2-ethoxy-1-ethoxycarbonyl-1,2-dihydroquinoline [B. Belleau, G. Malek, J. Amer. Chem. Soc. 1968, 90, 1651], 2-isobutyloxy-1-isobutyloxycarbonyl-1,2-dihydroquinoline [Y. Kiso, H. Yajima, J. Chem. Soc., Chem. Commun. 1972, 942];

coupling agents based on phosphonium salts, for example (benzotriazol-1-yloxy)tris(dimethylamino)phosphonium hexafluorophosphate [B. Castro, J. R. Domoy, G. Evin, C. Selve, Tetrahedron Lett. 1975, 14, 1219], (benzotriazol-1-yloxy)tripyrrolidinophosphonium hexafluorophosphate [J. Coste et al., Tetrahedron Lett. 1990, 31, 205];

coupling agents based on uronium salts or having a guanidinium N-oxide structure, for example N,N,N',N'-tetramethyl-O-(1H-benzotriazol-1-yl)uronium hexafluorophosphate [R. Knorr, A. Trzeciak, W. Bannwarth, D. Gillessen, Tetrahedron Lett. 1989, 30, 1927], N,N,N',N'-tetramethyl-O-(benzotriazol-1-yl)uronium tetrafluoroborate, (benzotriazol-1-yloxy)dipiperidinocarbenium hexafluorophosphate [S. Chen, J. Xu, Tetrahedron Lett. 1992, 33, 647];

coupling agents which form acid chlorides, for example bis-(2-oxo-oxazolidinyl)phosphinic chloride [J. Diago-Mesequer, Synthesis 1980, 547].

The compounds of the formula III are known, e.g. from EP 78989, EP 227941 and DE 3436550 or can be prepared by analogy to the methods described therein.

Compounds with X=S can be prepared from above compounds of the formula I1 (X=O) according to the methods described in the art, e.g. by reacting a compound of formula I1 with 2,4-bis(4-methoxyphenyl)-1,3,2,4-dithiadiphosphetane-2,4-disulfide or phosphorus pentasulfide according to the method described by M. Jesberger et al. in Synthesis 2003, 1929.

N-oxides of the compounds of formulae I or I1, can be prepared by oxidation of compounds I or I1, according to standard methods of preparing heteroaromatic N-oxides, e.g. by the method described by C. Botteghi et al. in Journal of Organometallic Chemistry 1989, 370, 17-31.

As a rule, the compounds of formulae I or I1 can be prepared by the methods described above. If individual compounds can not be prepared via the above-described routes, they can be prepared by derivatization of other compounds I or II or by customary modifications of the synthesis routes described. For example, in individual cases, certain compounds I or I1 can advantageously be prepared from other compounds I or I1 by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the general formula I may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula (I) or a salt or N-oxide thereof or a composition as defined above.

Preferably, the method of the invention serves for protecting plant propagation material (such as seed) and the plant which grows therefrom from invertebrate pest attack or infestation and comprises treating the plant propagation material (such as seed) with a pesticidally effective amount of a compound of formula (I) or an agriculturally acceptable salt or N-oxide thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects preferably insects of the order Homoptera.

The invention further provides an agricultural composition for combating such invertebrate pests, which comprises such an amount of at least one compound of the general formula I or at least one agriculturally useful salt or N-oxide thereof and at least one inert liquid and/or solid agronomically acceptable carrier that has a pesticidal action and, if desired, at least one surfactant.

Such a composition may contain a single active compound of the formula I or a salt or N-oxide thereof or a mixture of several active compounds I or II or their salts according to the present invention. The composition according to the present invention may comprise an individual isomer or mixtures of isomers as well as individual tautomers or mixtures of tautomers.

The compounds of the formula I and the pesticidal compositions comprising them are effective agents for controlling arthropod pests and nematodes. Invertebrate pests controlled by the compounds of formula I include for example insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendroli mus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani and Zeiraphera canadensis;* beetles (Coleoptera), for example *Agrilus sinuatus, Agriotes lineatus, Agriotes obscu-rus, Amphimallus solstitialis, Anisandrus dispar, Anthonomus grandis, Anthonomus pomorum, Atomaria linearis, Blastophagus piniperda, Blitophaga undata, Bruchus rufi-manus, Bruchus pisorum, Bruchus lentis, Byctiscus betulae, Cassida nebulosa, Cero-toma trifurcata, Ceuthorrhynchus assimilis, Ceuthorrhynchus napi, Chaetocnema tibi-alis, Conoderus vespertinus, Crioceris asparagi, Diabrotica longicornis, Diabrotica 12 punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyl-lopertha horticola, Phyllotreta nemorum, Phyllotreta striolata, Popillia japonica, Sitona lineatus and Sitophilus granaria;* dipterans (Diptera), for example *Aedes aegypti, Aedes vexans, Anastrepha ludens, Anopheles maculipennis, Ceratitis capitata, Chrysomya bezziana, Chrysomya homi-nivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Bemisia tabaci, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melano-plus spretus, Nomadacris septemfasciata, Periplaneta americana, Schistocerca americana, Schistocerca peregrina, Stauronotus maroccanus* and *Tachycines asynamorus;* arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;* siphonatera, e.g. *Xenopsylla cheopsis, Ceratophyllus* spp.

The compositions and compounds of formula I are useful for the control of nematodes, especially plant parasitic nematodes such as root knot nematodes, *Meloidogyne hapla, Meloidogyne incognita, Meloidogyne javanica,* and other *Meloidogyne* species;

cyst-forming nematodes, *Globodera rostochiensis* and other *Globodera* species; *Het-erodera avenae, Heterodera* glycines, *Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nema-todes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploamus* species; false rootknot nematodes, *Nacobbus* species; Needle nematodes, *Longidorus elongatus* and other *Longidorus* species; Pin nematodes, *Paratylen-chus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by invertebrate pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation tech-nology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agro-chemicals, such as solvents and/or carriers, if desired emulsifiers, surfactants and dispersants, preservatives, anti-foaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone [NMP], N-octylpyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulphates, alkylsulfonates, fatty alcohol sulfates, fatty acids and sulphated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropyl-ene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, poly-ethyleneimines (Lupasol®, Polymin®), polyethers, polyurethans, polyvinylacetate, ty-lose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An example of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90 by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2- to 10-fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetting agents or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetting agents and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetting agents and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetting agents and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials (such as seed). Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1 to 800 g/l of active ingredient, 1 to 200 g/l surfactant, 0 to 200 g/l anti-freezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80% wt of the active ingredient, from 0.05 to 5% wt of a wetting agent, from 0.5 to 15% wt of a dispersing agent, from 0.1 to 5% wt of a thickener, from 5 to 20% wt of an anti-freeze agent, from 0.1 to 2% wt of an anti-foam agent, from 1 to 20% wt of a pigment and/or a dye, from 0 to 15% wt of a sticker/adhesion agent, from 0 to 75% wt of a filler/vehicle, and from 0.01 to 1% wt of a preservative.

Various types of oils, wetting agents, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitoes, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spraying devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cock-roaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g. in spray cans), oil sprays or pump sprays are highly suitable for the non-professional user for controlling pests such as flies, fleas, ticks, mosquitoes or cockroaches. Aerosol recipes are preferably corn-posed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethyl-formamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3 to 7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the active compounds of formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "un-sown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The active compounds can be applied solely or in a mixture with synergists or with other active compounds which act against pathogenic endo- and ectoparasites.

For example, the active compounds of formula I can be applied in mixtures with synthetic coccidiosis compounds, polyetherantibiotics as Amprolium, Robenidin, Toltrazuril, Monensin, Salinomycin, Maduramicin, Lasalocid, Narasin or Semduramicin or with other pesticides which are described in the list M below.

Compositions to be used according to this invention may also contain other active ingredients, for example other pesticides, insecticides, herbicides, fungicides, other pesticides, or bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of formula I or the compositions comprising them in the use form as pesticides with other pesticides frequently results in a broader pesticidal spectrum of action.

The following list M of pesticides together with which the compounds of formula I the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphosmethyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemetonmethyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cycloprothrin, cyfluthrin, betacyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultapsodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonists: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1);

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoroethylcarbamoyl)-methyl]-benzamide (M22.3), 4-[5-(3,5-Dichloro-phenyl)-5-trifluoromethyl-4,5-dihydro-isoxazol-3-yl]naphthalene-1-carboxylic acid [(2,2,2-trifluoro-ethylcarbamoyl)-methyl]-amide (M22.4), 4-[5-(3,5-Dichlorophenyl)-5-trifluoromethyl-4,5-dihydro-isoxazol-3-yl]-N-[(methoxyimino)methyl]-2-methylbenzamide (M22.5) 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 4-[5-(3,5-Dichloro-4-fluoro-phenyl)-5-trifluoromethyl-4,5-dihydro-isoxazol-3-yl]-2-[1,2,4]-triazol-1-yl-benzonitrile (M22.8); M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methylbenzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2HCF_2CF_2CF_2CH_2C(CN)_2CH_2CH_2CF_3$) (M24.1) and 2-(2,2,3,3,4,4,5,5-octafluoropentyl)-2-(3,3,4,4,4-pentafluorobutyl)-malonodinitrile ($CF_2HCF_2CF_2CF_2CH_2C(CN)_2$—$CH_2CH_2CF_2CF_3$) (M24.2);

M.25. Microbial disruptors: *Bacillus thuringiensis* subsp. *Israelensi, Bacillus sphaericus, Bacillus thuringiensis* subsp. *Aizawai, Bacillus thuringiensis* subsp. *Kurstaki, Bacillus thuringiensis* subsp. *Tenebrionis;*

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl] (2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2 (5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R''cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779.-AKD 1022 and its preparation have been described in U.S. Pat. No. 6,300,348.-M21.1 is known from WO 2007/101540.-Isoxazolines M22.1 to M22.8 have been described in e.g. WO2005/085216, WO 2007/079162, WO 2007/026965, WO 2009/126668 and WO2009/051956. Anthranilamides M23.1 to M23.6 have been described in WO 2008/72743 and WO 200872783, those M23.7 to M23.12 in WO 2007/043677. Malononitriles M24.1 and M24.2 have been described in WO 02/089579, WO 02/090320, WO 02/090321, WO 04/006677, WO 05/068423, WO 05/068432 and WO 05/063694. M26.1 to M6.10 have been described eg. in WO 2007/115644. M27.1 is described e.g. in JP 2006131529. Organic sulfur compounds have been described in WO 2007060839. M27.2 has been described in WO 2008/66153 and WO 2008/108491. M27.3 has been described in JP 2008/115155.

Fungicidal mixing partners are in particular those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, enestroburin, fluoxastrobin, kresoxim-methyl, metominostrobin, orysastrobin, picoxystrobin, pyraclostrobin, pyribencarb or trifloxystrobin, sulfenic acid derivatives such as captafol, captan, dichlofluanid, folpet, tolylfluanid, cinnemamides and analogs such as dimethomorph, flumetover or flumorph.

The invertebrate pest, i.e. arthropodes and nematodes, the plant, soil or water in which the plant is growing can be contacted with the compound(s) of formula I or composition(s) containing them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

Moreover, invertebrate pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

"Locus" in general means a habitat, breeding ground, cultivated plants, plant propagation material (such as seed), soil, area, material or environment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and the compositions comprising said compounds can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the under-floor soil in order to protect wooden materials but it can also be applied to lumbered articles such as surfaces of the under-floor concrete, alcove posts, beams, plywood, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula I can also be applied preventively to places at which occurrence of the pests is expected.

The compounds of formula I may also be used to protect growing plants from attack or infestation by pests by contacting the plant with a pesticidally effective amount of compounds of formula I. As such, "contacting the plant" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m², preferably from 0.001 to 20 g per 100 m².

Customary application rates in the protection of materials are, for example, from 0.01 g to 1000 g of active compound per m² treated material, desirably from 0.1 g to 50 g per m².

Insecticidal compositions for use in the impregnation of materials typically contain from 0.001 to 95% by weight, preferably from 0.1 to 45% by weight, and more preferably from 1 to 25% by weight of at least one repellent and/or insecticide.

For use in bait compositions, the typical content of active ingredient is from 0.001% by weight to 15% by weight, desirably from 0.001% by weight to 5% by weight of active compound.

For use in spray compositions, the content of active ingredient is from 0.001 to 80% by weight, preferably from 0.01 to 50% by weight and most preferably from 0.01 to 15% by weight.

For use in treating crop plants, the rate of application of the active ingredients of this invention may be in the range of 0.1 g to 4000 g per hectare, desirably from 5 g to 600 g per hectare, more desirably from 10 g to 300 g per hectare.

In the treatment of seed, the application rates of the active ingredients are generally from 0.1 g to 10 kg per 100 kg of seed, preferably from 1 g to 1 kg per 100 kg of seed, in particular from 1 g to 250 g per 100 kg of seed, in particular from 10 g to 150 g per 100 kg of seed.

The present invention is now illustrated in further detail by the following examples.

I. PREPARATION EXAMPLES

With appropriate modification of the starting materials, the procedures given in the synthesis example below were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) determined by HPLC-MS spectrometry.

HPLC-MS=high performance liquid chromatography-coupled mass spectrometry; HPLC conditions for examples 1-27: HPLC column: RP-18 column (Chromolith® Speed ROD from Merck KgaA, Germany), 50*4.6 mm; mobile phase: acetonitrile+0.1% trifluoroacetic acid (TFA)/water+0.1% TFA, using a gradient of 5:95 to 100:0 over 5 minutes at 40° C., flow rate 1.8 ml/min.

HPLC conditions for examples 28-32: HPLC column: RP-18 column (Kinetex™ XB C18 1.7μ from Phenomenex, Germany), 50*2.0 mm; mobile phase: acetonitrile+0.1% trifluoroacetic acid (TFA)/water+0.1% TFA, using a gradient of 5:95 to 100:0 over 1.5 minutes at 60° C., flow rate 0.8 ml/min to 1.0 ml/min.

MS: quadrupole electrospray ionization, 80 V (positive mode).]

Preparation of 5-methyl-1-(2,2,2-trifluoro-ethyl)-1H-pyrazole-4-carboxylic acid [1-methyl-1H-pyridazin-(4E)-ylidene]-amide

Example 7

5-Methyl-1-(2,2,2-trifluoro-ethyl)-1H-pyrazole-4-carboxylic acid pyridazin-4-ylamide (500 mg, 1.75 mmol, 1.0 equiv.) and caesium carbonate (1.43 g, 2.28 mmol, 2.5 equiv) were suspended in 30 ml Dimethylformamide (DMF). Methyl iodide (324 mg, 2.28 mmol, 1.3 equiv) was added and the mixture was stirred at 60° C. overnight. The solvent was removed under reduced pressure and the residue was diluted with CH₂Cl₂ and washed with water. The layers were separated and the organic layer was dried over Na₂SO₄, filtered and the solvent was removed under reduced pressure. The residue was triturated with a mixture of petrolether and methyl-tert-butylether (MTBE) to yield 259 mg of the title compound (47%, 95% purity). LC-MS: Ret. 1.840 min, 300.1 [M⁺]

Examples

Compounds of Formula I

| Ex. | A | X | R¹ | r.t. [min] | m |
|---|---|---|---|---|---|
| 1 | 5-difluoromethyl-1-(2,2,2-trifluoro-ethyl)-1H-pyrazol-4 yl | O | pyridin-2-ylmethyl | 2.285 | 413.0 |
| 2 | 5-methyl-1-(2,2,2-trifluoroethyl)-1H-pyrazol-4 yl | O | pyridin-2-ylmethyl | 2.026 | 377.1 |
| 3 | 5-methyl-1-(2,2,2-trifluoroethyl)-1H-pyrazol-4 yl | O | allyl | 1.992 | 326.1 |
| 4 | 5-difluoromethyl-1-(2,2,2-trifluoro-ethyl)-1H-pyrazol-4 yl | O | pyridin-3-ylmethyl | 1.851 | 413.0 |
| 5 | 5-methyl-1-(2,2,2-trifluoroethyl)-1H-pyrazol-4 yl | O | pyridin-3-ylmethyl | 1.600 | 377.1 |
| 6 | 5-difluoromethyl-1-(2,2,2-trifluoro-ethyl)-1H-pyrazol-4 yl | O | tetrahydro-furan-2-ylmethyl | 2.313 | 406.1 |
| 7 | 5-methyl-1-(2,2,2-trifluoroethyl)-1H-pyrazol-4 yl | O | methyl | 1.840 | 300.1 |
| 8 | 1-(2-methoxyethyl)-5-methyl-1H-pyrazol-4-yl | O | pyridin-2-ylmethyl | 1.829 | 353.2 |
| 9 | 1-(2-methoxyethyl)-5-methyl-1H-pyrazol-4-yl | O | benzyl | 2.254 | 352.1 |
| 10 | 1-(cyclopropylmethyl)-5-methyl-1H-pyrazol-4-yl | O | pyridin-2-ylmethyl | 2.128 | 349.1 |
| 11 | 1-(cyclopropylmethyl)-5-methyl-1H-pyrazol-4-yl | O | benzyl | 2.504 | 348.1 |
| 12 | 1-isopropyl-5-methyl-1H-pyrazol-4-yl | O | pyridin-2-ylmethyl | 2.032 | 337.1 |
| 13 | 1-isopropyl-5-methyl-1H-pyrazol-4-yl | O | benzyl | 2.431 | 336.1 |
| 14 | 1-(cyclopropylmethyl)-5-methyl-1H-pyrazol-4-yl | O | methyl | 1.915 | 272.1 |
| 15 | 1-(cyclopropylmethyl)-5-methyl-1H-pyrazol-4-yl | O | allyl | 2.133 | 298.1 |
| 16 | 1-isopropyl-5-methyl-1H-pyrazol-4-yl | O | methyl | 1.756 | 260.1 |
| 17 | 1-isopropyl-5-methyl-1H-pyrazol-4-yl | O | allyl | 2.042 | 286.1 |
| 18 | 4-methylthiazol-5-yl | O | benzyl | 2.109 | 311.0 |
| 19 | 4-methylthiazol-5-yl | O | pyridin-2-ylmethyl | 1.687 | 312.0 |
| 20 | 4-methylthiazol-5-yl | O | allyl | 1.617 | 261.1 |
| 21 | 3-methyl-isothiazol-4-yl | O | benzyl | 2.162 | 311.1 |
| 22 | 3-methyl-isoxazol-4-yl | O | benzyl | 2.178 | 295.1 |
| 23 | 2,4-dimethylpyrimidin-5-yl | O | methyl | 1.266 | 244.0 |

-continued

| Ex. | A | X | R¹ | r.t. [min] | m |
|---|---|---|---|---|---|
| 24 | 2,4-dimethylpyrimidin-5-yl | O | benzyl | 1.994 | 320.0 |
| 25 | 2,4-dimethylpyrimidin-5-yl | O | pyridin-2-ylmethyl | 1.617 | 321.0 |
| 27 | 1-isopropyl-5-methyl-1H-pyrazol-4-yl | O | methoxymethyl | 1.873 | 290.1 |
| 28 | 5-methyl-1-(2,2,2-trifluoro-1-methyl-ethyl)-1H-pyrazol-4-yl | O | methoxymethyl | 0.759 | 344.1 |
| 29 | 5-methyl-1-(2,2,2-trifluoro-1-methyl-ethyl)-1H-pyrazol-4-yl | O | benzyl | 0.905 | 390.1 |
| 30 | 5-methyl-1-(2,2,2-trifluoro-1-methyl-ethyl)-1H-pyrazol-4-yl | O | pyridin-2-ylmethyl | 0.802 | 391.1 |
| 31 | 5-methyl-1-(2,2,2-trifluoro-1-methyl-ethyl)-1H-pyrazol-4-yl | O | allyl | 0.795 | 340.1 |
| 32 | 5-methyl-1-(2,2,2-trifluoro-1-methyl-ethyl)-1H-pyrazol-4-yl | O | methyl | 0.721 | 314.1 | r.t. = HPLC retention time
m = molecular mass of [M]⁺ peaks

II. EVALUATION OF PESTICIDAL ACTIVITY

II.1 Cotton Aphid (*Aphis gossypii*, Mixed Life Stages)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 2, 3, 4, 5, 6, 7, 8, 10, 11, 12, 15, 16, 17, 24 and 25, resp., at 300 ppm showed a mortality of at least 75% in comparison with untreated controls.

II.2 Green Peach Aphid (*Myzus persicae*, Mixed Life Stages)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds 1, 2, 6, 7, 8, 9, 10, 11, 12, 13, 14, 15, 16, 17, 23, 24 and 25, resp., at 300 ppm showed a mortality of at least 75% in comparison with untreated controls.

II.3 Cowpea Aphid (*Aphis craccivora*)

The active compounds were formulated in 50:50 (vol:vol) acetone:water. The test solution was prepared at the day of use.

Potted cowpea plants colonized with 100-150 aphids of various stages were sprayed after the pest population had been recorded. Population reduction was assessed after 24, 72, and 120 hours.

In this test, the compounds 1, 2, 3, 4, 5, 6, 7, 8, 9, 10, 11, 12, 13, 14, 16, 17, 21, 23, 24 and 25, resp., at 300 ppm showed a mortality of at least 90% in comparison with untreated controls.

II.4 Vetch Aphid (*Megoura viciae*)

The active compounds were formulated in 1:3 (vol:vol) DMSO:water with different concentrations of formulated compounds.

Bean leaf disks were placed into microtiterplates filled with 0.8% agar-agar and 2.5 ppm OPUS™. The leaf disks were sprayed with 2.5 μl of the test solution and 5 to 8 adult aphids were placed into the microtiterplates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds 1, 3, 4, 6, 7, 8, 9, 10, 11, 12, 13, 15, 17 and 27, resp. at a concentration of the test solution of 2500 mg/L showed a mortality of at least 90%.

II.5 Boll Weevil (*Anthonomus grandis*)

The compounds were formulated in 75:25 (vol:vol) water:DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 μl, using a custom built micro atomizer, at two replications. After application, the microtiter plates were incubated at 23±1° C. and 50±5% relative humidity for 5 days. Egg and larval mortality was then visually assessed.

In this test, the compounds 2, 4, 6, 8, 12, 13 and 22, resp. at a concentration of the test solution of 2500 mg/L showed a mortality of at least 50%.

II.6 Activity Against Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications. After application, 5 to 8 adult aphids were placed on the artificial membrane inside the microtiter plate wells. The aphids were then allowed to suck on the treated aphid diet and incubated at about 23+1° C. and about 50+5% relative humidity for 3 days. Aphid mortality and fecundity was then visually assessed.

In this test, compounds 1, 2, 3, 4, 5, 6, 7, 8, 9, 10, 11, 12, 13, 14, 15, 16, 17, 23, 24, 25 and 27, resp., at 2500 ppm showed 100% mortality in comparison with untreated controls.

II.7 Silverleaf Whitefly (*Bemisia argentifolii*, Adult)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days old) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 2, 3, 4, 6, 7, 8, 9, 10, 12, 15 and 17, resp., at 300 ppm showed a mortality of at least 75% in comparison with untreated controls.

The invention claimed is:
1. A compound of formula (I)

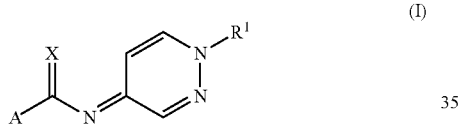

(I)

wherein
X is S or O;
$R^1$ is CN, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, $C_1$-$C_5$-alkylen-CN, $C_1$-$C_5$-alkylen-OR$^a$, C(Y)R$^b$, $C_1$-$C_5$-alkylen-C(Y)R$^b$, C(Y)OR$^c$, $C_1$-$C_5$-alkylen-C(Y)OR$^c$, S(O)$_m$R$^d$, $C_1$-$C_5$-alkylen-NR$^e$R$^f$, C(Y)NR$^g$R$^h$, $C_1$-$C_5$-alkylen-C(Y)NR$^g$R$^h$, S(O)$_m$NR$^e$R$^f$, C(Y)NR$^i$NR$^e$R$^f$, $C_1$-$C_5$-alkylen-S(O)$_m$R$^d$, $C_1$-$C_5$-alkylen-S(O)$_m$NR$^e$R$^f$, $C_1$-$C_5$-alkylen-C(Y)NR$^i$NR$^e$R$^f$, phenyl, heterocyclyl, hetaryl, phenyl-$C_1$-$C_5$-alkyl, $C_3$-$C_{10}$-cycloalkyl, $C_3$-$C_{10}$-cycloalkyl-$C_1$-$C_5$-alkyl, phenoxy-$C_1$-$C_5$-alkyl, heterocyclyl-$C_1$-$C_5$-alkyl, or hetaryl-$C_1$-$C_5$-alkyl wherein the ring of the nine last mentioned radicals may be unsubstituted or may carry 1, 2, 3, 4 or 5 identical or different substituents selected from the radicals R$^y$;
A is 5- or 6-membered hetaryl having one heteroatom moiety which is selected from the group consisting of O, S, NH and N—R$^N$ as ring member and 0, 1 or 2 further heteroatom moieties N as ring members and also having 2, 3, 4 or 5 carbon atoms as ring members where the carbon atom ring members may be unsubstituted or 1, 2, 3 or 4 of the carbon atom ring members carry a radical $R^A$ as a substituent, where
$R^A$ is selected from the group consisting of halogen, CN, $NO_2$, $C_1$-$C_{10}$-alkyl, $C_2$-$C_{10}$-alkenyl and $C_2$-$C_{10}$-alkynyl, wherein the last three mentioned radicals may be unsubstituted, may be partially or fully halogenated or may carry 1, 2 or 3 identical or different substituents R$^x$,
or from the group consisting of OR$^a$, C(Y)R$^b$, C(Y)OR$^c$, S(O)$_m$R$^d$, NR$^e$R$^f$, heterocyclyl, phenyl, hetaryl, $C_3$-$C_{10}$-cycloalkyl and $C_5$-$C_{10}$-cycloalkenyl, wherein the last five mentioned radicals may be unsubstituted or may carry 1, 2, 3, 4 or 5 identical or different substituents R$^y$; and $R^N$ is selected from the group consisting of hydrogen, CN, $NO_2$, $C_1$-$C_{10}$-alkyl, $C_2$-$C_{10}$-alkenyl and $C_2$-$C_{10}$-alkynyl, wherein the three last mentioned radicals may be unsubstituted, may be partially or fully halogenated or may carry 1, 2 or 3 identical or different substituents R$^x$,
or from the group consisting of OR$^a$, C(Y)R$^b$, C(Y)OR$^c$, S(O)$_m$R$^d$, NR$^e$R$^f$, C(Y)NR$^g$R$^h$, S(O)$_m$NR$^e$R$^f$, C(Y)NR$^i$NR$^e$R$^f$, $C_1$-$C_5$-alkylen-OR$^a$, $C_1$-$C_5$-alkylen-CN, $C_1$-$C_5$-alkylen-C(Y)R$^b$, $C_1$-$C_5$-alkylen-C(Y)OR$^c$, $C_1$-$C_5$-alkylen-NR$^e$R$^f$, $C_1$-$C_5$-alkylen-C(Y)NR$^g$R$^h$, $C_1$-$C_5$-alkylen-S(O)$_m$R$^d$, $C_1$-$C_5$-alkylen-S(O)$_m$NR$^e$R$^f$, $C_1$-$C_5$-alkylen-NR$^i$NR$^e$R$^f$, heterocyclyl, hetaryl, $C_3$-$C_{10}$-cycloalkyl, $C_5$-$C_{10}$-cycloalkenyl, heterocyclyl-$C_1$-$C_5$-alkyl, hetaryl-$C_1$-$C_5$-alkyl, $C_3$-$C_{10}$-cycloalkenyl-$C_1$-$C_5$-alkyl, $C_5$-$C_{10}$-cycloalkenyl-$C_1$-$C_5$-alkyl, phenyl-$C_1$-$C_5$-alkyl and phenyl, wherein the rings of the ten last mentioned radicals may be unsubstituted or may carry 1, 2, 3, 4 or 5 identical or different substituents R$^y$;
m is 0, 1 or 2;
Y is O or S;
$R^a$, $R^b$, and $R^c$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl, wherein the ring in the six last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;
$R^d$ is selected from the group consisting of $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$-alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;
$R^e$ and $R^f$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, phenyl, phenylcarbonyl, phenylsulfonyl, hetaryl, hetarylcarbonyl, hetarylsulfonyl, heterocyclyl, heterocyclylcarbonyl, heterocyclylsulfonyl, phenyl-$C_1$-$C_4$-alkyl, hetaryl-$C_1$-$C_4$-alkyl and heterocyclyl-$C_1$-$C_4$-alkyl wherein the ring in the twelve last mentioned radicals may be unsubstituted or may carry 1, 2, 3, 4 or 5 substituents which, independently of each other, are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from the group consisting of O, S and N as a ring member atom and wherein the heterocycle may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^g$ and $R^h$ are independently of each other selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, hetaryl, heterocyclyl, phenyl-$C_1$-$C_4$alkyl, hetaryl-$C_1$-$C_4$-alkyl and heterocyclyl-$C_1$-$C_4$-alkyl wherein the ring in the six last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$alkoxy and $C_1$-$C_4$-haloalkoxy;

$R^i$ is selected from the group consisting of hydrogen, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^x$ are independently of each other selected from the group consisting of cyano, nitro, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_{10}$-alkylcarbonyl, $C_3$-$C_6$-cycloalkyl, 5- to 7-membered heterocyclyl, phenyl, $C_3$-$C_6$-cycloalkoxy, 3- to 6-membered heterocyclyloxy and phenoxy, wherein the last 6 mentioned radicals may be unsubstituted or may carry 1, 2, 3, 4 or 5 radicals selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

$R^y$ is selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_3$-$C_6$-cycloalkyl, 5- to 7-membered heterocyclyl, hetaryl, phenyl, $C_3$-$C_6$-cycloalkoxy, 3- to 6-membered heterocyclyloxy, hetaryloxy and phenoxy, wherein the last 8 mentioned radicals may be unsubstituted or may carry 1, 2, 3, 4 or 5 radicals selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy;

or a salt, N-oxide, or tautomer thereof or a salt of an N-oxide or a tautomer thereof.

2. The compound of claim 1, wherein A is 5-membered hetaryl having formula (A1), formula (A2), formula (A3), formula (A4), formula (A5), formula (A6), or formula (A7):

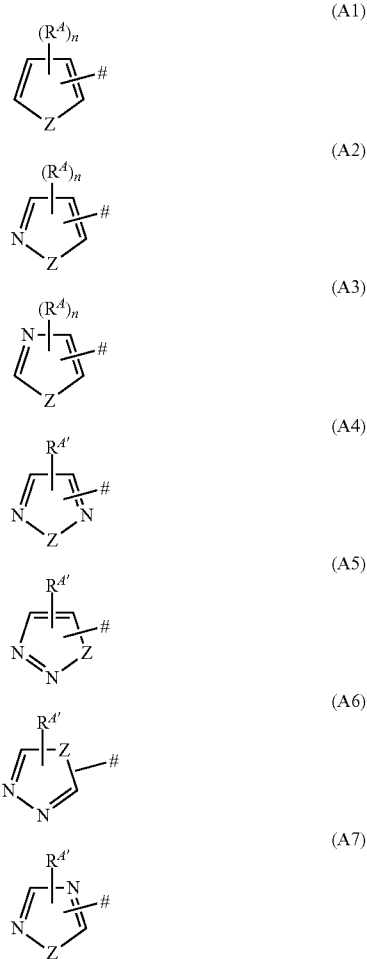

wherein
denotes the point of attachment to the remainder of formula (I),
Z is O, S or $NR^N$;
n is 0, 1, 2 or 3, and
$R^{A'}$ is hydrogen or $R^A$.

3. The compound of claim 2, wherein Z is $NR^N$ with $R^N$ being selected from the group consisting of $C_1$-$C_6$-alkyl, $C_1$-$C_6$-haloalkyl, heterocyclyl-$C_1$-$C_4$-alkyl, $C_1$-$C_4$-alkoxy-$C_1$-$C_4$-alkyl, $C_1$-$C_4$-alkylene-CN, $C_3$-$C_6$-cycloalkyl, $C_3$-$C_6$-cycloalkyl-$C_1$-$C_4$-alkyl, where the cycloalkyl moiety is in the last two mentioned radicals is unsubstituted or carries 1 or 2 radicals selected from the group consisting of halogen, CN and $C_1$-$C_2$-haloalkyl.

4. The compound of claim 3, wherein A is a radical of formula (A2), X is O and Z is $NR^N$ with $R^N$ being $C_1$-$C_6$-alkyl or $C_1$-$C_6$-haloalkyl.

5. The compound of claim 2, wherein A is a radical of formula (A2).

6. The compound of claim 2, wherein A is a radical of formula (A1).

7. The compound of claim 2, wherein A is a radical of formula (A3).

8. The compound of claim 2, wherein A is selected from the group consisting of radicals of formula (A4), formula (A5), formula (A6), and formula (A7).

9. The compound of claim 1, wherein A is selected from the group consisting of the radicals of formula (A8-1), formula (A8-2), formula (A8-3), formula (A8-4), formula (A8-5), formula (A8-6), formula (A8-7), formula (A8-8) and formula (A8-9):

(A8-1)

(A8-2)

(A8-3)

(A8-4)

(A8-5)

(A8-6)

(A8-7)

(A8-8)

(A8-9)

wherein denotes the point of attachment to the remainder of formula (I), and $R^{Z1}$, $R^{Z2}$, $R^{Z3}$, $R^{Z4}$ and $R^{Z5}$ if present, are independently of each other selected from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_3$-alkylen-CN, $C_1$-$C_3$-alkylen-$OR^a$, $C_3$-$C_7$-cycloalkyl, $C_3$-$C_7$-cycloalkyl-$C_1$-$C_3$-alkyl, and 3- to 7-membered saturated heterocyclyl-$C_1$-$C_3$-alkyl, wherein cycloalkyl and heterocyclyl in the 3 last mentioned radicals may be unsubstituted or may carry 1, 2, 3, 4 or 5 identical or different substituents $R^y$.

10. The compound of claim 9, wherein $R^{Z1}$, $R^{Z2}$, $R^{Z3}$, $R^{Z4}$ and $R^{Z5}$, if present, are independently of each other selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

11. The compound of claim 1, wherein $R^1$ is selected from the group consisting of $C_1$-$C_{10}$-alkyl, $C_1$-$C_{10}$-haloalkyl, $C_3$-$C_{10}$-alkenyl, $C_3$-$C_{10}$-alkynyl, $C_1$-$C_4$-alkylene-CN, $C_1$-$C_4$-alkylene-$OR^a$, phenyl-$C_1$-$C_4$-alkyl, $C_3$-$C_{10}$-cycloalkyl-$C_1$-$C_4$-alkyl, 5- or 6-membered saturated heterocyclyl-$C_1$-$C_4$-alkyl, and 5- or 6-membered hetaryl-$C_1$-$C_4$-alkyl, where the cycloalkyl ring and the heterocyclyl ring in $C_3$-$C_{10}$-cycloalkyl-$C_1$-$C_4$-alkyl and heterocyclyl-$C_1$-$C_4$-alkyl, respectively, is unsubstituted or carry 1, 2, 3, 4 or 5 identical or different substituents $R^y$, and where the phenyl ring and the hetaryl ring in phenyl-$C_1$-$C_4$-alkyl and hetaryl-$C_1$-$C_4$-alkyl, respectively, is unsubstituted or carry 1, 2, 3, 4 or 5 identical or different substituents $R^y$.

12. The compound of claim 1 wherein X is O.

13. The compound of claim 1, wherein $R^A$, if present, is selected from the group consisting of halogen, $NO_2$, $C_1$-$C_4$-alkyl, $C_1$-$C_4$-haloalkyl, $C_3$-$C_6$-cycloalkyl and $C_3$-$C_6$-halocycloalkyl.

14. A method for controlling invertebrate pests which method comprises treating the pests, their food supply, their habitat or their breeding ground or a plant, seed, soil, area, material or environment in which the pests are growing or may grow, or the materials, plants, seeds, soils, surfaces or spaces to be protected from pest attack or infestation with a pesticidally effective amount of a compound of formula I, as defined in claim 1, or a salt, N-oxide, or tautomer thereof.

15. The method of claim 14, wherein A is 5-membered hetaryl having formula (A1), formula (A2), formula (A3), formula (A4), formula (A5), formula (A6), or formula (A7):

(A1)

(A2)

-continued

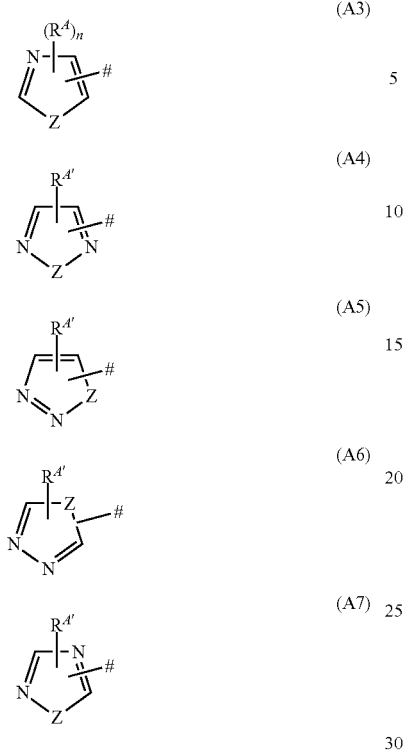

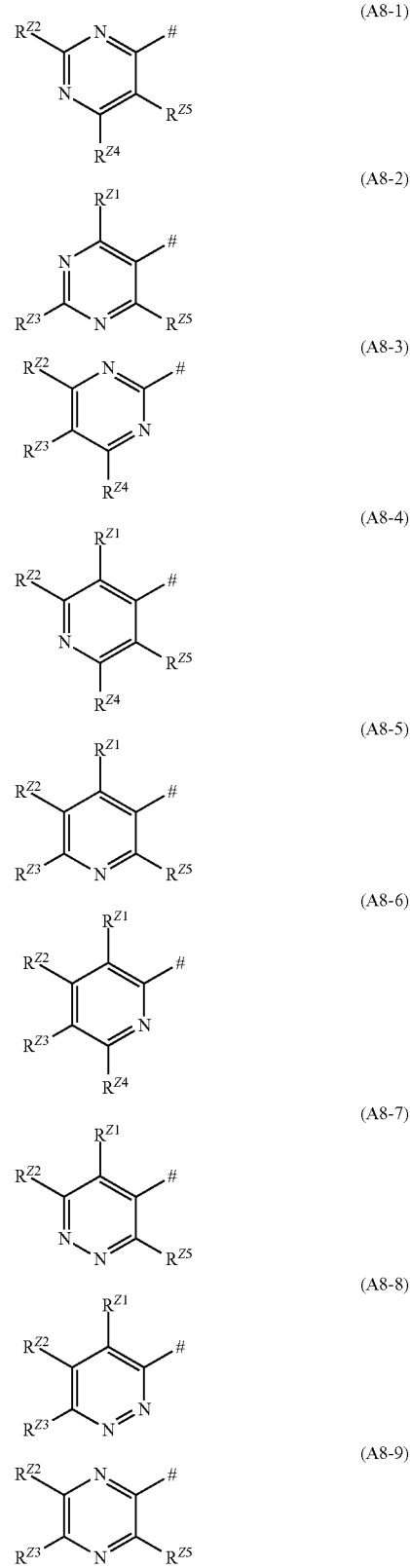

wherein
denotes the point of attachment to the remainder of formula (I),
Z is O, S or $NR^N$;
n is 0, 1, 2 or 3, and
$R^{A'}$ is hydrogen or $R^A$.

16. The method of claim 15, wherein Z is $NR^N$ with $R^N$ being selected from the group consisting of $C_1$-$C_6$-alkyl, $C_1$-$C_6$-haloalkyl, heterocyclyl-$C_1$-$C_4$-alkyl, $C_1$-$C_4$-alkoxy-$C_1$-$C_4$-alkyl, $C_1$-$C_4$-alkylene-CN, $C_3$-$C_6$-cycloalkyl, $C_3$-$C_6$-cycloalkyl-$C_1$-$C_4$-alkyl, where the cycloalkyl moiety is in the last two mentioned radicals is unsubstituted or carries 1 or 2 radicals selected from the group consisting of halogen, CN and $C_1$-$C_2$-haloalkyl.

17. The method of claim 16, wherein A is a radical of formula (A2), X is O and Z is $NR^N$ with $R^N$ being $C_1$-$C_6$-alkyl or $C_1$-$C_6$-haloalkyl.

18. The method of claim 15, wherein A is a radical of formula (A2).

19. The method of claim 15, wherein A is a radical of formula (A1).

20. The method of claim 15, wherein A is a radical of formula (A3).

21. The method of claim 15, wherein A is selected from the group consisting of radicals of formula (A4), formula (A5), formula (A6), and formula (A7).

22. The method of claim 14, wherein A is selected from the group consisting of the radicals of formula (A8-1), formula (A8-2), formula (A8-3), formula (A8-4), formula (A8-5), formula (A8-6), formula (A8-7), formula (A8-8) and formula (A8-9):

wherein
denotes the point of attachment to the remainder of formula (I), and $R^{Z1}$, $R^{Z2}$, $R^{Z3}$, $R^{Z4}$ and $R^{Z5}$ if present, are independently of each other selected from the group consisting of hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_3$-alkylen-$OR^a$, $C_3$-$C_7$-cycloalkyl, $C_3$-$C_7$-cycloalkyl-$C_1$-$C_3$-alkyl, and 3- to 7-membered saturated heterocyclyl-$C_1$-$C_3$-alkyl, wherein cycloalkyl and heterocyclyl in the 3 last mentioned radicals may be unsubstituted or may carry 1, 2, 3, 4 or 5 identical or different substituents $R^y$.

23. The method of claim 22, wherein $R^{Z1}$, $R^{Z2}$, $R^{Z3}$, $R^{Z4}$ and $R^{Z5}$, if present, are independently of each other selected from the group consisting of hydrogen, halogen, $C_1$-$C_4$-alkyl, $C_1$-$C_4$-haloalkyl, $C_3$-$C_6$-cycloalkyl and $C_3$-$C_6$-halocycloalkyl.

24. The method of claim 14, wherein $R^1$ is selected from the group consisting of $C_1$-$C_{10}$-alkyl, $C_1$-$C_{10}$-haloalkyl, $C_3$-$C_{10}$-alkenyl, $C_3$-$C_{10}$-alkynyl, $C_1$-$C_4$-alkylene-CN, $C_1$-$C_4$-alkylene-$OR^a$, phenyl-$C_1$-$C_4$-alkyl, $C_3$-$C_{10}$-cycloalkyl-$C_1$-$C_4$-alkyl, 5- or 6-membered saturated heterocyclyl-$C_1$-$C_4$-alkyl, and 5- or 6-membered hetaryl-$C_1$-$C_4$-alkyl, where the cycloalkyl ring and the heterocyclyl ring in $C_3$-$C_{10}$-cycloalkyl-$C_1$-$C_4$-alkyl and heterocyclyl-$C_1$-$C_4$-alkyl, respectively, is unsubstituted or carry 1, 2, 3, 4 or 5 identical or different substituents $R^y$, and where the phenyl ring and the hetaryl ring in phenyl-$C_1$-$C_4$-alkyl and hetaryl-$C_1$-$C_4$-alkyl, respectively, is unsubstituted or carry 1, 2, 3, 4 or 5 identical or different substituents $R^y$.

25. The method of claim 14 wherein X is O.

26. The method of claim 14, wherein $R^A$, if present, is selected from the group consisting of halogen, $NO_2$, $C_1$-$C_4$-alkyl, $C_1$-$C_4$-haloalkyl, $C_3$-$C_6$-cycloalkyl and $C_3$-$C_6$-halocycloalkyl.

\* \* \* \* \*